(12) United States Patent
Salles et al.

(10) Patent No.: US 9,120,856 B2
(45) Date of Patent: Sep. 1, 2015

(54) ANTI-CD19 ANTIBODY HAVING ADCC FUNCTION WITH IMPROVED GLYCOSYLATION PROFILE

(75) Inventors: Gilles Salles, Sainte-Foy-les-Lyon (FR); Claudine Vermot-Desroches, Dardilly (FR)

(73) Assignees: INTERNATIONAL-DRUG-DEVELOPMENT BIOTECH, Dardilly (FR); UCBL UNIVERSITE CLAUDE BERNARD DE LYON 1, Villeurbanne Cedex (FR); HOSPICES CIVILS DE LYON, Lyons (FR)

( * ) Notice: Subject to any disclaimer, the term of this patent is extended or adjusted under 35 U.S.C. 154(b) by 0 days.

(21) Appl. No.: 13/811,159

(22) PCT Filed: Jul. 18, 2011

(86) PCT No.: PCT/EP2011/062270
§ 371 (c)(1),
(2), (4) Date: Mar. 11, 2013

(87) PCT Pub. No.: WO2012/010561
PCT Pub. Date: Jan. 26, 2012

(65) Prior Publication Data
US 2013/0183306 A1 Jul. 18, 2013

Related U.S. Application Data

(60) Provisional application No. 61/365,569, filed on Jul. 19, 2010.

(30) Foreign Application Priority Data

Jul. 19, 2010 (FR) .................................. 10305797.2

(51) Int. Cl.
C07K 16/28 (2006.01)

(52) U.S. Cl.
CPC ......... *C07K 16/2896* (2013.01); *C07K 16/2803* (2013.01); *C07K 2317/24* (2013.01); *C07K 2317/41* (2013.01); *C07K 2317/524* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 5,595,721 A | 1/1997 | Kaminski et al. | |
| 5,736,137 A | 4/1998 | Anderson et al. | |
| 5,843,398 A | 12/1998 | Kaminski et al. | |
| 6,015,542 A | 1/2000 | Kaminski et al. | |
| 6,090,365 A | 7/2000 | Kaminski et al. | |
| 6,194,551 B1 | 2/2001 | Idusogie et al. | |
| 6,946,292 B2 | 9/2005 | Kanda et al. | |
| 7,166,306 B2 | 1/2007 | Chen et al. | |
| 7,276,585 B2 | 10/2007 | Lazar et al. | |
| 7,462,352 B2 | 12/2008 | Hansen et al. | |
| 7,632,497 B2 | 12/2009 | Stavenhagen | |
| 7,635,472 B2 | 12/2009 | Kufer et al. | |
| 7,968,687 B2 | 6/2011 | McDonagh et al. | |
| 8,323,653 B2 | 12/2012 | Damschroder et al. | |
| 2004/0136908 A1 | 7/2004 | Olson et al. | |
| 2005/0123546 A1 | 6/2005 | Umana et al. | |
| 2006/0134709 A1 | 6/2006 | Stavenhagen et al. | |
| 2006/0257399 A1* | 11/2006 | Gerngross et al. | 424/143.1 |
| 2007/0015239 A1 | 1/2007 | Bihoreau et al. | |
| 2007/0154473 A1 | 7/2007 | Super et al. | |
| 2007/0166306 A1 | 7/2007 | Fey et al. | |
| 2008/0138349 A1* | 6/2008 | Stavenhagen et al. | 424/144.1 |
| 2009/0053240 A1* | 2/2009 | Lazar et al. | 424/172.1 |
| 2009/0098124 A1 | 4/2009 | Stavenhagen | |
| 2009/0136490 A1* | 5/2009 | Pilkington et al. | 424/133.1 |
| 2010/0104509 A1 | 4/2010 | King et al. | |
| 2010/0272723 A1 | 10/2010 | Bernett et al. | |
| 2011/0293609 A1 | 12/2011 | Umaña et al. | |
| 2011/0294984 A1 | 12/2011 | Umana et al. | |

FOREIGN PATENT DOCUMENTS

| | | |
|---|---|---|
| WO | WO 9113974 | 9/1991 |
| WO | WO 9636360 | 11/1996 |
| WO | WO 91/13974 | 9/1997 |
| WO | WO 99/51642 | 10/1999 |
| WO | WO 03/011878 | 2/2003 |

OTHER PUBLICATIONS

Wormald et al. (Biochemistry, 36: 1370-1380, 1997).*
Fernandes (European Biopharmaceutical Review, p. 106-110, summer 2005).*

(Continued)

*Primary Examiner* — Brad Duffy
*Assistant Examiner* — Nelson B Moseley, II
(74) *Attorney, Agent, or Firm* — B. Aaron Schulman, Esq.; Stites & Harbison, PLLC.

(57) ABSTRACT

The present invention relates to an anti-CD19 antibody having a variant Fc region having some specific amino acid modifications relative to a wild-type Fc region which confer one or several useful effector functions. The present invention relates in particular to chimeric, humanized or full human anti-CD19 antibodies comprising such a variant Fc region. It relates advantageously to antibodies with an interesting and valuable glycosylation profile, especially a low fucose level and/or a high oligomannose level and low level of sialic acid, high ADCC function and no CDC. The present invention also relates to the use of these antibodies in the treatment, prevention or management of diseases or disorders, such as cancer, especially a B-cell malignancy and auto-immune disease.

22 Claims, 43 Drawing Sheets

(56) References Cited

OTHER PUBLICATIONS

International Search Report for PCT/EP2011/062271 dated Oct. 13, 2011.
Horton Holly M et al: "Potent in vitro and in vivo activity of an Fc-engineered anti-CD19 monoclonal antibody against lymphoma and leukemia", Cancer Research, vol. 68, No. 19, (Oct. 2008), pp. 8049-8057.
Awan Farrukh T et al: "CD19 targeting of chronic lymphocytic leukemia with a novel Fc-domain-engineered monoclonal antibody", Blood, American Society of Hematology, US, vol. 115, No. 6, (Feb. 1, 2010), pp. 1204-1213.
Pina M Cardarelli et al: "A nonfucosylated human antibody to CD19 with potent B-cell depletive activity for therapy of B-cell malignancies", Cancer Immunology, Immunotherapy, Springer, Berlin, DE, vol. 59, No. 2, (Aug. 6, 2009) pp. 257-265.
Stavenhagen Jeffrey B et al: "Fc optimization of therapeutic antibodies enhances their ability to kill tumor cells in vitro and controls tumor expansion in vivo via low-affinity activating fc gamma receptors", Cancer Research, American Association for Cancer Rerearch, US, vol. 67, No. 18, (Sep. 1, 2007), pp. 8882-8890.
Strohl et al: "Optimization of Fc-mediated effector functions of monoclonal antibodies", Current Opinion in Biotechnology, London, GB, vol. 20, No. 6, (Dec. 1, 2009), pp. 685-691.
Masuda et al: "Enhanced binding affinity for FcgammaRIIIa of fucose-negative antibody is sufficient to induce maximal antibody-dependent cellular cytotoxicity", Molecular Immunology, Pergamon, GB, vol. 44, No. 12, (Apr. 17, 2007), pp. 3122-3131.
Moore Gregory L et al: "Engineered Fc variant antibodies with enhanced ability to recruit complement and mediate effector functions", MABS, vol. 2, No. 2, (Mar. 2010), pp. 181-189.
Beers Stephen A et al: "Antigenic modulation limits the efficacy of anti-CD20 antibodies: implications for antibody selection", Blood, American Society of Hematology, US, vol. 115, No. 25, (Jun. 1, 2010) pp. 5191-5201.
Jassal R et al: "Sialylation of human IgG-Fc carbohydrate by transfected rat alpha2,6-sialyltransferase", Biochemical and Biophysical Research Communications, Academic Press Inc. Orlando, FL, US, vol. 286, No. 2, (Aug. 17, 2001), pp. 243-249.
Lund J et al: "Multiple interactions of IgG with its core oligosaccharide can modulate recognition by complement and human Fc gamma receptor I and influence the synthesis of its oligosaccharide chains", Journal of Immunology, American Association of Immunologists, US, vol. 157, No. 11, (Dec. 1, 1996), pp. 4963-4969.
Winkler, U., et al., "Cytokine-Release Syndrome in Patients with B-Cell Chronic Lymphocytic Leukemia and High Lymphocyte Counts After Treatment with an Anti-CD20 Monoclonal Antibody (Rituximab, IDEC-C2B8)", 1999, 9 pages, vol. 94, Blood.
Weng, Wen-Kai, et al., "Expression of Complement Inhibitors CD46, CD55, and CD59 on Tumor Cells does not Predict Clinical Outcome After Rituximab Treatment in Follicular Non-Hodgkin Lymphoma", 2001, 7 pages, vol. 98, Blood.
Wang, Z., et al., "Universal PCR Amplification of Mouse Immunoglobulin Gene Variable Regions: the Design of Degenerate Primers and an Assessment of the Effect of DNA Polymerase 3' to 5' Exonuclease Activity", 2000, pp. 167-177, vol. 233, Journal of Immunological Methods.
Wang, Siao-Yi, et al., "NK-Cell Activation and Antibody-Dependent Cellular Cytotoxicity Induced by Rituximab-Coated Target Cells is Inhibited by the C3b Component of Complement", 2008, 9 pages, vol. 111, Blood.
Vlasveld, L. T., et al., "Treatment of Low-Grade Non-Hodgkin's Lymphoma with Continuous Infusion of Low-Dose Recombinant Interleukin-2 in Combination with the B-Cell-Specific Monoclonal Antibody CLB-CD19", 1995, pp. 37-47, vol. 40, Cancer Immunol Immunother.
Van Der Kolk, L. E., et al., "Complement Activation Plays a Key Role in the Side-Effects of Rituximab Treatment", Jul. 20, 2001, pp. 807-811, vol. 115, British Journal of Haematology.

Treon, S. P., et al., "Tumor Cell Expression of CD59 is Associated with Resistance to CD20 Serotherapy in Patients with B-Cell Malignancies", 2001, pp. 263-271, vol. 24, No. 3, Journal of Immunotherapy.
Shields, R. L., et al., "Lack of Fucose on Human IgG1 N-Linked Oligosaccharide Improves Binding to Human FcγRIII and Antibody-Dependent Cellular Toxicity", Jul. 26, 2002, pp. 26733-26740, vol. 277, No. 30, The Journal of Biological Chemistry.
Sato, S., et al., "CD10 and CD22 Expression Reciprocally Regulates Tyrosine Phosphorylation of Vav Protein During B Lymphocyte Signaling", Nov. 1997, pp. 13158-13162, vol.
Sarkar, G., et al., "The "Megaprimer" Method of Site-Directed Mutagenesis", 1990, pp. 404-407, vol. 8, No. 4, Research Report, BioTechniques.
Sapra, P., et al., "Internalizing Antibodies are Necessary for Improved Therapeutic Efficacy of Antibody-Targeted Liposomal Drugs", 2002, pp. 7190-7194, vol. 62, Cancer Research.
Sanger, F., et al., "DNA Sequencing with Chain-Terminating Inhibitors (DNA Polymerase/nucleotide Sequences/Bacteriophage øX174)", Dec. 1977, pp. 5463-5467, vol. 74, No. 12, Proc. Natl. Acad. Sci. USA.
Rowland, A. J., et al., "Preclinical Investigation of the Antitumour Effects of Anti-CD19-Idarubicin Immunoconjugates", 1993, pp. 195-202, vol. 37, Cancer Immunol Immunother.
Press, O. W., et al., "Endocytosis and Degradation of Monoclonal Antibodies Targeting Human B-Cell Malignancies", 1989, 8 pages, vol. 49, Cancer Research.
Olejniczak, S. H., et al., "A Quantitative Exploration of Surface Antigen Expression in Common B-Cell Malignancies Using Flow Cytometry", 2006, pp. 93-114, vol. 35, Immunological Investigations.
Nishimura, Y., et al., "Recombinant Human-Mouse Chimeric Monoclonal Antibody Specific for Common Acute Lymphocytic Leukemia Antigen", Feb. 15, 1987, 8 pages, vol. 47, Cancer Research.
Morelle, W., et al., "Analysis of Protein Glycosylation by Mass Spectrometry", 2007, pp. 1585-1602, vol. 2, No. 7, Nature Protocols.
Mølhøj, M., et al., "CD19-/CD3-bispecific Antibody of the BiTE class is far superior to Tandem Diabody with Respect to Redirected Tumor Cell Lysis", 2007, pp. 1935-1943, vol. 44, Molecular Immunology.
Lund, J., et al., "Multiple Interactions of IgG with its Core Oligosaccharide Can Modulate Recognition by Complement and Human Fcγ Receptor I and Influence the Synthesis of its Oligosaccharide Chains", 1996, pp. 4963-4969, vol. 157, The Journal of Immunology.
Lund, J., et al., "A Protein Structural Change in Aglycosylated IgG3 Correlates with Loss of huFcγR1 and huFcγR111 Binding and/or Activation", 1990, pp. 1145-1153, vol. 27, No. 11, Molecular Immunology, Great Britain.
Liu, A. Y., et al., Chimeric Mouse—Human IgG1 Antibody that can Mediate Lysis of Cancer Cells (Immunoglobulin Domain cDNA/DNA Transfection/Tumor Antigen/Complement-Dependent Cytolysis/ Antibody-Dependent Cytolysis/Antibody-Dependent Cellular Cytotoxicity), May 1987, pp. 3439-3443, vol. 84, Proc. Natl. Acad. Sci. USA, Medical Sciences.
Lifely, M. R., et al., "Glycosylation and Biological Activity of CAMPATH-1H Expressed in Different Cell Lines and Grown Under Different Culture Conditions", 1995, pp. 813-822, vol. 5, No. 8, Glycobiology.
Li, Yongli, et al, "Rituximab-CD20 Complexes are Shaved from Z138 Mantle Cell Lymphoma Cells in Intravenous and Subcutaneous SCID Mouse Models", 2007, 10 pages, vol. 179, The Journal of Immunology, http://www.jimmunol.org/content/179/6/4263.
Leatherbarrow, R. J., et al., "The Effect of Aglycosylation on the Binding of Mouse IgG to Staphylococcal Protein A", Dec. 1983, pp. 227-230, vol. 164, No. 2, FEBS 0994, Department of Biochemistry, University of Oxford, Oxford, England.
Kyte, J., "A Simple Method for Displaying the Hydropathic Character of a Protein", 1982, pp. 105-132, vol. 157, J. Mol. Biol.
Kumpel, B. M., "Galactosylation of Human IgG Monoclonal Anti-D Produced by EBV-Transformed B-Lymphoblastoid Cell Lines is

(56) References Cited

OTHER PUBLICATIONS

Dependent of Culture Method and Affects Fc Receptor-Mediated Functional Activity", 1994, pp. 143-151, vol. 5, 3 and 4, Hum. Antibod. Hybridomas.

Kirschfink, Michael, "Targeting Complement in Therapy", 2001, pp. 177-189, vol. 180, Immunological Reviews.

Kabat, E. A., et al., "Identical V Region Amino Acid Sequences and Segments of Sequences in Antibodies of Different Specificities. Relative Contributions of VH and VL Genes, Minigenes, and Complementarity-Determining Regions to Binding of Antibody-Combining Sites", 1991, 12 pages, vol. 147, The Journal of Immunology.

Jenkins, N., et al., "Getting the Glycosylation Right: Implications for the Biotechnology Industry", Aug. 1996, pp. 975-981, vol. 14 Nature Biotechnology.

Hekman, A., et al., "Initial Experience with Treatment of Human B Cell lymphoma with Anti-CD19 Monoclonal Antibody", 1991, pp. 364-372, vol. 32, Cancer Immunology Immunotherapy.

Hallek, M., et al., "Guidelines for the Diagnosis and Treatment of Chronic Lymphocytic Leukemia: A Report from the International Workshop on Chronic Lymphocytic Leukemia Updating the National Cancer Institute-Working Group 1996 Guidelines", Jun. 15, 2008, vol. 111, No. 12, Blood, The American Society of Hematology.

Ripka, J., et al., "Lectin-Resistant CHO Cells: Selection of Four New Pea Lectin-Resistant Phenotypes", 1986, pp. 51-62, vol. 12, No. 1, Somatic Cell and Molecular Genetics.

Essono, S., et al., "A General Method Allowing the Design of Oligonucleotide Primers to Amplify the Variable Regions form Immunoglobulin cDNA", 2003 pp. 251-266, vol. 279, Journal of Immunological Methods.

Ciucanu, I., et al., "A Simple and Rapid Method for the Permethylation of Carbohydrates", 1984, pp. 209-217, vol. 131, Carbohydrate Research.

Cartron, G., et al., "Therapeutic Activity of Humanized Anti-CD20 Monoclonal Antibody and Polymorphism in IgG Fc γRIII Gene", Feb. 1, 2002, 6 pages, vol. 99, No. 3, Blood, The American Society of Hematology.

Bruenke, J., et al., "Effective Lysis of Lymphoma Cells with a Stabilised Bispecific Single-Chain Fv Antibody Against CD19 and Fc γRIII (CD16)", 2005, pp. 218-228, vol. 130, British Journal of Haematology.

Bienvenu, J., et al., "Tumor Necrosis Factor ∝ Release is a Major Biological Event Associated with Rituximab Treatment", 2001, pp. 378-384, vol. 2, The Hematology.

Benedict, C. A., et al., "Determination of the Binding Affinity of an Anti-CD34 Single-Chain Antibody Using a Novel, Flow Cytometry Based Assay", 1997, pp. 223-231, vol. 201, Journal of Immunological.

Bargou, R., et al., "Tumor Regression in Cancer Patients by Very Low Doses of a T Cell-Engaging Antibody", 2008, 5 pages, vol. 321, Science American Association for the Advancement of Science.

Bannerji, R., et al., "Apoptotic-Regulatory and Complement-Protecting Protein Expression in Chronic Lymphocytic Leukemia: Relationship to in Vivo Rituximab Resistance", Apr. 5, 2003, pp. 1466-1471, vol. 21, No. 8, Journal of Clinical Oncology.

Boyd, P.N., et al., "The Effect of the Removal of Sialic Acid, Galactose and Total Carbohydrate on the Functional Activity of Campath-1H", 1995, pp. 1311-1318, vol. 32, No. 17/18, Molecular Immunology.

Umaña, Pablo, et al., "Engineered Glycoforms of an Antineuro-Blastoma IgG1 with Optimized Antibody-Dependent Cellular Cytotoxic Activity", Feb. 1999, pp. 176-180, vol. 17, Nature Biotechnology.

Shinkawa, Toyohide, et al., "The Absence of Fucose but not the Presence of Galactose of Bisecting N-Acetylglucosamine of Human IgG1 Complex-Type Oligosaccharides Shows the Critical Role of Enhancing Antibody-Dependent Cellular Cytotoxicity" Jan. 31, 2003, pp. 3466-3473, vol. 278. No. 5, The Journal of Biological Chemistry.

Yamane-Ohnuki, Naoko, et al., "Establishment of *FUT8I* Knockout Chinese Hamster Ovary Cells: An Ideal Host Cell Line for Producing Completely Defucosylated Antibodies with Enhanced Antibody-Dependent Cellular Cytotoxicity", Sep. 5, 2004, pp. 614-622, vol. 87, No. 5, Biotechnology and Bioengineering.

Radaev, Sergei, et al., "Recognition of IgG by Fcγ Receptor: The Role of Fc Glycosylation and the Binding of Peptide Inhibitors", May 11, 2001, 7 pages, vol. 276, No. 19, The Journal of Biological Chemistry.

Niwa, Rinpei, et al., "Enhanced Natural Killer Cell Binding and Activation by Low-Fucose IgG1 Antibody Results in Potent Antibody-Dependent Cellular Cytotoxicity Induction at lower Antigen Density", Mar. 15, 2005, 11 pages, vol. 11, Clinical Cancer Research.

Mori, K., et al., "Engineering Chinese Hamster Ovary Cells to Maximize Effector Function of Produced Antibodies Using FUT8 siRNA", Dec. 30, 2004, pp. 901-908 vol. 88, No. 7, Biotechnology and Bioengineering.

Lazar, Greg A., et al., "Engineered Antibody Fc Variants with Enhanced Effector Function", Mar. 14, 2006, pp. 4005-4010, vol. 103, No. 11, PNAS, Applied Biological Sciences.

Kumpel, Belinda M., et al., "The Biological Activity of Human Monoclonal IgG anti-D is reduced by β-Galactosidase Treatment", 1995, pp. 82-88, vol. 6 and 3, Hum. Antibod. Hybridomas.

Krapp, S., et al., "Structural Analysis of Human IgG-Fc Glycoforms Reveals a Correlation Between Glycosylation and Structural Integrity", 2003, pp. 979-989, vol. 325, J. Mol. Biol.

Köhler, G., et al., Pillars Article: Continuous Cultures of Fused Cells Secreting Antibody of Predefined Specificity, Aug. 7, 1975, 4 pages, vol. 256, Nature, The Journal of Immunology.

Jefferis, Royston, et al., "A Comparative Study of the N-Linked Oligosaccharide Structures of Human IgG Subclass Proteins", 1990, pp. 529-537, vol. 268, Biochem. J., Great Britain.

Hart, Craig M., et al., "Facilitation of Chromatin Dynamics by SARs", 1998, pp. 519-525, vol. 8, Current Opinion in Genetics & Development.

Liu, A, Y., et al., "Production of a Mouse-Human Chimeric Monoclonal Antibody to CD20 with Potent Fc-Dependent Biologic Activity", Nov. 15, 1987, pp. 3521-3526, vol. 139, No. 10, The Journal of Immunology.

\* cited by examiner

VL-chR005-1
(B) : VL

```
<------------------------------- L-FR1 - IMGT-----------------------------
 D   I   Q   M   T   Q   S   S   A   Y   L   S   V   S   L   G   G   R   V
GAC ATT CAG ATG ACC CAG TCT TCT GCC TAC CTG TCT GTA TCT CTA GGA GGC AGG GTC

-----------------------> ---- L-CDR1 - IMGT --------->  |------------------
 T   I   T   C   K   A   S   D   H   I   N   N   W   L   A   W   Y   Q   H
ACC ATT ACT TGC AAG GCA AGT GAC CAC ATT AAT AAT TGG TTA GCC TGG TAT CAA CAT

---- L-FR2 - IMGT --------------> ---- L-CDR2- IMGT<---  |-----------------
 K   P   G   N   A   P   R   L   L   I   S   G   A   T   T   L   E   T   G
AAA CCA GGA AAT GCT CCT AGG CTC TTA ATA TCT GGT GCA ACC ACT TTG GAA ACT GGG

-----------------> ------------------- L-FR3 - IMGT ----------------------
 V   P   S   R   F   S   G   S   G   S   G   K   D   Y   T   L   S   I   T
GTT CCT TCA AGA TTC AGT GGC AGT GGA TCT GGA AAG GAT TAC ACT CTC AGC ATT ACC

-------------------->  |-------- L-CDR3 - IMGT ---------|
 S   L   Q   T   E   D   V   A   T   Y   Y   C   Q   Q   S   W   N   T   P
AGT CTT CAG ACT GAA GAT GTT GCT ACT TAT TAC TGT CAA CAG TCT TGG AAT ACT CCG

W   T   F   G   G   G   T   K
TGG ACG TTC GGT GGA GGC ACC AAG
```

Figure 4 (continued)

VL-chR005-2
(B) : VL

```
<----------------------------- L-FR1 - IMGT ---------------------------
  D   A   V   M   T   Q   T   P   L   S   L   P   V   S   L   G   D   Q   A
 GAC GCT GTG ATG ACC CAA ACT CCA CTC TCC CTG CCT GTC AGT CTT GGA GAT CAA GCC

------------>    <------------- L-CDR1 - IMGT -----------------<---|
  S   I   S   C   R   S   S   Q   S   L   E   N   S   N   G   N   T   Y   L
 TCC ATC TCT TGC AGG TCT AGT CAG AGC CTT GAA AAC AGT AAT GGA AAC ACC TAT TTG

|-------------- L-FR2 - IMGT --------------->    <--- L-CDR2- IMGT
  N   W   Y   L   Q   K   P   G   Q   S   P   Q   L   L   I   Y   R   V   S
 AAC TGG TAC CTC CAG AAA CCA GGC CAG TCT CCA CAG CTC CTG ATC TAC AGG GTT TCC

---|   <----------------------- L-FR3 - IMGT --------------------------
  N   R   F   S   G   V   L   D   R   F   S   G   S   G   S   G   T   D   F
 AAC CGA TTT TCT GGG GTC CTA GAC AGG TTC AGT GGC AGT GGA TCA GGG ACA GAT TTC

-------------------------->    <----- L-CDR3 - IMGT ------|
  T   L   K   I   S   R   V   E   A   E   D   L   G   V   Y   F   C   L   Q
 ACA CTG AAA ATC AGC AGA GTG GAG GCT GAG GAT TTG GGA GTT TAT TTC TGC CTC CAA

V   T   H   V   P   P   T   F   G   A   G   T   K
 GTT ACA CAT GTC CCT CCC ACG TTC GGT GCT GGG ACC AAG
```

Figure 4 (continued)

Rituximab
        37°C                                                      4°C
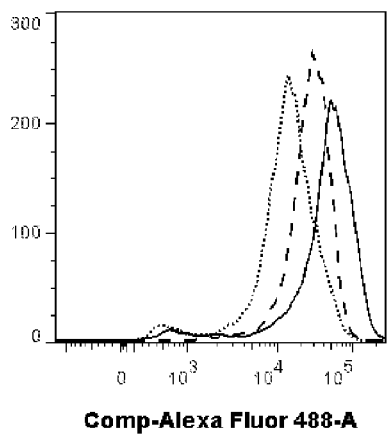 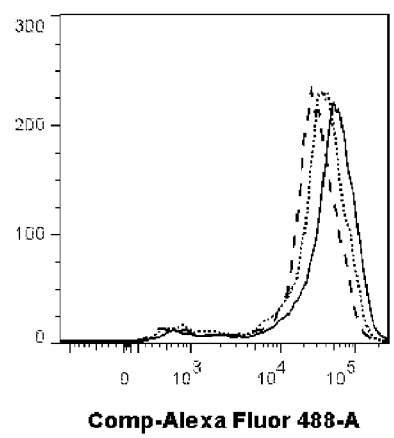
chR005-1 Fc0
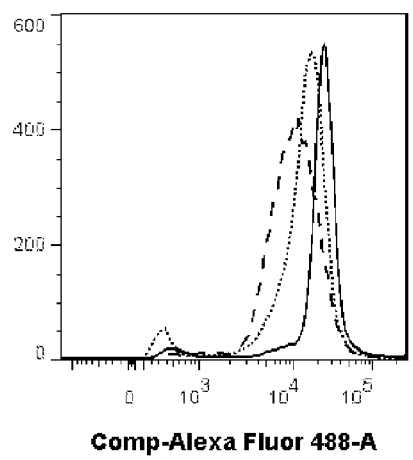 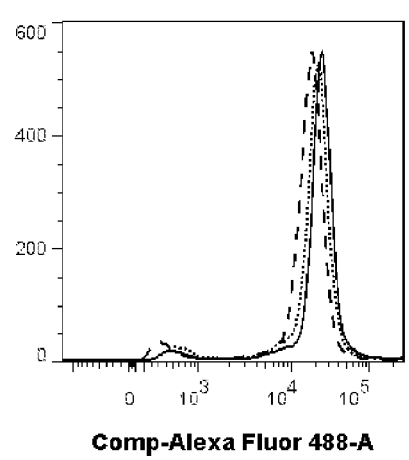
mR005-1
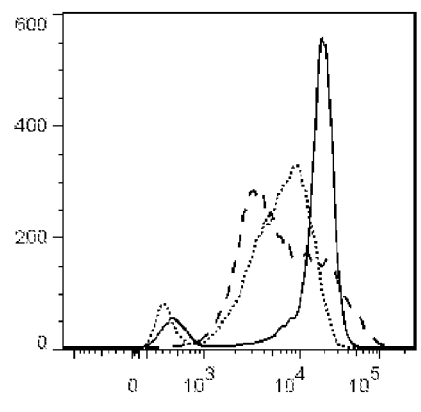 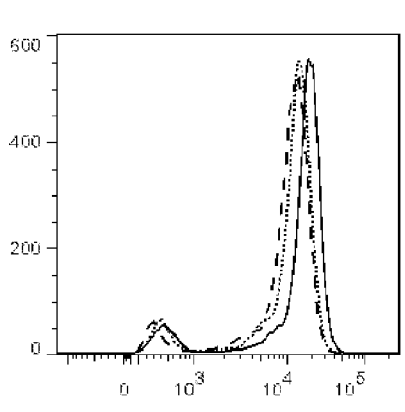
——— T0     ……T3h     ---- T24h
Figure 7

Fc20

| A | S | T | K | G | P | S | V | F | P | L | A | P | S | S | K | S | T | S |
|---|---|---|---|---|---|---|---|---|---|---|---|---|---|---|---|---|---|---|
| gcc | tcc | acc | aag | ggc | cca | tcg | gtc | ttc | ccc | ctg | gca | ccc | tcc | tcc | aag | agc | acc | tct |

| G | G | T | A | A | L | G | C | L | V | K | D | Y | F | P | E | P | V | T |
|---|---|---|---|---|---|---|---|---|---|---|---|---|---|---|---|---|---|---|
| ggg | ggc | aca | gcg | gcc | ctg | ggc | tgc | ctg | gtc | aag | gac | tac | ttc | ccc | gaa | ccg | gtg | acg |

CH1

| V | S | W | N | S | G | A | L | T | S | G | V | H | T | F | P | A | V | L |
|---|---|---|---|---|---|---|---|---|---|---|---|---|---|---|---|---|---|---|
| gtg | tcg | tgg | aac | tca | ggc | gcc | ctg | acc | agc | ggc | gtg | cac | acc | ttc | ccg | gct | gtc | cta |

| Q | S | S | G | L | Y | S | L | S | S | V | V | T | V | P | S | S | S | L |
|---|---|---|---|---|---|---|---|---|---|---|---|---|---|---|---|---|---|---|
| cag | tcc | tca | gga | ctc | tac | tcc | ctc | agc | agc | gtg | gtg | acc | gtg | ccc | tcc | agc | agc | ttg |

| G | T | Q | T | Y | I | C | N | V | N | H | K | P | S | N | T | K | V | D |
|---|---|---|---|---|---|---|---|---|---|---|---|---|---|---|---|---|---|---|
| ggc | acc | cag | acc | tac | atc | tgc | aac | gtg | aat | cac | aag | ccc | agc | aac | acc | aag | gtg | gac |

Hinge

| K | K | V | E | P | K | S | C | D | K | T | H | T | C | P | P | C | P | A |
|---|---|---|---|---|---|---|---|---|---|---|---|---|---|---|---|---|---|---|
| aag | aaa | gtt | gag | ccc | aaa | tct | tgt | gac | aaa | act | cac | aca | tgc | cca | ccg | tgc | cca | gca |

| P | E | L | L | G | G | P | S | V | F | L | L | P | P | K | P | K | D | T |
|---|---|---|---|---|---|---|---|---|---|---|---|---|---|---|---|---|---|---|
| cct | gaa | ctc | ctg | ggg | gga | ccg | tca | gtc | ttc | ctc | tta | ccc | cca | aaa | ccc | aag | gac | acc |

| L | M | I | S | R | T | P | E | V | T | C | V | V | V | D | V | S | H | E |
|---|---|---|---|---|---|---|---|---|---|---|---|---|---|---|---|---|---|---|
| ctc | atg | atc | tcc | cgg | acc | cct | gag | gtc | aca | tgc | gtg | gtg | gtg | gac | gtg | agc | cac | gaa |

Figure 11

| D | P | E | V | K | F | N | W | Y | V | D | G | V | E | V | H | N | A | K |
|---|---|---|---|---|---|---|---|---|---|---|---|---|---|---|---|---|---|---|
| gac | cct | gag | gtc | aag | ttc | aac | tgg | tac | gtg | gac | ggc | gtg | gag | gtg | cat | aat | gcc | aag |

CH2

| T | K | P | P | E | E | Q | Y | N | S | T | L | R | V | V | S | L | T |
|---|---|---|---|---|---|---|---|---|---|---|---|---|---|---|---|---|---|
| aca | aag | ccg | ccg | gag | gag | cag | tac | aac | agc | acg | ctc | cgt | gtg | gtc | agc | ctc | acc |

| V | L | H | Q | D | W | L | N | G | K | E | Y | K | C | K | V | S | N | K |
|---|---|---|---|---|---|---|---|---|---|---|---|---|---|---|---|---|---|---|
| gtc | ctg | cac | cag | gac | tgg | ctg | aat | ggc | aag | gag | tac | aag | tgc | aag | gtc | tcc | aac | aaa |

| A | L | P | A | P | I | E | K | T | I | S | K | A | K | G | Q | P | R | E |
|---|---|---|---|---|---|---|---|---|---|---|---|---|---|---|---|---|---|---|
| gcc | ctc | cca | gcc | ccc | atc | gag | aaa | acc | atc | tcc | aaa | gcc | aaa | ggg | cag | ccc | cga | gaa |

| P | Q | V | Y | T | L | P | P | S | R | D | E | L | T | K | N | Q | V | S |
|---|---|---|---|---|---|---|---|---|---|---|---|---|---|---|---|---|---|---|
| cca | cag | gtg | tac | acc | ctg | ccc | cca | tcc | cgg | gat | gag | ctg | acc | aag | aac | cag | gtc | agc |

CH3

| L | T | C | L | V | K | G | F | Y | P | S | D | I | A | V | E | W | E | S |
|---|---|---|---|---|---|---|---|---|---|---|---|---|---|---|---|---|---|---|
| ctg | acc | tgc | ctg | gtc | aaa | ggc | ttc | tat | ccc | agc | gac | atc | gcc | gtg | gag | tgg | gag | agc |

| N | G | Q | P | E | N | N | Y | K | T | T | P | L | V | L | D | S | D | G |
|---|---|---|---|---|---|---|---|---|---|---|---|---|---|---|---|---|---|---|
| aat | ggg | cag | ccg | gag | aac | aac | tac | aag | acc | acg | cct | ctc | gtg | ctg | gac | tcc | gac | ggc |

| S | F | F | L | Y | S | K | L | T | V | D | K | S | R | W | Q | Q | G | N |
|---|---|---|---|---|---|---|---|---|---|---|---|---|---|---|---|---|---|---|
| tcc | ttc | ttc | ctc | tac | agc | aag | ctc | acc | gtg | gac | aag | agc | agg | tgg | cag | cag | ggg | aac |

| V | F | S | C | S | V | M | H | E | A | L | H | N | H | Y | T | Q | K | S |
|---|---|---|---|---|---|---|---|---|---|---|---|---|---|---|---|---|---|---|
| gtc | ttc | tca | tgc | tcc | gtg | atg | cat | gag | gct | ctg | cac | aac | cac | tac | acg | cag | aag | agc |

Figure 11 (continued)

```
  L   S   L   S   P   G   K   *
 ctc tcc ctg tct ccg ggt aaa tga
```

Figure 11 (continued)

| Masse théorique [M+Na]+ permeth | chR005-1 Fc0 %relatif | chR005-1 Fc20 %relatif | Interprétation |
|---|---|---|---|
| 1375,69 | 0,0 | 0,7 | (Man)₄(GlcNAc)₂ |
| 1416,71 | 3,6 | 3,3 | (GlcNAc)₁ + (Man)₃(GlcNAc)₂ |
| 1579,78 | 0,0 | 27,7 | (Man)₅(GlcNAc)₂ |
| 1590,84 | 1,5 | 6,4 | (GlcNAc)₁ (Fuc)₁ + (Man)₃(GlcNAc)₂ |
| 1620,81 | 4,3 | 4,4 | (GlcNAc)₁ + (Man)₄(GlcNAc)₂ |
| 1661,84 | 0,0 | 1,5 | (GlcNAc)₂ + (Man)₃(GlcNAc)₂ |
| 1783,88 | 0,0 | 6,2 | (Man)₆(GlcNAc)₂ |
| 1794,90 | 0,0 | 2,7 | (Gal)₁ (GlcNAc)₁ (Fuc)₁ + (Man)₃(GlcNAc)₂ |
| 1824,92 | 0,0 | 2,0 | (GlcNAc)₁ (GlcNAc)₁ + (Man)₄(GlcNAc)₂ |
| 1835,93 | 43,6 | 5,4 | (GlcNAc)₂ (Fuc)₁ + (Man)₃(GlcNAc)₂ |
| 1865,94 | 4,2 | 3,8 | (GlcNAc)₂ (Fuc)₁ + (Man)₃(GlcNAc)₂ hypermet ou (Gal)₁ (GlcNAc)₂ + (Man)₃(GlcNAc)₂ |
| 1987,98 | 0,0 | 3,5 | (Man)₇(GlcNAc)₂ |
| 2040,03 | 34,5 | 12,6 | (Gal)₁ (GlcNAc)₂ (Fuc)₁ + (Man)₃(GlcNAc)₂ |
| 2070,04 | 2,4 | 5,3 | (Gal)₁ (GlcNAc)₂ (Fuc)₁ + (Man)₃(GlcNAc)₂ hypermet ou (Gal)₂ (GlcNAc)₂ + (Man)₃(GlcNAc)₂ |
| 2192,08 | 0,0 | 2,7 | (Man)₈(GlcNAc)₂ |
| 2244,12 | 6,1 | 6,2 | (Gal)₂ (GlcNAc)₂ (Fuc)₁ + (Man)₃(GlcNAc)₂ |
| 2396,19 | 0,0 | 1,5 | (Man)₉(GlcNAc)2 |
| 2401,20 | 0 | 1,8 | (Gal)1 (GlcNAc)₂ (Fuc)₁ (NeuAc)₁ + (Man)₃(GlcNAc)₂ |
| 2605,30 | 0 | 2,5 | (Gal)2 (GlcNAc)₂ (Fuc)₁ (NeuAc)₁ + (Man)₃(GlcNAc)₂ |
| 2966,47 | 0,0 | 0,3 | (Gal)2 (GlcNAc)₂ (Fuc)₁ (NeuAc)₂ + (Man)₃(GlcNAc)₂ |

Figure 26

| Theorical Mass [M+Na]⁺ permeth | chR005-1 Fc0 %relatif | chR005-1 Fc18 %relatif | chR005-1 Fc19 %relatif | chR005-1 Fc20 %relatif | chR005-1 Fc28 %relatif | chR005-1 Fc29 %relatif | chR005-1 Fc30 %relatif |
|---|---|---|---|---|---|---|---|
| 1375,69 | 0,0 | 0,0 | 0,0 | 0,6 | 0,0 | 0,0 | 0,0 |
| 1416,71 | 2,7 | 2,1 | 4,3 | 4,0 | 1,4 | 4,8 | 4,1 |
| 1579,78 | 0,0 | 4,5 | 23,4 | 38,7 | 0,0 | 24,6 | 44,5 |
| 1590,84 | 0,8 | 3,0 | 6,6 | 5,4 | 0,7 | 7,1 | 6,4 |
| 1620,81 | 0,7 | 3,2 | 3,5 | 3,0 | 0,0 | 2,9 | 2,7 |
| 1661,84 | 1,4 | 0,0 | 2,0 | 2,3 | 0,0 | 2,3 | 2,1 |
| 1783,88 | 0,0 | 0,0 | 3,0 | 8,0 | 0,0 | 3,4 | 7,3 |
| 1794,90 | 0,0 | 0,0 | 1,6 | 1,5 | 0,0 | 2,1 | 0,8 |
| 1824,92 | 0,0 | 2,0 | 1,8 | 2,6 | 0,0 | 2,0 | 1,9 |
| 1835,93 | 68,2 | 26,8 | 19,3 | 13,6 | 76,6 | 20,9 | 13,9 |
| 1865,94 | 0,0 | 0,0 | 2,6 | 1,9 | 0,0 | 2,6 | 1,9 |
| 1987,98 | 0,0 | 0,0 | 1,0 | 4,4 | 0,0 | 1,0 | 3,0 |
| 2040,03 | 25,0 | 30,5 | 21,7 | 8,1 | 20,5 | 17,6 | 8,6 |
| 2070,04 | 0,0 | 0,0 | 0,0 | 0,0 | 0,0 | 0,0 | 0,0 |
| 2192,08 | 0,0 | 0,0 | 0,5 | 2,3 | 0,0 | 0,6 | 1,5 |
| 2244,12 | 1,2 | 18,6 | 6,1 | 1,7 | 0,8 | 5,2 | 1,3 |
| 2396,19 | 0,0 | 0,0 | 0,0 | 0,4 | 0,0 | 0,0 | 0,0 |
| 2401,20 | 0,0 | 3,4 | 1,8 | 0,5 | 0,0 | 1,8 | 0,0 |
| 2605,30 | 0,0 | 5,3 | 0,7 | 0,3 | 0,0 | 0,7 | 0,0 |
| 2966,47 | 0,0 | 0,7 | 0,0 | 0,0 | 0,0 | 0,0 | 0,0 |

Figure 36

SEQUENCE LISTING

```
<160> NUMBER OF SEQ ID NOS: 34

<210> SEQ ID NO 1
<211> LENGTH: 330
<212> TYPE: PRT
<213> ORGANISM: artificial sequence
<220> FEATURE:
<223> OTHER INFORMATION: Fc20

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Leu Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Pro Glu
```

| | | | | | | | | 165 | | | | 170 | | | | 175 | | |
|---|---|---|---|---|---|---|---|---|---|---|---|---|---|---|---|---|---|---|
Glu Gln Tyr Asn Ser Thr Leu Arg Val Val Ser Leu Leu Thr Val Leu
              180                 185                 190

His Gln Asp Trp Leu Asn Gly Lys Glu Tyr Lys Cys Lys Val Ser Asn
              195                 200                 205

Lys Ala Leu Pro Ala Pro Ile Glu Lys Thr Ile Ser Lys Ala Lys Gly
              210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
              245                 250                 255

Pro Ser Asp Ile Ala Val Glu Trp Glu Ser Asn Gly Gln Pro Glu Asn
              260                 265                 270

Asn Tyr Lys Thr Thr Pro Leu Val Leu Asp Ser Asp Gly Ser Phe Phe
              275                 280                 285

Leu Tyr Ser Lys Leu Thr Val Asp Lys Ser Arg Trp Gln Gln Gly Asn
              290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
              325                 330

<210> SEQ ID NO 2
<211> LENGTH: 993
<212> TYPE: DNA
<213> ORGANISM: artificial sequence
<220> FEATURE:
<223> OTHER INFORMATION: Fc20

<400> SEQUENCE: 2

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtcgtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttacc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgccggagga gcagtacaac     540
agcacgctcc gtgtggtcag cctcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctctcgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa tga                                  993
```

<210> SEQ ID NO 3
<211> LENGTH: 8

```
<212> TYPE: PRT
<213> ORGANISM: artificial sequence
<220> FEATURE:
<223> OTHER INFORMATION: synthetic peptide

<400> SEQUENCE: 3

Gly Tyr Ala Phe Ser Ser Tyr Trp
1               5

<210> SEQ ID NO 4
<211> LENGTH: 8
<212> TYPE: PRT
<213> ORGANISM: artificial sequence
<220> FEATURE:
<223> OTHER INFORMATION: synthetic peptide

<400> SEQUENCE: 4

Ile Tyr Pro Gly Asp Gly Asp Thr
1               5

<210> SEQ ID NO 5
<211> LENGTH: 14
<212> TYPE: PRT
<213> ORGANISM: artificial sequence
<220> FEATURE:
<223> OTHER INFORMATION: synthetic peptide

<400> SEQUENCE: 5

Ala Arg Ser Ile Thr Thr Val Val Gly Cys Ala Met Asp Tyr
1               5                   10

<210> SEQ ID NO 6
<211> LENGTH: 6
<212> TYPE: PRT
<213> ORGANISM: artificial sequence
<220> FEATURE:
<223> OTHER INFORMATION: synthetic peptide

<400> SEQUENCE: 6

Asp His Ile Asn Asn Trp
1               5

<210> SEQ ID NO 7
<211> LENGTH: 3
<212> TYPE: PRT
<213> ORGANISM: artificial sequence
<220> FEATURE:
<223> OTHER INFORMATION: synthetic peptide

<400> SEQUENCE: 7

Gly Ala Thr
1

<210> SEQ ID NO 8
<211> LENGTH: 9
<212> TYPE: PRT
<213> ORGANISM: artificial sequence
<220> FEATURE:
<223> OTHER INFORMATION: synthetic peptide

<400> SEQUENCE: 8

Gln Gln Ser Trp Asn Thr Pro Trp Thr
1               5

<210> SEQ ID NO 9
<211> LENGTH: 5
<212> TYPE: PRT
```

<213> ORGANISM: artificial sequence
<220> FEATURE:
<223> OTHER INFORMATION: synthetic peptide

<400> SEQUENCE: 9

Ser Tyr Trp Val Asn
1               5

<210> SEQ ID NO 10
<211> LENGTH: 17
<212> TYPE: PRT
<213> ORGANISM: artificial sequence
<220> FEATURE:
<223> OTHER INFORMATION: synthetic peptide

<400> SEQUENCE: 10

Gln Ile Tyr Pro Gly Asp Gly Asp Thr Asn Tyr Asn Gly Lys Phe Lys
1               5                   10                  15

Gly

<210> SEQ ID NO 11
<211> LENGTH: 12
<212> TYPE: PRT
<213> ORGANISM: artificial sequence
<220> FEATURE:
<223> OTHER INFORMATION: synthetic peptide

<400> SEQUENCE: 11

Ser Ile Thr Thr Val Val Gly Cys Ala Met Asp Tyr
1               5                   10

<210> SEQ ID NO 12
<211> LENGTH: 11
<212> TYPE: PRT
<213> ORGANISM: artificial sequence
<220> FEATURE:
<223> OTHER INFORMATION: synthetic peptide

<400> SEQUENCE: 12

Lys Ala Ser Asp His Ile Asn Asn Trp Leu Ala
1               5                   10

<210> SEQ ID NO 13
<211> LENGTH: 7
<212> TYPE: PRT
<213> ORGANISM: artificial sequence
<220> FEATURE:
<223> OTHER INFORMATION: synthetic peptide

<400> SEQUENCE: 13

Gly Ala Thr Thr Leu Glu Thr
1               5

<210> SEQ ID NO 14
<211> LENGTH: 4
<212> TYPE: PRT
<213> ORGANISM: artificial sequence
<220> FEATURE:
<223> OTHER INFORMATION: synthetic peptide

<400> SEQUENCE: 14

Ser Ser Tyr Trp
1

<210> SEQ ID NO 15
<211> LENGTH: 8

```
<212> TYPE: PRT
<213> ORGANISM: artificial sequence
<220> FEATURE:
<223> OTHER INFORMATION: synthetic peptide

<400> SEQUENCE: 15

Gly Tyr Thr Phe Thr Ser Tyr Val
1               5

<210> SEQ ID NO 16
<211> LENGTH: 8
<212> TYPE: PRT
<213> ORGANISM: artificial sequence
<220> FEATURE:
<223> OTHER INFORMATION: synthetic peptide

<400> SEQUENCE: 16

Val Asn Pro Tyr Asn Asp Gly Thr
1               5

<210> SEQ ID NO 17
<211> LENGTH: 14
<212> TYPE: PRT
<213> ORGANISM: artificial sequence
<220> FEATURE:
<223> OTHER INFORMATION: synthetic peptide

<400> SEQUENCE: 17

Ala Arg Gly Pro Tyr Tyr Tyr Gly Ser Ser Pro Phe Asp Tyr
1               5                   10

<210> SEQ ID NO 18
<211> LENGTH: 11
<212> TYPE: PRT
<213> ORGANISM: artificial sequence
<220> FEATURE:
<223> OTHER INFORMATION: synthetic peptide

<400> SEQUENCE: 18

Gln Ser Leu Glu Asn Ser Asn Gly Asn Thr Tyr
1               5                   10

<210> SEQ ID NO 19
<211> LENGTH: 3
<212> TYPE: PRT
<213> ORGANISM: artificial sequence
<220> FEATURE:
<223> OTHER INFORMATION: synthetic peptide

<400> SEQUENCE: 19

Arg Val Ser
1

<210> SEQ ID NO 20
<211> LENGTH: 9
<212> TYPE: PRT
<213> ORGANISM: artificial sequence
<220> FEATURE:
<223> OTHER INFORMATION: synthetic peptide

<400> SEQUENCE: 20

Leu Gln Val Thr His Val Pro Pro Thr
1               5

<210> SEQ ID NO 21
<211> LENGTH: 5
<212> TYPE: PRT
```

```
<213> ORGANISM: artificial sequence
<220> FEATURE:
<223> OTHER INFORMATION: synthetic peptide

<400> SEQUENCE: 21

Ser Tyr Val Met His
1               5

<210> SEQ ID NO 22
<211> LENGTH: 17
<212> TYPE: PRT
<213> ORGANISM: artificial sequence
<220> FEATURE:
<223> OTHER INFORMATION: synthetic peptide

<400> SEQUENCE: 22

Tyr Val Asn Pro Tyr Asn Asp Gly Thr Lys Tyr Asn Glu Lys Phe Lys
1               5                   10                  15

Gly

<210> SEQ ID NO 23
<211> LENGTH: 12
<212> TYPE: PRT
<213> ORGANISM: artificial sequence
<220> FEATURE:
<223> OTHER INFORMATION: synthetic peptide

<400> SEQUENCE: 23

Gly Pro Tyr Tyr Tyr Gly Ser Ser Pro Phe Asp Tyr
1               5                   10

<210> SEQ ID NO 24
<211> LENGTH: 16
<212> TYPE: PRT
<213> ORGANISM: artificial sequence
<220> FEATURE:
<223> OTHER INFORMATION: synthetic peptide

<400> SEQUENCE: 24

Arg Ser Ser Gln Ser Leu Glu Asn Ser Asn Gly Asn Thr Tyr Leu Asn
1               5                   10                  15

<210> SEQ ID NO 25
<211> LENGTH: 7
<212> TYPE: PRT
<213> ORGANISM: artificial sequence
<220> FEATURE:
<223> OTHER INFORMATION: synthetic peptide

<400> SEQUENCE: 25

Arg Val Ser Asn Arg Phe Ser
1               5

<210> SEQ ID NO 26
<211> LENGTH: 4
<212> TYPE: PRT
<213> ORGANISM: artificial sequence
<220> FEATURE:
<223> OTHER INFORMATION: synthetic peptide

<400> SEQUENCE: 26

Thr Ser Tyr Val
1

<210> SEQ ID NO 27
<211> LENGTH: 121
```

<212> TYPE: PRT
<213> ORGANISM: artificial sequence
<220> FEATURE:
<223> OTHER INFORMATION: synthetic protein

<400> SEQUENCE: 27

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Val Asn Trp Met Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
    50                  55                  60

Lys Gly Arg Ala Thr Val Thr Ala Asp Lys Ser Ser Ser Thr Ser Tyr
65                  70                  75                  80

Met Gln Phe Ser Ser Leu Thr Ser Glu Asp Ser Ala Val Tyr Phe Cys
                85                  90                  95

Ala Arg Ser Ile Thr Thr Val Val Gly Cys Ala Met Asp Tyr Trp Gly
                100                 105                 110

Gln Gly Thr Ser Val Thr Val Ser Ser
            115                 120

<210> SEQ ID NO 28
<211> LENGTH: 363
<212> TYPE: DNA
<213> ORGANISM: artificial sequence
<220> FEATURE:
<223> OTHER INFORMATION: synthetic DNA

<400> SEQUENCE: 28
caggtccagc tgcagcagtc tggggctgaa ctggtgaggc ctgggtcctc agtgaagatt     60
tcctgtaagg cttctggcta tgcattcagt agctactggg tgaactggat gaagcagagg    120
cctggacagg gacttgagtg gattggacag atttaccctg gagatggtga ctactaattac   180 aatgaaagt tcaagggtcg agccacagtg actgcagaca atcctccag cacatcctac      240 atgcagttca gcagcctaac atctgaggac tctgcggtct attttctgtgc aagatctatt   300 actacggtgg taggctgtgc tatggactac tggggtcaag aacctcggt caccgtctcc     360 tca                                                                  363

<210> SEQ ID NO 29
<211> LENGTH: 103
<212> TYPE: PRT
<213> ORGANISM: artificial sequence
<220> FEATURE:
<223> OTHER INFORMATION: synthetic protein

<400> SEQUENCE: 29

Asp Ile Gln Met Thr Gln Ser Ser Ala Tyr Leu Ser Val Ser Leu Gly
1               5                   10                  15

Gly Arg Val Thr Ile Thr Cys Lys Ala Ser Asp His Ile Asn Asn Trp
                20                  25                  30

Leu Ala Trp Tyr Gln His Lys Pro Gly Asn Ala Pro Arg Leu Leu Ile
            35                  40                  45

Ser Gly Ala Thr Thr Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Ser Trp Asn Thr Pro Trp
                85                  90                  95

Thr Phe Gly Gly Gly Thr Lys
            100

<210> SEQ ID NO 30
<211> LENGTH: 309
<212> TYPE: DNA
<213> ORGANISM: artificial sequence
<220> FEATURE:
<223> OTHER INFORMATION: synthetic DNA

<400> SEQUENCE: 30
gacattcaga tgacccagtc ttctgcctac ctgtctgtat ctctaggagg cagggtcacc    60
attacttgca aggcaagtga ccacattaat aattggttag cctggtatca acataaacca   120
ggaaatgctc ctaggctctt aatatctggt gcaaccactt tggaaactgg ggttccttca   180
agattcagtg gcagtggatc tggaaaggat tacactctca gcattaccag tcttcagact   240
gaagatgttg ctacttatta ctgtcaacag tcttggaata ctccgtggac gttcggtgga   300
ggcaccaag                                                           309

<210> SEQ ID NO 31
<211> LENGTH: 120
<212> TYPE: PRT
<213> ORGANISM: artificial sequence
<220> FEATURE:
<223> OTHER INFORMATION: synthetic protein

<400> SEQUENCE: 31

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Val Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Pro Tyr Tyr Tyr Gly Ser Ser Pro Phe Asp Tyr Trp Gly
            100                 105                 110

Gln Gly Gln Val Thr Val Ser Ser
        115                 120

<210> SEQ ID NO 32
<211> LENGTH: 360
<212> TYPE: DNA
<213> ORGANISM: artificial sequence
<220> FEATURE:
<223> OTHER INFORMATION: synthetic DNA

<400> SEQUENCE: 32
gaggttcagc tgcaacagtc tggacctgag ctggtaaagc ctggggcttc agtgaagatg    60
tcctgcaagg cttctggata cacattcact agctatgtta tgcactgggt gaagcagaag   120
cctgggcagg gccttgagtg gattggatat gttaatcctt acaatgatgg tactaagtac   180

```
aatgagaagt tcaaaggcaa ggccacactg acttcagaca aatcctccag cacagcctac    240
atggagctca gcagcctgac ctctgaggac tctgcggtct attactgtgc aagagggcct    300
tattactacg gtagtagccc ctttgactac tggggccaag gccaggtcac cgtctcctca    360
```

```
<210> SEQ ID NO 33
<211> LENGTH: 108
<212> TYPE: PRT
<213> ORGANISM: artificial sequence
<220> FEATURE:
<223> OTHER INFORMATION: synthetic protein

<400> SEQUENCE: 33

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Pro Thr Phe Gly Ala Gly Thr Lys
            100                 105
```

```
<210> SEQ ID NO 34
<211> LENGTH: 324
<212> TYPE: DNA
<213> ORGANISM: artificial sequence
<220> FEATURE:
<223> OTHER INFORMATION: synthetic DNA

<400> SEQUENCE: 34
gacgctgtga tgacccaaac tccactctcc ctgcctgtca gtcttggaga tcaagcctcc     60
atctcttgca ggtctagtca gagccttgaa aacagtaatg gaaacaccta tttgaactgg    120
tacctccaga aaccaggcca gtctccacag ctcctgatct acagggtttc caaccgattt    180
tctggggtcc tagacaggtt cagtggtagt ggatcaggga cagatttcac actgaaaatc    240
agcagagtgg aggctgagga tttgggagtt tatttctgcc tccaagttac acatgtccct    300
cccacgttcg gtgctgggac caag                                           324
```

ANTI-CD19 ANTIBODY HAVING ADCC FUNCTION WITH IMPROVED GLYCOSYLATION PROFILE

FIELD OF THE INVENTION

The present invention relates to an anti-CD19 antibody having a variant Fc region having some specific amino acid modifications relative to a wild-type Fc region which confer one or several useful effector functions. The present invention relates in particular to chimeric, humanized or full human anti-CD19 antibodies comprising such a variant Fc region. It relates advantageously to antibodies with an interesting and valuable glycosylation profile, especially a low fucose level and/or a high oligomannose level and/or presence of sialic acid, high ADCC function and no CDC. The present invention also relates to the use of these antibodies in the treatment, prevention or management of diseases or disorders, such as cancer, especially a B-cell malignancy and auto-immune disease.

BACKGROUND OF THE INVENTION

In autoimmune and/or inflammatory disorders, the immune system triggers an inflammatory response when there are no foreign substances to fight and the body's normally protective immune system cause damage to its own tissues by mistakenly attacking self. There are many different autoimmune disorders which affect the body in different ways. For example, the brain is affected in individuals with multiple sclerosis, the gut is affected in individuals with Crohn's disease, and the synovium, bone and cartilage of various joints are affected in individuals with rheumatoid arthritis.

B-cell malignancies constitute an important group of cancer that include B-cell non-Hodgkin's lymphoma (NHL), B-cell chronic lymphocytic leukaemia (B-CLL) and hairy cell leukaemia and B-cell acute lymphocytic leukaemia (B-ALL).

Currently, cancer therapy may involve surgery, chemotherapy, hormonal therapy and/or radiation treatment to eradicate neoplastic cells in a patient. Recently, cancer therapy could also involve biological therapy or immunotherapy.

There is a significant need for alternative cancer treatments, particularly for treatment of cancer that has proved refractory to standard cancer treatments, such as surgery, radiation therapy, chemotherapy, and hormonal therapy.

A promising alternative is immunotherapy, in which cancer cells are specifically targeted by cancer antigen-specific antibodies.

Major efforts have been directed at harnessing the specificity of the immune response, for example, hybridoma technology has enabled the development of tumor selective monoclonal antibodies and in the past few years, the Food and Drug Administration has approved the first MAbs for cancer therapy: Rituxan™ (anti-CD20) for non-Hodgkin's Lymphoma and Herceptin™ [anti-(c-erb-2/HER-2)] for metastatic breast cancer.

Rituxan™ (common name is rituximab) is a chimeric mouse-human monoclonal antibody to human CD20, a 35 kilo Daltons, four transmembrane-spanning protein found on the surface of the majority of B-cells in peripheral blood and lymphoid tissue.

The antibody therapy (Rituxan™, U.S. Pat. No. 5,736,137) was approved by the United States Food and Drug Administration (FDA) for the treatment of relapsed or refractory low grade or follicular, CD20-positive B-cell non-Hodgkin's lymphoma.

In addition, lymphoma therapies employing radiolabeled anti-CD20 antibodies have been described in U.S. Pat. Nos. 5,595,721, 5,843,398, 6,015,542, and 6,090,365.

In oncology, Rituxan™/MabThera™ is also indicated in the US for the treatment of relapsed or refractory, low-grade or follicular, CD20-positive, B-cell NHL as a single agent, for the treatment of NHL for previously untreated follicular, CD20-positive, B-cell NHL in combination with cyclophosphamide, vincristine, prednisolone (CVP) chemotherapy for non-progressing (including stable disease), low-grade, CD20 positive, B-cell NHL as a single agent, after first-line CVP chemotherapy and for previously untreated diffuse large B-cell, CD20-positive, NHL in combination with standard chemotherapy (CHOP) or other anthracycline-based chemotherapy regimens.

In oncology, Rituxan™/MabThera™ is indicated in the EU for the treatment of patients with previously untreated or relapsed/refractory chronic lymphocytic leukemia (CLL) in combination with chemotherapy, for the treatment of previously untreated patients with stage III-IV follicular lymphoma in combination with chemotherapy, as maintenance therapy for patients with relapsed/refractory follicular lymphoma responding to induction therapy with chemotherapy with or without Rituxan™/MabThera™, for the treatment of patients with CD20-positive diffuse large B cell non-Hodgkin's lymphoma (NHL) in combination with CHOP (cyclophosphamide, doxorubicin, vincristine, prednisolone) chemotherapy and as monotherapy for treatment of patients with stage III-IV follicular lymphoma who are chemo resistant or are in their second or subsequent relapse after chemotherapy.

In addition, in rheumatology Rituxan™/MabThera™ in combination with methotrexate is indicated for the treatment of adult patients with severe active rheumatoid arthritis who have had an inadequate response or intolerance to other disease-modifying anti-rheumatic drugs (DMARD) including one or more tumor necrosis factor (TNF) inhibitor therapies. MabThera is known as Rituxan™ in the United States, Japan and Canada.

Alemtuzumab is another antibody targeting CD52 that is approved for use in relapsed chronic lymphocytic leukemia (CLL) but is associated with significant toxicity because of the ubiquitous expression of the target antigen on most normal immune cells including T-cells and natural killer (NK) cells.

However, some resistance to rituximab treatment has appeared. Resistance may appear through a variety of mechanisms, some of which lead to loss CD20 expression and resistance to further rituximab treatment. Resistance may appear which may lead to loss or modulation of CD20 expression and is characterized by the lack of efficacy of repeated rituximab treatment or in some cases by the lack of efficacy of primary rituximab treatment. Resistance also occurs in lymphoma cases constitutively lacking CD20 expression, including some B-cell lymphomas such as plasmablastic lymphomas. Moreover, CD20+ patients may not respond to, or acquire resistance to Rituxan® therapy.

Also, under conditions of high B-cell burden, exhaustion of the body's effector mechanisms, for example, NK-cell-mediated killing, may lead to substantial decreases in the immunotherapeutic efficacy of this MAb. Moreover, rituximab treatment of patients with chronic lymphocytic leukemia and high levels of circulating B-cells can lead to removal of CD20 from the cells, thus allowing them to persist and resist clearance.

On the basis of the success and limitations of rituximab and alemtuzumab, in particular resistance and relapse phenomena with rituximab therapy, identification of alternatives antibodies targeting alternative antigens on B-cells is needed.

CD19 is a 95-kDa glycoprotein member of the immunoglobulin (Ig) super family. CD19 is expressed on follicular dendritic cells and all B-cells from their early pre-B-cell stage until the time of plasma cell differentiation. CD19 surface expression is tightly regulated during B-cell development with higher levels seen in more mature cells and CD5+ (B-1) B-cells. CD19 is expressed later than CD20 through the plasmablast stage of B-cell differentiation. Consequently, CD19 expression is relatively high in many pre-B and immature B-lymphoblastic leukemias and B-cell malignancies in which CD20 is poorly expressed. CD19+ plasmablasts may also play a role in the perpetuation of autoimmune diseases.

CD19 is expressed on the surface of B-cells as a multiple molecular complex with CD21, CD81 and CD225. Together with this complex, CD19 is involved in co-signalling with the B-cell receptor and plays a role in the control of differentiation, activation and proliferation of B-lymphoid cells (Sato et al., 1997).

CD19 is present on the blasts of different types of human B-cell malignancies including pro- and pre-B-cell acute lymphoblastic leukaemia (ALL), common ALL (cALL) of children and young adults, NHL, B-CLL and hairy-cell leukaemia (HCL). It is not shed from malignant cells and is internalized after binding of some antibodies (Press et al., 1989). Antigen density ranges from 10 000 to 30 000 molecules per cell on healthy peripheral B-cells, and from 7 000 to 30 000 molecules per cell on malignant cells from a variety of lymphoid cancers (Olejniczak et al., 1983).

CD19 is expressed more broadly and earlier in B-cell development than CD20, which is targeted by Rituxan® and so could have applications in a wider range of cancers including non-Hodgkin's lymphoma and acute lymphoblastic leukaemia as well as CLL.

CD19 has been a focus of immunotherapy development for over 20 years, but initial clinical trials with monoclonal antibodies to CD19 did not result in durable effects despite demonstrating responses in some patients either as a single agent or in combination with other therapeutic agents (Hekman et al., 1991; Vlasved et al., 1995).

Several CD19-specific antibodies have been evaluated for the treatment of B-lineage malignancies in vitro, in mouse models, and in clinical trials. These have included unmodified anti-CD19 antibodies, antibody-drug conjugates, and bispecific antibodies targeting CD19 and CD3 or CD16 to engage cytotoxic lymphocyte effector functions.

The term "monoclonal antibody" as used herein refers to an antibody obtained from a population of substantially homogeneous antibodies, i.e., the individual antibodies comprising the population are identical except for possible naturally occurring mutations or alternative post-translational modifications that may be present in minor amounts, whether produced from hydridomas or recombinant DNA techniques.

Antibodies are proteins, which exhibit binding specificity to a specific antigen. Native antibodies are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly intrachain disulfide bridges.

Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain.

The term 'variable' refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in three segments called complementarily determining regions (CDRs) both in the light chain and the heavy chain variable domains.

The more highly conserved portions of the variable domains are called the framework regions (FR). The variable domains of native heavy and light chains each comprise four FR regions, largely adopting a β-sheet configuration, connected by three CDRs, which form loops connecting, and in some cases forming part of the β-sheet structure. The CDRs in each chain are held together in close proximity by the FR regions and, with the CDRs from the other chain, contribute to the formation of the antigen binding site of antibodies (Kabat et al., 1991).

The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgG, IgD, IgE and IgM, and several of these may be further divided into subclasses (isotypes), e.g. IgG1, IgG2, IgG3 and IgG4; IgA1 and IgA2. The heavy chain constant regions that correspond to the different classes of immunoglobulins are called α, δ, ε, γ, and μ, respectively. Of the various human immunoglobulin classes, only IgG1, IgG2, IgG3 and IgM are known to activate complement.

Immune effector functions which have been shown to contribute to antibody-mediated cytotoxicity include antibody-dependent cell-mediated cytotoxicity (ADCC), antibody-dependent cell-mediated phagocytosis (ADCP), and complement-dependent cytotoxicity (CDC).

Cytotoxicity may also be mediated via anti-proliferative effects. The mechanism of antibody modulation of tumor cell proliferation is poorly understood. However, advances in understanding the interactions of antibodies with Fcγ receptors (FcgR) on immune effector cells have allowed the engineering of antibodies with significantly improved effector function.

The mechanism of action of MAbs is complex and appears to vary for different MAbs. There are multiple mechanisms by which MAbs cause target cell death. These include apoptosis, CDC, ADCC and inhibition of signal transduction.

The most studied is ADCC, which is mediated by natural killer (NK) cells. This involves binding of the Fab portion of an antibody to a specific epitope on a cancer cell and subsequent binding of the Fc portion of the antibody to the Fc receptor on the NK cells. This triggers release of perforin, and granzyme that leads to DNA degradation, induces apoptosis and results in cell death. Among the different receptors for the Fc portion of MAbs, the FcγRIIIa plays a major role in ADCC.

Previous research has shown that a polymorphism of the FcγRIIIa gene encodes for either a phenylalanine (F) or a valine (V) at amino acid 158. Expression of the valine isoform correlates with increased affinity and binding to MAbs (Rowland et al., 1993; Sapra et al., 2002; Molhoj et al., 2007). Some clinical studies have supported this finding, with greater clinical response to rituximab in patients with non-Hodgkin's lymphoma who display the V/V polymorphism (Cartron et al., 2002, Bruenke et al. 2005, Bargou et al., 2008).

WO1999051642 describes a variant human IgG Fc region comprising an amino acid substitution at positions 270 or 329, or at two or more of positions 270, 322, 329, and 331. These modifications aim at increasing the CDC and ADCC effector functions.

WO2002080987 describes a method for treating a B-cell malignancy in a subject comprising administering an anti-CD19 immunotoxin, more particularly a humanized or human, monoclonal antibody. The B-cell malignancy may be one which comprises B-cells that do not express CD20.

WO2007024249 is related to the modification of a human IgG Fc region in order to confer an increase effector cell function mediated by FcγR, especially ADCC. The Fc region comprises specific modifications at various amino acid positions.

WO2008022152 is also related to antibodies that target CD19, wherein the antibodies comprise modifications to Fc receptors and alter the ability of the antibodies to mediate one or more effector functions, including ADCC, ADCP and CDC. ADCC assays are illustrated.

Other patent applications related to anti-CD19 antibodies include WO2009052431, WO2009054863, WO2008031056, WO2007076950, WO2007082715, WO2004106381, WO1996036360, WO1991013974, U.S. Pat. No. 7,462,352, US20070166306 and WO2005092925.

US20090098124 also relates to engineering of antibodies with variant heavy chains containing the Fc region of IgG2, 3 or 4, having one or more amino acid modifications. A number of mutations and group of mutations within the Fc region are proposed. One of them is substitution at position 243 with leucine, at position 292 with proline, at position 300 with leucine, at position 305 with isoleucine, and at position 396 with leucine (MgFc88).

J. B. Stavenhagen et al. (Cancer Res. 2007, 67 (18): 8882-8890) disclose Fc optimization of therapeutic antibodies. The highest levels of ADCC were obtained with mutant 18 (F243L/R292P/Y300L/V305I/P396L). Anti-CD20 and anti-CD32B monoclonal antibodies having this mutated Fc are disclosed.

Despite CD19 is a B-cell specific antigen expressed on chronic lymphocytic leukemia (CLL) cells, to date CD19 has not been effectively targeted with therapeutic monoclonal antibodies. The authors describe XmAb5574, a novel engineered anti-CD19 monoclonal antibody produced by human 293E cells with a modified Fc domain designed to enhance binding of FcγRIIIa. They demonstrate that this antibody mediates potent ADCC, modest direct cytotoxicity and ADCP, but no CDC (Awan et al., 2010).

Moreover, glycoproteins mediate many essential functions in human beings including catalysis, signalling, cell-cell communication and molecular recognition and association. Many glycoproteins have been exploited for therapeutic purposes. The oligosaccharide component of protein can affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. For example, certain oligosaccharide structures mediate rapid clearance of the glycoprotein from the bloodstream through interactions, with specific carbohydrate binding proteins, while others can be bound by antibodies and trigger undesired immune reactions (Jenkins et al., 1996).

Most of the existing therapeutic antibodies that have been licensed and developed as medical agents are of the human IgG1 isotype, the molecular weight of which is ~150 kDa. Human IgG1 is a glycoprotein bearing two N-linked biantennary complex-type oligosaccharides bound to the antibody constant region (Fc), in which the majority of the oligosaccharides are core fucosylated, and it exercises the effector functions of ADCC and CDC through the interaction of the Fc with either leukocyte receptors (FcγRs) or complement.

Recently, therapeutic antibodies have been shown to improve overall survival as well as time to disease progression in a variety of human malignancies, such as breast, colon and haematological cancers, and genetic analysis of FcγR polymorphisms of cancer patients has demonstrated that ADCC is a major antineoplasm mechanism responsible for clinical efficacy. However, the ADCC of existing licensed therapeutic antibodies has been found to be strongly inhibited by serum due to non-specific IgG competing for binding of the therapeutics to FcγRIIIa on natural killer cells, which leads to the requirement of a significant amount of drug and very high costs associated with such therapies.

The enhanced ADCC of non-fucosylated forms of therapeutic antibodies through improved FcγRIIIa binding is shown to be inhibited by the fucosylated counterparts. In fact, non-fucosylated therapeutic antibodies, not including the fucosylated forms, exhibit the strongest and most saturable in vitro and ex vivo ADCC among such antibody variants with improved FcγRIIIa binding as those bearing naturally occurring oligosaccharide heterogeneities and artificial amino acid mutations, even in the presence of plasma IgG.

Inhibiting glycosylation of a human IgG1, by culturing in the presence of tunicamycin, causes, for example, a 50-fold decrease in the affinity of this antibody for the FcγRI receptor present on monocytes and macrophages (Leatherbarrow et al., 1990). Binding to the FcγRIII receptor is also affected by the loss of carbohydrates on IgG, since it has been described that a non-glycosylated IgG3 is incapable of inducing lysis of the ADCC type via the FcγRIII receptor of NK cells (Lund et al., 1995). However, beyond the necessary presence of the glycan-containing residues, it is more precisely the heterogeneity of their structure which may result in differences in the ability to initiate effector functions.

Studies have been conducted to investigate the function of oligosaccharide residue on antibody biological activities. It has been shown that sialic acid of IgG has no effect on ADCC (Boyd et al., 1995). Several reports have shown that Gal residues enhance ADCC (Kumpel et al., 1994). Bisecting GlcNac, which is a beta,4-GlcNac residue transferred to a core beta-mannose (Man) residue, has been implicated in biological residue of therapeutic antibodies (Lifely et al., 1995,) have revealed the effect of fucosylated oligosaccharide on antibody effector functions; the Fuc-deficient IgG1 have shown 50-fold increased binding to FcγRIII and enhanced ADCC.

Today, a wide range of recombinant proteins for therapeutic applications (i.e cancer, inflammatory diseases . . . ) are composed of glycosylated monoclonal antibodies. For therapeutic and economical reasons, there is a large interest in obtaining higher specific antibody activity. One way to obtain large increases in potency, while maintaining a simple production process in cell line and potentially avoiding significant, undesirable side effects, is to enhance the natural, cell-mediated effector functions of MAbs. Consequently, engineering the oligosaccharides of IgGs may yield optimized ADCC which is considered to be a major function of some of the therapeutic antibodies, although antibodies have multiple therapeutic functions (e.g. antigen binding, induction of apoptosis, and CDC).

In general, chimeric and humanized antibodies are prepared using genetic recombination techniques and produced using CHO cells as the host cell. In order to modify the sugar chain structure of the antibodies, various methods have been attempted, say application of an inhibitor against an enzyme relating to the modification of a sugar chain, selection of a CHO cell mutant, or introduction of a gene encoding an enzyme relating to the modification of a sugar chain.

GLYCART BIOTECHNOLOGY AG (Zurich, CH) has expressed N-acetyl-glucosaminyltransferase III (GnTIII) which catalyzes the addition of the bisecting GlcNac residue to the N-linked oligosaccharide, in a Chinese hamster ovary (CHO) cell line, and showed a greater ADCC of IgG1 antibody produced (WO 99/54342; WO 03/011878; WO 2005/044859).

By removing or supplanting fucose from the Fc portion of the antibody, KYOWA HAKKO KOGYO (Tokyo, Japan) has enhanced Fc binding and improved ADCC, and thus the efficacy of the MAb (U.S. Pat. No. 6,946,292).

More recently, Laboratoire Français du Fractionnement et des Biotechnologies (LFB) (France) showed that the ratio Fuc/Gal in MAb oligosaccharide should be equal or lower than 0.6 to get antibodies with a high ADCC (FR 2 861 080).

P. M. Cardarelli et al. (Cancer Immunol. Immunother. 2010, 59:257-265) produce an anti-CD19 antibody in Ms-704PF CHO cells deficient in the FUT8 gene which encodes alpha1,6-fucosyltransferase. Non-fucosylation of the antibody in this paper requires the engineering of an enzymes-deficient cell line. This paper does consider amino acid mutations.

Effector functions such as CDC and ADCC are effector functions that may be important for the clinical efficacy of MAbs. All of these effector functions are mediated by the antibody Fc region and let authors to attempt amino acid modifications with more or less success. Glycosylation, especially fucosylation of the Fc region have a dramatic influence on the efficacy of an antibody. This let the authors to modify the conditions of production of the antibodies in the CHO cells in order to change the glycosylation profile in an attempt here again to improve some effector functions, with more or less success one again.

Complement activation is acknowledged to be a major factor in several systemic inflammatory disorders and autoimmune diseases such as reperfusion injury, rheumatoid arthritis and Guillain Barré Syndrome (Kirschfink et al., 2001). There is also a precedent for involvement of complement in local inflammation generated by antibody-antigen reactions and pain. The complement system consists of serum and membrane bound proteins that interact with each other and with immune cell molecules in a stylized cascade and serves to amplify the original signal. Many complement proteins act as receptor-specific activator molecules.

The role of complement in rituximab therapy remains controversial. Although complement is consumed during rituximab treatment (Van der Kolk et al., 2001) and on some occasions cells remaining or emerging after treatment appear to have been selected to express increased levels of complement defence molecules (Bannerji et al., 2003; Treon et al., 2001). It has also been shown that the expression of complement defense molecules on tumor cells does not predict clinical outcome, and no correlation exists between in vitro complement sensitivity and subsequent therapeutic response (Weng et al., 2001).

Moreover, recent findings indicate that complement activation may indeed be detrimental to the therapeutic activity of rituximab. First, the C3b deposition after rituximab engagement of CLL cells is thought to promote loss of CD20 and thereby therapeutic efficacy through shaving reaction (Li et al., 2007). Second, it has been suggested that deposited C3b may inhibit the interaction between the Fc region of rituximab and CD16 on NK cells, thereby limiting its ability to induce NK activation (Wang et al., 2008).

Thus, complement (inactivated C3b), rather than promoting tumor destruction, could actually impair the therapeutic efficacy of rituximab or of others therapeutic MAbs by promoting loss of CD20 or of others targets and blocking ADCC.

Several side effects encountered during rituximab infusion, including serious ones even leading to death, may eventually be related to CDC activation (Bienvenu 2001, Winkler 1999, Van der Kolk 2001,)

In this context, to facilitate clinical development of the chimeric MAb anti-CD19 in some clinical indication, the inventors selected mutations inducing no complement activation with maximal induction of ADCC.

A method of enhancing the ADCC of the chimeric MAb anti-CD19 MAb 4G7 was disclosed in US 2007/0166306. The MAb 4G7 was produced by using the human mammalian 293T cell line in the presence of a beta (1,4)-N-acetylglucosaminyltransferase III (GnTIII) enzyme, under conditions effective to produce in the antibody, an Fc fragment characterized by Asn297-linked oligosaccharides containing (1) at least 60% N-acetylglucosamine biselecting oligosaccharides and (2) only 10% of non fucosylated N-acetylglucosamine biselecting oligosaccharides.

H. M. Horton et al. (Cancer Res. 2008, 68 (19): 8049-8057) describe an Fc-engineered anti-CD19 antibody, having S239D and I332E mutations. This Fc domain called herein Fc14 was compared to the Fc domain of the invention called chR005-Fc20 (F243L/R292P/Y300L/V305L/P396L). The Fc domain of the invention displays ADCC in the presence of whole blood effector cells whereas no significant ADCC activity was detected with Fc14 in the same conditions in the presence of whole blood containing circulating natural immunoglobulins.

Mammalian cells are the preferred hosts for production of therapeutic glycoproteins, due to their capability to glycosylate proteins in the most compatible form for human applications (Jenkis et al., 1996). Bacteria very rarely glycosylates proteins, and like other type of common hosts, such as yeasts, filamentous fungi, insect and plant cells yield glycosylation patterns associated with rapid clearance from the blood stream.

Among mammalian cells, Chinese hamster ovary (CHO) cells have been most commonly used during the last two decades. In addition to giving suitable glycosylation patterns, these cells allow consistent generation of genetically stable, highly productive clonal cell lines. They can be cultured to high densities in simple bioreactors using serum-free media, and permit the development of safe and reproducible bioprocesses. Other commonly used animal cells include baby hamster kidney (BHK) cells, NSO- and SP2/0-mouse myeloma cells. Production from transgenic animals has also been tested (Jenkins et al., 1996).

Since the sugar chain structure plays a remarkably important role in the effector function of antibodies and differences are observed in the sugar chain structure of glycoproteins expressed by host cells, development of a host cell which can be used for the production of an antibody having higher effector function has been an objective.

In order to modify the sugar chain structure of the produced glycoprotein, various methods have been attempted, such as (1) application of an inhibitor against an enzyme relating to the modification of a sugar chain, (2) selection of a cell mutant, (3) introduction of a gene encoding an enzyme relating to the modification of a sugar chain, and the like. Specific examples are described below.

Examples of an inhibitor against an enzyme relating to the modification of a sugar chain includes tunicamycin which selectively inhibits formation of GlcNAc-P-P-Dol which is the first step of the formation of a core oligosaccharide which is a precursor of an N-glycoside-linked sugar chain, castanospermin and W-methyl-1-deoxynojirimycin which are inhibitors of glycosidase I, bromocondulitol which is an inhibitor of glycosidase II, 1-deoxynojirimycin and 1,4-dioxy-1,4-imino-D-mannitol which are inhibitors of mannosidase I, swainsonine which is an inhibitor of mannosidase II, swainsonine which is an inhibitor of mannosidase II and the like. Examples of an inhibitor specific for a glycosyltransferase include deoxy derivatives of substrates against N-acetylglucosamine transferase V (GnTV) and the like. Also it is known that 1-deoxynojirimycin inhibits synthesis of a complex type sugar chain and increases the ratio of high mannose type and hybrid type sugar chains (Glycobiology series 2—Destiny of Sugar Chain in Cell, edited by Katsutaka Nagai, Senichiro Hakomori and Akira Kobata, 1993).

Cell mutants regarding the activity of an enzyme relating to the modification of a sugar chain are mainly selected and obtained as a lectin-resistant cell line. For example, CHO cell mutants having various sugar chain structures have been obtained as a lectin-resistant cell line using a lectin such as WGA (wheat-germ agglutinin derived from *T. vulgaris*), ConA (cocanavalin A derived from *C. ensiformis*), RIC (a toxin derived from *R. communis*), L-PHA (leucoagglutinin derived from *P. vulgaris*), LCA (lentil agglutinin derived from *L. culinaris*), PSA (pea lectin derived from *P. sativum*) or the like (Genet et al., 1986).

As an example of the modification of the sugar chain structure of a product obtained by introducing the gene of an enzyme relating to the modification of a sugar chain, into a host cell, it has been reported that a protein in which a number of sialic acid is added to the non-reducing end of the sugar chain can be produced by introducing rat β-galactosidase-a-5,6-sialyltransferase into CHO cell. Different types of glycoprotein-modifying glycosyl transferase may be also expressed in the host system such as GnT III, or, alternatively, b (1,4)-N-acetylglucosaminyltransferase V (GnT V), β(1,4)-galactosyl transferase (GalT) and mannosidase II (Man II).

WO20070166306 is related to the use of avian embryonic derived stem cell lines, named EBx®, for the production of proteins and more specifically glycoproteins such as antibodies that are less fucosylated than with usual CHO cells.

Ramesh Jassal et al. generate sialylation of anti NIP IgG3 antibody with FA243 mutation or by using a rat α2,6-sialyltransferase transfected CHO-K1 cell line. The FA243 IgG3 having both α2,6 and α2,3 silaylation restored target cell lysis by complement.

John Lund et al. (Journal of Immunology, 1996, vol. 157, no. 11, pp 4963-4969) describe that aglycosylated human chimeric IgG3 retained a significant capacity to bind human C1q and trigger lysis mediated through guinea pig C.

The present inventors have evaluated the glycosylation profile of various Fc chimeric variant antibodies of human IgG1 subclass directed against the CD19 antigen produced by the Chinese hamster ovary cells CHO DG44 cell, (purchased by ECACC) unmodified and untreated with glycosylation inhibitors. By analyzing and comparing structures of the sugar chains of the chR005-1 Fc0 and the optimized chR005-1 Fc20 variant antibodies produced, the present invention provides that a wild-type CHO host cell without any engineering expresses an interesting and valuable glycosylation profile, especially a low fucose level and/or a high oligomannose level and/or presence of sialic acid following Fc20 amino acid mutation.

SUMMARY OF THE INVENTION

The present invention provides chimeric, humanized, human, bispecific and drug conjugated anti-CD19 antibodies, anti-CD19 antibody fusion proteins, and fragments thereof that bind a human B-cell marker.

Current approaches to optimize therapeutic antibody functionality (e.g. ADCC, CDC) have focused on amino acid modification or modification of the glycosylation state of the native Fc region. In contrast the present invention is based on a simultaneous combined approach concerning amino acid modification and glycosylation modification.

The present invention relates to the field of glycosylation engineering of proteins. More particular, the present invention is directed to the glycosylation engineering of proteins by using a wild-type mammalian CHO cell line to provide variant proteins following amino acid mutation with improved therapeutic properties such as efficient ADCC whereas the parent molecules (murine or wild-type chimeric antibodies) do not detectably exhibit this function.

The molecules of the invention still conserved apoptotic effector function conferred by the parental murine antibody.

More particularly, the present innovation relates to modifications of antibody functionality in immunoglobulin with Fc regions from IgG1 isotype to have no capability to trigger CDC effector function.

More particularly the molecules of the invention exhibit no complement activation and exhibit efficient induction of ADCC.

The molecules of the invention are particularly useful for the treatment of B-cell disorders, such as but not limited to, B-cell malignancies, for the treatment and prevention of autoimmune disease, and for the treatment and prevention of graft-versus host diseases (GVHD), humoral rejection, and post-transplantation lymphoproliferative disorder in human transplant recipients, for patients refractory to treatment with exiting therapeutic antibody such as but not limited as anti-CD20 antibody or for combination treatment with existing therapeutic antibody such as but not limited to anti-CD20 antibodies.

The inventors have very surprisingly found that amino acid modifications at positions 243, 292, 300, 305 and 396 in the Fc region of an anti-CD19 antibody may have consequences not only on the effector functions, including ADCC (strong ADCC) and CDC (no CDC), but also directly on the glycosylation profile of the antibody, with the antibody being produced or expressed in mammal cells, including wild-type mammal cells, in particular rodent cells, especially CHO cells, such as the wild-type DG44 CHO cells (ATCC).

DETAILED DESCRIPTION OF THE INVENTION

A first object of the present invention is an anti-CD19 antibody modified to comprise a variant human IgG Fc region, wherein this variant region comprises an amino acid substitution at each of the amino acid positions 243, 292, 300, 305 and 396 of the human IgG Fc region. The amino acid residues in the Fc region are numbered according to the numbering system of Kabat®. The antibody according to the invention does not comprise an amino acid substitution at the position 326 or at both positions 326 and 333.

The recombinant anti-CD19 antibodies according to the invention have an interesting glycosylation profile after production in a wild-type mammal cell, especially rodent cell, such as in particular a wild-type CHO.

In particular, from the transfected cells, e.g. wild-type CHO, the invention allows to express a large proportion of recombinant antibodies or fragment thereof, carrying a common N-linked oligosaccharide structure of a biantennary-type that comprises long chains with terminal GlcNac that are galactosylated and non-fucosylated.

One or more glycoforms are present in a recombinant anti-CD19 antibody population or pool. A glycoform is an isoform of a protein that differs only with respect to the number or type of attached glycans.

In a very surprising and valuable embodiment, the antibodies have a low fucose level. This means that among a recombinant anti-CD19 antibody population produced in these cells, e.g. wild-type CHO, in this embodiment, the proportion of non-fucosylated antibodies represent approximately at least 40%, preferably approximately at least 60%, more preferably approximately at least 80% of the antibodies or higher, e.g. at least 85%. More particularly, the non-fucosylation concerns the Fc.

As CHO cells, mentioned may be done of CHO dhfr−/−, CHO/DG44 and CHO Easy C.

A specific object of the invention is an anti-CD19 antibody modified to comprise a variant human IgG Fc region, preferably IgG1 Fc region, wherein this variant region comprises an amino acid substitution at each of the amino acid positions 243, 292, 300, 305 and 396 of the human IgG Fc region, with the proviso that position 326 or 333 or both positions 326 and 333 are not substituted, wherein the numbering of the amino acid residues in the Fc region is the one of Kabat, and wherein the antibody has been produced in wild-type rodent cells, preferably wild-type CHO cells. According to a preferred feature, this antibody has a low level of fucose. In accordance with the invention, low level of fucose means either (1) a reduced amount of fucose in one antibody, especially in its Fc or (2) a high number of antibodies in a pool that have reduced amount of fucose and/or no fucose, especially in their Fc.

In the present description, one speaks about an Fc or the two Fc of an antibody according to the invention. Even if not mentioned every time, there is for every embodiment a preferred case where the antibody has two Fc and each one of the Fc has a similar structure (the same mutations) and a similar glycosylation profile.

In an embodiment, the antibody of the invention has an Fc, preferably two Fc bearing no $(GlcNAc)_2(Fuc)_1+(Man)_3(GlcNAc)_2$ glycan.

In an embodiment, the antibody of the invention has an Fc, preferably two Fc bearing no $(Gal)_1(GlcNAc)_2(Fuc)_1+(Man)_3(GlcNAc)_2$ glycan.

In an embodiment, the antibody of the invention has an Fc, preferably two Fc bearing no $(GlcNAc)_2(Fuc)_1+(Man)_3(GlcNAc)_2$ glycan and no $(Gal)_1(GlcNAc)_2(Fuc)_1+(Man)_3(GlcNAc)_2$ glycan.

In an embodiment, the antibody of the invention comprises a $(Man)_5(GlcNAc)_2$ glycan. In an embodiment, the antibody of the invention comprises a $(Man)_5(GlcNAc)_2$ glycan and has no $(GlcNAc)_2(Fuc)_1+(Man)_3(GlcNAc)_2$ glycan and/or, preferably and, no $(Gal)_1(GlcNAc)_2(Fuc)_1+(Man)_3(GlcNAc)_2$ glycan.

In an embodiment, the antibody comprises an Fc, preferably two Fc bearing one and/or two of the following glycans:
$(Gal)_1(GlcNAc)_2 (Fuc)_1 (NeuAc)_1+(Man)_3(GlcNAc)_2$
$(Gal)_2(GlcNAc)_2 (Fuc)_1 (NeuAc)_1+(Man)_3(GlcNAc)_2$.

In an embodiment, the antibody of the invention comprises an Fc, preferably two Fc bearing a $(Man)_5(GlcNAc)_2$ glycan and has no $(GlcNAc)_2(Fuc)_1+(Man)_3(GlcNAc)_2$ glycan and/or, preferably and, no $(Gal)_1(GlcNAc)_2(Fuc)_1+(Man)_3(GlcNAc)_2$ glycan, and comprises one and/or two of the following glycans:
$(Gal)_1(GlcNAc)_2 (Fuc)_1 (NeuAc)_1+(Man)_3(GlcNAc)_2$
$(Gal)_2(GlcNAc)_2 (Fuc)_1 (NeuAc)_1+(Man)_3(GlcNAc)_2$.

Another object of the invention is an anti-CD19 antibody modified to comprise a variant human IgG Fc region, preferably IgG1 Fc region, wherein this variant region comprises an amino acid substitution at each of the amino acid positions 243, 292, 300, 305 and 396 of the human IgG Fc region, with the proviso that position 326 or 333 or both positions 326 and 333 are not substituted, wherein the numbering of the amino acid residues in the Fc region is the one of Kabat, and wherein the antibody has an Fc, preferably two Fc bearing no $(GlcNAc)_2(Fuc)_1+(Man)_3(GlcNAc)_2$ glycan and/or, preferably and, no $(Gal)_1(GlcNAc)_2(Fuc)_1+(Man)_3(GlcNAc)_2$ glycan. In an embodiment, the antibody of the invention comprises a $(Man)_5(GlcNAc)_2$ glycan. In an embodiment, the antibody comprises an Fc, preferably two Fc bearing one or two of the following glycans:
$(Gal)_1(GlcNAc)_2 (Fuc)_1 (NeuAc)_1+(Man)_3(GlcNAc)_2$
$(Gal)_2(GlcNAc)_2 (Fuc)_1 (NeuAc)_1+(Man)_3(GlcNAc)_2$.

In still a very surprising and valuable embodiment, the antibodies have a high oligomannose level. This means that among a recombinant anti-CD19 antibody population produced in these cells, e.g. wild-type CHO the proportion of antibodies featured by a higher level of oligomannoses represent approximately at least 20%, preferably approximately at least 30%, more preferably approximately at least 40%, still more preferably approximately at least 50% of the antibodies or higher.

In still a very surprising and valuable embodiment, among a recombinant antibody population produced in these cells, e.g. wild-type CHO, the proportion of antibodies featured by a higher level of sialylated glycoforms represent approximately at least 1.5%, preferably approximately at least 2.5%, more preferably approximately at least 5% of the antibodies or higher.

The present invention has also as an object a pool of antibodies (or composition or population of antibodies) according to the invention, wherein it comprises anti-CD19 antibodies modified to comprise a variant human IgG Fc region, preferably IgG1 Fc region, wherein this variant region comprises an amino acid substitution at each of the amino acid positions 243, 292, 300, 305 and 396 of the human IgG Fc region, with the proviso that position 326 or 333 or both positions 326 and 333 are not substituted, wherein the numbering of the amino acid residues in the Fc region is the one of Kabat. According to a feature, the antibody pool has been produced in wild-type rodent cells, preferably wild-type CHO cells. According to another feature, the antibody pool has a low level of fucose.

In a first embodiment, this pool comprises less or equal than 20%, preferably 15% of such anti-CD19 antibodies comprising an Fc, preferably two Fc having a $(GlcNAc)_2(Fuc)_1+(Man)_3(GlcNAc)_2$ glycan and/or, preferably and, less or equal than 20%, preferably 15% of such antibodies comprising an Fc, preferably two Fc having a $(Gal)_1(GlcNAc)_2(Fuc)_1+(Man)_3(GlcNAc)_2$ glycan. Glycoform percentages are expressed in % number.

In another embodiment, the pool of antibodies comprises at least 20, 25, 30, 40 or 50% of antibodies comprising an Fc, preferably two Fc having $(Man)_5(GlcNAc)_2$ glycans. In an embodiment, the value is at least 30%.

In another embodiment, the pool comprises less or equal than 20%, preferably 15% of such anti-CD19 antibodies comprising an Fc, preferably two Fc having a $(GlcNAc)_2(Fuc)_1+(Man)_3(GlcNAc)_2$ glycan and/or, preferably and, less or equal than 20%, preferably 15% of such antibodies comprising an Fc, preferably two Fc having a $(Gal)_1(GlcNAc)_2(Fuc)_1+(Man)_3(GlcNAc)_2$ glycan, and at least 20, 25, 30, 40 or 50% of antibodies comprising an Fc, preferably two Fc having $(Man)_5(GlcNAc)_2$ glycans. In a preferred embodiment the pool of antibodies comprises all these features. In an embodiment, the value for oligomannose is at least 30%.

In another embodiment, the pool of antibodies comprises
less than 2, 1.5, 1 or 0.8% of antibodies comprising an Fc, preferably two Fc having $(Gal)_1(GlcNAc)_2(Fuc)_1(NeuAc)_1+(Man)_3(GlcNAc)_2$; (typical range 0.1-2)

and/or, preferably, less than 3, 2, 1 or 0.5% of antibodies comprising an Fc, preferably two Fc having $(Gal)_2(GlcNAc)_2(Fuc)_1(NeuAc)_1+(Man)_3(GlcNAc)_2$ (typical range 0.1-3)

In still another embodiment, the pool comprises less or equal than 20%, preferably 15% of such anti-CD19 antibodies comprising an Fc, preferably two Fc having a $(GlcNAc)_2(Fuc)_1+(Man)_3(GlcNAc)_2$ glycan and/or, preferably and, less or equal than 20%, preferably 15% of such antibodies comprising an Fc, preferably two Fc having a $(Gal)_1(GlcNAc)_2(Fuc)_1+(Man)_3(GlcNAc)_2$ glycan, and at least 20, 25, 30, 40 or 50% of antibodies comprising an Fc, preferably two Fc having $(Man)_5(GlcNAc)_2$ glycans, and further less than 2, 1.5, 1 or 0.8% of antibodies comprising an Fc, preferably two Fc having $(Gal)_1(GlcNAc)_2(Fuc)_1(NeuAc)_1+(Man)_3(GlcNAc)_2$ and/or, preferably and, less than 3, 2, 1 or 0.5% of antibodies comprising an Fc, preferably two Fc having $(Gal)_2(GlcNAc)_2$ $(Fuc)_1(NeuAc)_1+(Man)_3(GlcNAc)_2$. In a preferred embodiment the pool of antibodies comprises all these features. In an embodiment, the value for oligomannose is at least 30%.

Another object of the invention is a pool of antibodies (or composition of antibodies) according to the invention, wherein it comprises anti-CD19 antibodies modified to comprise a variant human IgG Fc region, preferably IgG1 Fc region, wherein this variant region comprises an amino acid substitution at each of the amino acid positions 243, 292, 300, 305 and 396 of the human IgG Fc region, with the proviso that position 326 or 333 or both positions 326 and 333 are not substituted, wherein the numbering of the amino acid residues in the Fc region is the one of Kabat, and wherein the pool comprises less or equal than 20%, preferably 15% of such anti-CD19 antibodies comprising an Fc, preferably two Fc having a $(GlcNAc)_2(Fuc)_1+(Man)_3(GlcNAc)_2$ glycan and/or, preferably and, less or equal than 20%, preferably 15% of such antibodies comprising an Fc, preferably two Fc having a $(Gal)_1(GlcNAc)_2(Fuc)_1+(Man)_3(GlcNAc)_2$glycan.

In another embodiment, the pool of antibodies comprises at least 20, 25, 30, 40 or 50% of antibodies comprising an Fc, preferably two Fc having $(Man)_5(GlcNAc)_2$ glycans. In an embodiment, the value is at least 30%.

In another embodiment, the pool comprises less or equal than 20%, preferably 15% of such anti-CD19 antibodies comprising an Fc, preferably two Fc having a $(GlcNAc)_2(Fuc)_1+(Man)_3(GlcNAc)_2$ glycan and/or, preferably and, less or equal than 20%, preferably 15% of such antibodies comprising an Fc, preferably two Fc having a $(Gal)_1(GlcNAc)_2(Fuc)_1+(Man)_3(GlcNAc)_2$ glycan, and at least 20, 25, 30, 40 or 50% of antibodies comprising an Fc, preferably two Fc having $(Man)_5(GlcNAc)_2$ glycans. In a preferred embodiment the pool of antibodies comprises all these features. In an embodiment, the value for oligomannose is at least 30%.

In another embodiment, the pool of antibodies comprises
less than 2, 1.5, 1 or 0.8% of antibodies comprising an Fc, preferably two Fc having $(Gal)_1(GlcNAc)_2(Fuc)_1(NeuAc)_1+(Man)_3(GlcNAc)_2$ and/or, preferably, less than 3, 2, 1 or 0.5% of antibodies comprising an Fc, preferably two Fc having $(Gal)_2(GlcNAc)_2(Fuc)_1(NeuAc)_1+(Man)_3(GlcNAc)_2$.

In still another embodiment, the pool comprises less or equal than 20%, preferably 15% of such anti-CD19 antibodies comprising a $(GlcNAc)_2(Fuc)_1+(Man)_3(GlcNAc)_2$ glycan and/or, preferably and, less or equal than 20%, preferably 15% of such antibodies comprising an Fc, preferably two Fc having a $(Gal)_1(GlcNAc)_2$ $(Fuc)_1+(Man)_3(GlcNAc)_2$ glycan, and at least 20, 25, 30, 40 or 50% of antibodies comprising an Fc, preferably two Fc having $(Man)_5(GlcNAc)_2$ glycans, and further less than 2, 1.5, 1 or 0.8% of antibodies comprising an Fc, preferably two Fc having $(Gal)_1(GlcNAc)_2(Fuc)_1(NeuAc)_1+(Man)_3(GlcNAc)_2$ and/or, preferably and, less than 3, 2, 1 or 0.5% of antibodies comprising an Fc, preferably two Fc having $(Gal)_2(GlcNAc)_2$ $(Fuc)_1(NeuAc)_1+(Man)_3(GlcNAc)_2$. In a preferred embodiment the pool of antibodies comprises all these features. In an embodiment, the value for oligomannose is at least 30%.

In a preferred embodiment, the antibodies of the invention combine three of these features, especially low fucose level and high oligomannose level and/or presence of sialic acid.

In particular, the transfected cells of the invention, e.g. wild-type CHO cells allow to express a large proportion of antibodies or fragment thereof, carrying a common N-linked oligosaccharide structure of a biantennary-type that comprises long chains with terminal GlcNac that are galactosylated and non-fucosylated and which confer strong ADCC activity to antibodies.

In an embodiment, the anti-CD19 antibody having a specific glycosylation profile according to the invention, especially a low fucose level and/or a high oligomannose level and/or presence of sialic acid is produced or expressed, or is as produced or expressed, in mammal cells, preferably wild-type mammal cells.

In an embodiment, the cells are rodent cells, in particular CHO cells.

In an embodiment, the cells are wild-type rodent cells, especially wild-type CHO cells.

In an embodiment, this antibody is able to generate ADCC activity.

In an embodiment, it is able to generate no CDC.

In an embodiment, this antibody is able to generate ADCC activity, no CDC and has an interesting and valuable glycosylation profile, especially a low fucose level and/or a high oligomannose level and/or presence of sialic acid.

The Fc region may comprise other amino acid mutations (substitution, addition or deletion) with the proviso that position 326 or 333 is not mutated or positions 326 and 333 are not simultaneously mutated. By definition, the invention encompasses mutations in the Fc region which are able to confer to the antibody made with this Fc region, the ADCC and glycosylation profile according to the invention, and no CDC.

The human IgG Fc region may be a region of IgG sub-class. It may be an Fc region of IgG1, IgG2, IgG3 or IgG4. In an embodiment, the Fc region is an IgG1 Fc region.

The amino acids of the Fc region that are substituted in accordance with the invention may be substituted by any amino acid, the condition being that the whole set of substituted amino acids is able to generate this ADCC activity and/or to confer an interesting and valuable glycosylation profile, especially a low fucose level and/or a high oligomannose level and/or presence of sialic acid according to the invention. Examples of possible substitutions are given thereafter.

In an embodiment, Phe243 is substituted by Leu.
In an embodiment, Arg292 is substituted by Pro.
In an embodiment, Tyr300 is substituted by Leu.
In an embodiment, Val305 is substituted by Leu.
In an embodiment, Pro396 is substituted by Leu.

In an embodiment, the antibody comprises an Fc comprising substitution at position 243 with Leucine (L), at position 292 with Proline (P), at position 300 with Leucine (L), at position 305 with Leucine (L) and at position 396 with Leucine.

In an embodiment, the antibody comprises an Fc region in which Phe243 is substituted by Leu, Arg292 is substituted by Pro, Tyr300 is substituted by Leu, Val305 is substituted by Leu, and Pro396 is substituted by Leu.

In an embodiment, this Fc region has the amino acid sequence depicted on SEQ ID NO: 1 (Fc20, FIG. 11). Nucleic acid sequence is SEQ ID NO: 2.

Modifications and changes may be made in the structure of a polypeptide of the present invention and still obtain a molecule having like characteristics. For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art (Kyte et al. 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics.

It is believed that the relative hydropathic character of the amino acid determines the secondary structure of the resultant polypeptide, which in turn defines the interaction of the polypeptide with other molecules, for example, enzymes, substrates, receptors, antibodies, antigens, and the like. It is known in the art that an amino acid may be substituted by another amino acid having a similar hydropathic index and still obtain a biologically functionally equivalent polypeptide. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biologically functionally equivalent peptide or polypeptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlate with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophility value and still obtain a biologically equivalent, and in particular, an immunologically equivalent, polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like.

| Amino Acid | Index |
|---|---|
| isoleucine L | (+4.5) |
| valine V | (+4.2) |
| leucine L | (+3.8) |
| phenylalanine | (+2.8) |
| cysteine C | (+2.5) |
| methionine M | (+1.9) |
| alanine A | (+1.8) |
| glycine G | (−0.4) |
| threonine T | (−0.7) |
| serine S | (−0.8) |
| tryptophan W | (−0.9) |
| tyrosine Y | (−1.3) |
| proline P | (−1.6) |
| histidine H | (−3.2) |
| glutamate E | (−3.5) |
| glutamine Q | (−3.5) |
| aspartate D | (−3.5) |
| asparagine N | (−3.5) |
| lysine K | (−3.9) |
| arginine R | (−4.5) |

Amino acid substitution may be chosen or selected differently. Possible substitutions have been documented in WO99/51642, WO2007024249 and WO2007106707.

In an embodiment, Phe243 is substituted by an amino acid chosen among Leu, Trp, Tyr, Arg and Gln. Preferably, Phe243 is substituted by Leu.

In an embodiment, Arg292 is substituted by an amino acid chosen among Gly and Pro. Preferably, Arg292 is substituted by Pro.

In an embodiment, Tyr300 is substituted by an amino acid chosen among Lys, Phe, Leu and Ile. Preferably, Tyr300 is substituted by Leu.

In an embodiment, Val305 is substituted by Leu and Ile. Preferably, Val305 is substituted by Leu.

In an embodiment, Pro396 is substituted by Leu.

The anti-CD19 antibody of the invention comprises variable regions (VH and VL) specific to the CD19 antigen. More specifically, the antibody comprises CDRs that allows the antibody to bind specifically to the CD19 antigen.

In an embodiment, the present invention applies to any anti-CD19 antibody. That is to say, the anti-CD19 antibody comprises variable regions specific to CD19 antigen, or variable regions comprising CDRs specific to CD19 antigen, and the mutant Fc region according to the invention. Variable regions may be found in US20090098124, WO2002080987, WO2007024249, WO2008022152, WO2009052431, WO2009054863, WO2008031056, WO2007076950, WO2007082715, WO2004106381, WO1996036360, WO1991013974, U.S. Pat. No. 7,462,352, US20070166306 and WO2005092925. The person skilled in the art may refer to these documents as source of variable regions or CDRs specific to CD19.

In an embodiment, the antibody is specific for, or recognizes, a non-internalizing epitope on the CD19 antigen. The applicant has developed two murine anti-CD19 antibodies called mR005-1 and mR005-2, whose variable regions have been sequences and the CDRs identified. The present invention thus includes as preferred embodiments the use of the variable regions or the CDRs derived from mR005-1 and mR005-2.

In a first preferred embodiment, the anti-CD19 antibody of the invention comprises the following CDRs:

|  | SEQ ID N°: | Sequence IMGT ® | SEQ ID N°: | Sequence Kabat ® | SEQ ID N°: | Sequence (Common numbering system) |
|---|---|---|---|---|---|---|
| | | | VH mR005-1 | | | |
| CDR1 | 3 | GYAFSSYW | 9 | SYWVN | 14 | SSYW |
| CDR2 | 4 | IYPGDGDT | 10 | QIYPGDGDTNYNGKFKG | 4 | IYPGDGDT |
| CDR3 | 5 | ARSITTVVGCAMDY | 11 | SITTVVGCAMDY | 11 | SITTVVGCAMDY |
| | | | VL mR005-1 | | | |
| CDR1 | 6 | DHINNW | 12 | KASDHINNWLA | 6 | DHINNW |
| CDR2 | 7 | GAT | 13 | GATTLET | 7 | GAT |
| CDR3 | 8 | QQSWNTPWT | 8 | QQSWNTPWT | 8 | QQSWNTPWT |

In a second preferred embodiment, the anti-CD19 antibody of the invention comprises the following CDRs:

|  | SEQ ID NO: | Sequence IMGT ® | SEQ ID NO: | Sequence Kabat ® | SEQ ID NO: | Sequence (Common numbering system) |
|---|---|---|---|---|---|---|
| | | | VH mR005-2 | | | |
| CDR1 | 15 | GYTFTSYV | 21 | SYVMH | 26 | TSYV |
| CDR2 | 16 | VNPYNDGT | 22 | YVNPYNDGTKYNEKFKG | 16 | VNPYNDGT |
| CDR3 | 17 | ARGPYYYGSSPFDY | 23 | GPYYYGSSPFDY | 23 | GPYYYGSSPFDY |
| | | | VL mR005-2 | | | |
| CDR1 | 18 | QSLENSNGNTY | 24 | RSSQSLENSNGNTYLN | 18 | QSLENSNGNTY |
| CDR2 | 19 | RVS | 25 | RVSNRFS | 19 | RVS |
| CDR3 | 20 | LQVTHVPPT | 20 | LQVTHVPPT | 20 | LQVTHVPPT |

By definition, these CDRs include variant CDRs, by deletion, substitution or addition of one or more amino acid(s), which variant keeps the specificity of the original CDR. The common numbering system provides for a CDR definition having the shortest amino acid sequences or the minimal CDR definition.

In an embodiment, the antibody comprises the CDRs whose sequence is depicted on SEQ ID NO: 14, 4, 11 and/or 6, 7, 8.

In an embodiment, the antibody comprises the CDRs whose sequence is depicted on SEQ ID NO: 3, 4, 5 and/or 6, 7, 8.

In an embodiment, the antibody comprises the CDRs whose sequence is depicted on SEQ ID NO: 9, 10, 11 and/or 12, 13, 8.

In an embodiment, the antibody comprises the CDRs whose sequence is depicted on SEQ ID NO: 26, 16, 23 and/or 18, 19, 20.

In an embodiment, the antibody comprises the CDRs whose sequence is depicted on SEQ ID NO: 15, 16, 17 and/or 18, 19, 20.

In an embodiment, the antibody comprises the CDRs whose sequence is depicted on SEQ ID NO: 21, 22, 23 and/or 24, 25, 20.

The invention further comprises each one of these embodiments wherein the antibody further comprises an Fc region having the amino acid sequence depicted on SEQ ID NO: 1.

The antibody may be a monoclonal antibody, a chimeric antibody, a humanized antibody, a full human antibody, a bispecific antibody, an antibody drug conjugate or an antibody fragment. A "humanized antibody" or "chimeric humanized antibody" shall mean an antibody derived from a non human antibody, typically a murine antibody, that retains or substantially retains the antigen-binding properties of the parental antibody, but which is less immunogenic in humans.

In an embodiment, the whole variable regions VH and/or VL are murine.

In another embodiment, the variable region VH and/or VL has been humanized, with a framework region of human origin, such as derived from human IgG1.

The invention encompasses any modifications (substitutions, deletions, additions) of the variable regions of the invention (derived from R005-1 or R005-2) which do not change the specificity of said variable regions, say the recognition of the same internalizing epitope on the CD19 antigen.

In an embodiment, the antibody of the invention is bispecific, with one variable region VH+VL which contains CDRs according to the invention.

In an embodiment, the antibody triggers programmed cell death or apoptosis. In an embodiment, the antibody is for use for CD19 positive B-cell disorders.

In an embodiment, the antibody is for use on refractory or relapse anti-CD20 antibody treated patients.

In an embodiment, the antibodies of the invention have an Fc region having an interesting and valuable glycosylation profile, especially a low fucose level and/or a high oligomannose level and/or presence of sialic acid and have been produced in wild-type rodent mammalian cells, preferably wild-type CHO cells. By definition, in the present study these cells have not been modified or cultured in specific conditions to alter the glycosylation. For example, these cells have not been modified be deficient in 1,6-fucosyltransferase. The invention is thus based on the production of anti-CD19 antibodies having an interesting and valuable glycosylation profile, especially a low fucose level and/or a high oligomannose level and/or presence of sialic acid owing the mutations in the Fc region.

The present invention provides for this anti-CD19 antibody which after transfection and expression in mammalian cells, especially rodent cells, such as CHO cells, including of the wild-type, have a very interesting glycosylation profile and in particular have an interesting and valuable glycosylation profile, especially a low fucose level and/or a high oligomannose level and/or presence of sialic acid, especially a low level of sialic acid.

The present invention provides the person skilled in the art with a method to produce an anti-CD19 antibody in mammalian cells, without the need to engineer these cells, for example to render these cells deficient in 1,6-fucosyltransferase, or in the presence of agents which are able to impact on fucose level or to use special cell lines with specific glycosylation function.

In an embodiment, the antibody is produced on mammalian cells, in particular rodent cells, preferably CHO cells, preferably wild-type, such as the wild type DG44 CHO cells (purchased by ATCC).

The method for producing the anti-CD19 antibody is another object of the invention.

In an embodiment, the method comprises the combination of an Fc as disclosed herein with at least a variable region to give an anti-CD19 antibody.

In an embodiment, the mammal cells, preferably rodent cells such as CHO cells, preferably wild-type cells are transfected with one or several expression vectors. Preferably, the cells are co-transfected with an expression vector for light chain and with an expression vector for heavy chain.

The expression vector for the heavy chain contains a nucleic acid sequence SEQ ID NO: 2 which encode the variant Fc region according to the invention.

Cell transfection is also object of the invention. As transfection that may be performed, one may mention without limitation standard transfection procedures, well-known from the man skilled in the art may be carried out, such as calcium phosphate precipitation, DEAE—Dextran mediated transfection, electroporation, nucleofection (AMAXA®, GE), liposome-mediated transfection (using Lipofectin® or Lipofectamine® technology for example) or microinjection.

The expression vector for the heavy chain contains a nucleic acid sequence which encodes the variant Fc region according to the invention which comprises an amino acid substitution at each of the amino acid positions 243, 292, 300, 305 and 396. In an embodiment, this nucleic acid sequence also comprises a nucleic acid sequence encoding an antibody variable region which is specific for, or specifically recognizes, a CD19 antigen.

Preferably, the variable region recognizes a non internalizing CD19 epitope or determinant.

Preferably, the vector contains a nucleic acid sequence encoding the variable region of the parental murine R005-1 which recognizes a non internalizing CD19 epitope or determinant.

Preferably, the vector contains a nucleic acid sequence encoding the variable region of the parental murine R005-2 which recognizes a non internalizing CD19 epitope or determinant.

The expression vector comprises a nucleic acid sequence or nucleic acid sequences which code(s) for the variable region that is wished. Various embodiments of variable regions which can be expressed by the vector are presented below.

In a first embodiment, the variable region VH comprises the VH CDRs CDR1, CDR2, and CDR3 of or derived from R005-1.

In an embodiment, the variable region VH comprises the R005-1 CDRs whose sequence is depicted on SEQ ID NO: 14, 4, 11.

In another embodiment, the variable region VH comprises the CDRs whose sequence is depicted on SEQ ID NO: 3, 4, 5.

In another embodiment, the variable region VH comprises the CDRs whose sequence is depicted on SEQ ID NO: 9, 10, 11.

In a first embodiment, the variable region VH comprises the VH CDRs CDR1, CDR2, and CDR3 of or derived from R005-2.

In an embodiment, the variable region VH comprises the CDRs whose sequence is depicted on SEQ ID NO: 26, 16, 23.

In another embodiment, the variable region VH comprises the CDRs whose sequence is depicted on SEQ ID NO: 15, 16, 17.

In another embodiment, the variable region VH comprises the CDRs whose sequence is depicted on SEQ ID NO: 21, 22, 23.

In an embodiment, the variable region mR005-1 VH has the amino acid sequence as depicted on SEQ ID NO: 27.

In another embodiment, the vector comprises a nucleic acid sequence as depicted on SEQ ID NO: 28.

In another embodiment, the variable region mR005-2 VH has the amino acid sequence as depicted on SEQ ID NO: 31.

In another embodiment, the vector comprises a nucleic acid sequence as depicted on SEQ ID NO: 32.

In an embodiment, the vector comprises a nucleic acid sequence coding for the CDRs according to SEQ ID NO: 14, 4, 11; or 3, 4, 5; or 9, 10, 11 and a nucleic acid coding for an Fc region having the sequence depicted on SEQ ID NO:1.

In an embodiment, the vector comprises a nucleic acid sequence as depicted on SEQ ID NO: 28 and a nucleic acid coding for an Fc region having the sequence depicted on SEQ ID NO: 1.

In another embodiment, the vector comprises a nucleic acid sequence coding for an amino acid sequence as depicted on SEQ ID NO: 27 and a nucleic acid coding for an Fc region having the sequence depicted on SEQ ID NO: 1.

In another embodiment, the amino acid sequence comprises the CDRs according to SEQ ID NO: 26, 16, 23, or 15, 16, 17, or 21, 22, 23 and a nucleic acid coding for an Fc region having the amino acid sequence depicted on SEQ ID NO: 1.

In an embodiment, the vector comprises the nucleic acid sequence as depicted on SEQ ID NO: 32 and a nucleic acid coding for an Fc region having the sequence depicted on SEQ ID NO: 1.

In another embodiment, the vector comprises a nucleic acid sequence coding for an amino acid sequence as depicted on SEQ ID NO: 31 and a nucleic acid coding for an Fc region having the sequence depicted on SEQ ID NO: 1.

The nucleic acid sequence coding for Fc encodes an Fc region having the amino acid sequence SEQ ID NO: 1 or a derivative thereof, say which may comprise other amino acid mutations (substitution, addition or deletion) with the proviso that position 326 or 333 is not mutated or positions 326 and 333 are not simultaneously mutated.

The expression vector for the light chain contains a nucleic acid sequence which encodes a human Kappa or Lambda chain, preferably a human Kappa chain and an antibody variable region which is specific for, or specifically recognizes, a CD19 antigen. Preferably, the variable region recognizes a non internalizing CD19 epitope.

The expression vector comprises a nucleic acid sequence or nucleic acid sequences which code(s) for the variable region that is wished. Various embodiments of variable regions which can be expressed by the vector are presented below.

In a first embodiment the variable region VL comprises the VL CDRs CDR1, CDR2, and CDR3 of R005-1.

In an embodiment, the variable region VL comprises the CDRs whose sequence is depicted on SEQ ID NO: 6, 7, 8.

In another embodiment, the vector comprises the CDRs whose sequence is depicted on SEQ ID NO: 12, 13, 8.

In an embodiment, the vector comprises the nucleic acid sequence as depicted on SEQ ID NO: 30.

In another embodiment, the vector comprises a nucleic acid sequence coding for an amino acid sequence as depicted on SEQ ID NO: 29.

In a first embodiment the variable region VL comprises the VL CDRs CDR1, CDR2, and CDR3 of R005-2.

In an embodiment, the variable region VL comprises the CDRs whose sequence is depicted on SEQ ID NO: 18, 19, 20.

In another embodiment, the variable region VL comprises the CDRs whose sequence is depicted on SEQ ID NO: 24, 25, 20.

In an embodiment, the vector comprises the nucleic acid sequence as depicted on SEQ ID NO: 34.

In another embodiment, the vector comprises a nucleic acid sequence coding for an amino acid sequence as depicted on SEQ ID NO: 33.

The expression vectors comprise these nucleic acid sequences and regulatory sequences allowing expression of the former. In an embodiment, a unique vector comprises both nucleic acid sequences and is able to encode the VH and the VL.

Preferably, the invention comprises the use of one single vector or a set of vectors and the vector or the vectors comprise (1) a nucleic acid sequence encoding an antibody variable region comprising the VH CDRs as mentioned above and a variant Fc region comprising an amino acid substitution at each of the amino acid positions 243, 292, 300, 305 and 396, and (2) a nucleic acid sequence encoding an antibody variable region comprising the VL CDRs as mentioned above and a human Kappa region.

These vectors are also objects of the invention, alone or as a set of vectors. As vectors that may be used, one may mention without limitation: pcDNA3.3, pOptiVEC, pFUSE, pMCM-VHE, pMONO, pSPORT1, pcDV1, pCDNA3, pCDNA1, pRc/CMV, pSEC.

Based on the specific amino acid substitutions according to the invention, the person skilled in the art is fully able to design the nucleic acid sequences with the codon mutations which allow the sequence to encode the variant Fc region according to the invention, taking into account the degeneracy of the genetic code.

This nucleic acid encoding a human Fc region comprising substitution at position 243 with Leucine (L), at position 292 with Proline (P), at position 300 with Leucine (L), at position 305 with Leucine (L) and at position 396 with Leucine, with the proviso that position 326 or 333 or both positions 326 or 333 are not substituted.

In an embodiment, the nucleic acid sequence encodes a variant Fc region wherein Phe243 is substituted by an amino acid chosen among Leu, Trp, Tyr, Arg and Gln.

Preferably, Phe243 is substituted by Leu.

In an embodiment, the nucleic acid sequence encodes a variant Fc region wherein Arg292 is substituted by an amino acid chosen among Gly and Pro. Preferably, Arg292 is substituted by Pro.

In an embodiment, the nucleic acid sequence encodes a variant Fc region wherein Tyr300 is substituted by an amino acid chosen among Lys, Phe, Leu and Ile. Preferably, Tyr300 is substituted by Leu.

In an embodiment, the nucleic acid sequence encodes a variant Fc region wherein Val305 is substituted by Leu and Ile. Preferably, Val305 is substituted by Leu.

In an embodiment, the nucleic acid sequence encodes a variant Fc region wherein Pro396 is substituted by Leu.

In an embodiment, the nucleic acid sequence encodes a variant Fc region wherein Phe243 is substituted by Leu, Arg292 is substituted by Pro, Tyr300 is substituted by Leu, Val305 is substituted by Leu, and Pro396 is substituted by Leu.

In an embodiment, the nucleic acid sequence comprises CDRs or variable regions according to the invention and a nucleic acid coding for an Fc region having the sequence depicted on SEQ ID NO: 2.

In an embodiment, the nucleic acid sequence comprises the VH CDRs or variable regions according to the invention and a nucleic acid coding for an Fc region having the sequence depicted on SEQ ID NO: 2.

In an embodiment, the nucleic acid comprises a nucleic acid sequence as depicted on SEQ ID NO: 28 and a nucleic acid coding for an Fc region having the sequence depicted on SEQ ID NO: 2.

In another embodiment, the nucleic acid comprises a nucleic acid sequence as depicted on SEQ ID NO: 32 and a nucleic acid coding for an Fc region having the sequence depicted on SEQ ID NO: 2.

In an embodiment, the nucleic acid comprises a nucleic acid sequence as depicted on SEQ ID NO: 30, and a nucleic acid coding for a human Kappa or Lambda chain.

In another embodiment, the nucleic acid comprises a nucleic acid sequence as depicted on SEQ ID NO: 34, and a nucleic acid coding for a human Kappa or Lambda chain.

Another object of the invention is the use of these expression vectors or a set of expression vectors containing nucleic acid sequence(s) according to the invention and regulatory sequences allowing the expression of the VH and VL regions of the anti-CD19 antibody in mammalian cells, in particular CHO cells, preferably of the wild type.

Another object of the invention is a host cell containing a vector or a set of vectors of the invention. The host cell may be a mammal cell, preferably a rodent cell, more preferably CHO cell. Still more preferably, the host cell may be a wild-type mammal cell, preferably a wild-type rodent cell, most preferably a wild-type CHO cell.

The person skilled in the art fully owns the methods to generate the antibodies according to the invention using such a vector or vectors and cells such as CHO cells.

Another object of the invention is a host cell containing a vector or a set of vectors of the invention. The host cell may be a mammal cell, preferably a rodent cell, more preferably CHO cell. Still more preferably, the host cell may be a wild-type mammal cell, preferably a wild-type rodent cell, most preferably a wild-type CHO cell.

Another object of the invention is a composition containing an anti-CD19 antibody according to the invention and a vehicle.

In an embodiment, the invention concerns a pharmaceutical composition containing an anti-CD19 antibody according to the invention and a physiologically acceptable vehicle or excipient.

In an embodiment, said composition comprises at least one other antibody. This supplemental or other antibody may be an anti-CD19 antibody or an antibody directed against another tumoral antigen. This other tumoral antigen may be CD20, CD52, CD22, EGF receptor, VEGF receptor, mimics ganglioside GD3, CEA, HER-2.

In an embodiment the composition comprises an anti-CD20 antibody.

In an embodiment the composition comprises an anti-CD52 antibody.

This other tumoral antigen may be in particular a murine monoclonal antibody, a chimeric antibody, a humanized antibody, a full human antibody.

In a particular embodiment, the pharmaceutical composition comprises an anti-CD19 antibody according to the invention and an anti-CD20 antibody. Among the anti-CD20 antibodies, one may mention in particular rituximab.

Another object of the invention is such a pharmaceutical composition, comprising at least two antibodies, including an anti-CD19 antibody according to the invention, and a physiologically acceptable vehicle or excipient, for a simultaneous, separated or delayed administration. In this case each one of the active principles is separately conditioned in a pharmaceutically acceptable vehicle.

Another object of the invention is a pharmaceutical composition comprising an anti-CD19 antibody according to the invention, as an anti-tumoral medicament.

Still another object of the invention is a pharmaceutical composition comprising an anti-CD19 antibody according to the invention and at least one other antibody directed against another tumoral antigen, such as CD20, as an anti-tumoral medicament.

Still another object of the invention is a pharmaceutical composition comprising an anti-CD19 antibody according to the invention and at least one chemotherapy drug. This drug may be endoxan, cyclophosphamide, doxorubicine, vincas alcaloides, steroides, platines (cisplatine, carboplatine, oxaliplatine), aracytine, bleomycine, etoposide, bendamustine . . . . In an embodiment, the additional drug is doxorubicin.

In an embodiment, the composition comprises both active principles in the same composition, with a pharmaceutically acceptable vehicle.

Another object of the invention is such a pharmaceutical composition, comprising an anti-CD19 antibody according to the invention and an additional drug, and a physiologically acceptable vehicle or excipient, for a simultaneous, separated or delayed administration. In this case each one of the active principles is separately conditioned in a pharmaceutically acceptable vehicle.

In an embodiment, these compositions are for use in the treatment of B-cells lymphomas. In an embodiment, these compositions are for use in the treatment B-cell non-Hodgkin's lymphoma (NHL), B-cell chronic lymphocytic leukaemia (B-CLL), hairy cell leukaemia and B-cell acute lymphocytic leukaemia (B-ALL).

In another embodiment, these compositions are for use in the treatment of an inflammation or an auto-immune disease, such as multiple sclerosis, rheumatoid arthritis and SLE.

Still another object of the invention is a method for the treatment of a patient in need thereof, comprising administering an antibody or a pharmaceutical composition according to the invention. The method aims at treating or preventing cancer, inflammation or autoimmune diseases.

In some embodiments, the antibodies of the invention may be administered in combination with a therapeutically or prophylactically effective amount of one or more anti-cancer agents, therapeutic antibodies or other agents known to those skilled in the art for the treatment and/or prevention of cancer, inflammation and/or autoimmune diseases.

In an embodiment, the method aims at treating or preventing B-cell disorders, such as but not limited to, B-cell malignancies. B-cell malignancies include NHL, B-CLL, hairy cell leukaemia and B-ALL.

In an embodiment, the method is applied to refractory or relapsed patients treated with anti-CD20 antibody.

In an embodiment, the method aims at treating or preventing autoimmune disease. In an embodiment, the method is applied to refractory or relapsed patients treated with anti-CD20 antibody.

In an embodiment, the method aims at treating or preventing graft-versus host diseases (GVHD), humoral rejection, or post-transplantation lymphoproliferative disorder in human transplant recipients. In an embodiment, the method is applied to refractory or relapsed patients treated with anti-CD20 antibody.

In an embodiment, the method comprises the administration to the patient of an anti-CD19 antibody according to the invention and an antibody directed against another tumoral antigen. This other tumoral antigen may be CD20, CD52, CD22, EGF receptor, VEGF receptor, mimics ganglioside, GD3, CEA, HER-2. This other tumoral antigen may be in particular a murine monoclonal antibody, a chimeric antibody, a humanized antibody, a human antibody. In an embodiment the composition comprises an anti-CD20 antibody. In another embodiment the composition comprises an anti-CD52 antibody.

In another embodiment, the method comprises the administration to the patient of an anti-CD19 antibody according to the invention, wherein the patient is, has been or will be treated with a chemotherapy drug. This drug may be for example endoxan, cyclophosphamide, doxorubicine, vincas alcaloides, steroides, platines (cisplatine, carboplatine, oxaliplatine), aracytine, bleomycine, etoposide, bendamustine . . . . In an embodiment, the additional drug is doxorubicin. Preferably, the patient is treated with both the antibody according to the invention and the additional drug. The antibody and the drug may be administered in the same composition or in separate compositions.

|         | Amino acid sequence VH | Nucleic acid sequence VH | Amino acid sequence VL | Nucleic acid sequence VL |
|---------|------------------------|--------------------------|------------------------|--------------------------|
| mR005-1 | SEQ ID NO: 27          | SEQ ID NO: 28            | SEQ ID NO: 29          | SEQ ID NO: 30            |
| mR005-2 | SEQ ID NO: 31          | SEQ ID NO: 32            | SEQ ID NO: 33          | SEQ ID NO: 34            |

Figure 5:
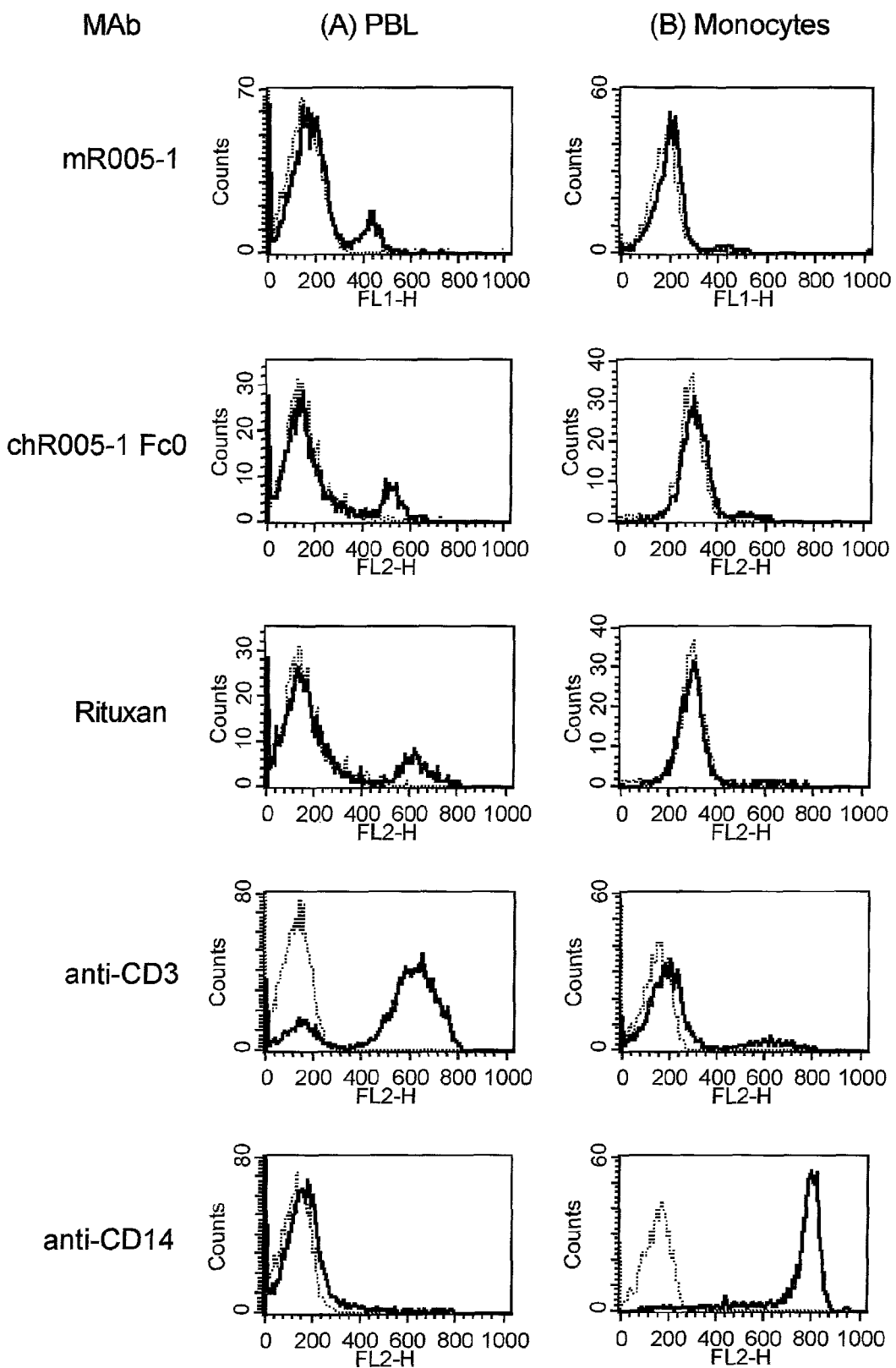

FIG. 5: Comparative staining between the native chimeric R005-1 Fc0 and the murine parental R005-1 MAb on PBMNC cells. Grey lines designated cytofluorometric histograms of negative isotype murine IgG1 or human IgG1 control MAb and black lines showed cytofluorometric histograms obtained on peripheral blood lymphocytes or on monocytes at 5 μg/ml for $1.10^6$ cells/ml. Representative experiments on three independent experiments.

Figure 6:
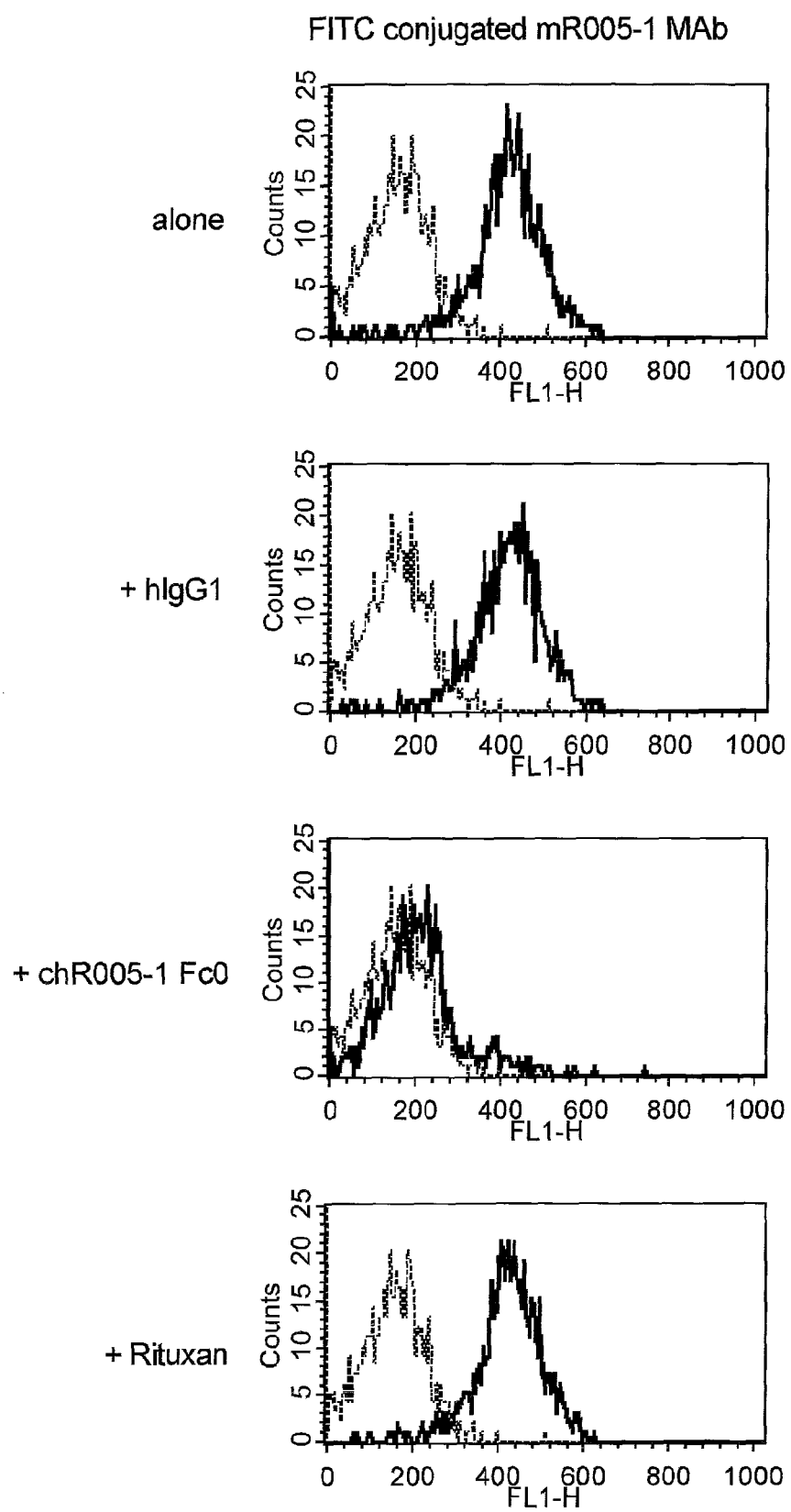

FIG. 6: Cross blocking experiment between the native chimeric R005-1 Fc0 and the murine parental mR005-1 MAb. Cells were pre-treated or not with the native chR005-1 Fc0 or with hIgG1 control MAb (5 μg/ml) before the staining with 10 μl of FITC conjugated mR005-1 on Raji Burkitt's lymphoma cells. Grey lines designated cytofluorometric histograms of negative isotype mouse IgG1 control MAb and black lines showed cytofluorometric histograms obtained with the FITC conjugated mR005-1. Representative experiment on three independent experiments.

FIG. 7: The cell labelling with the parental mR005-1 or chR005-1 Fc0 MAb triggered a down modulation of CD19 expression level. B-CLL cells were incubated with biotinylated MAbs at 4° C. for 30 min. At T0, T3 h, and T24 h, cells were stained with streptavidin-Alexa 488 nm (final dilution 1/1000) 30 min at 4° C. and fixed in formaldehyde 1%. 20 000 cells were then acquired on LSRII cytometer (BD bioscience, USA) and FlowJo analysis were done. Data represent one experiment representative of nine independent experiments.

Figure 8:
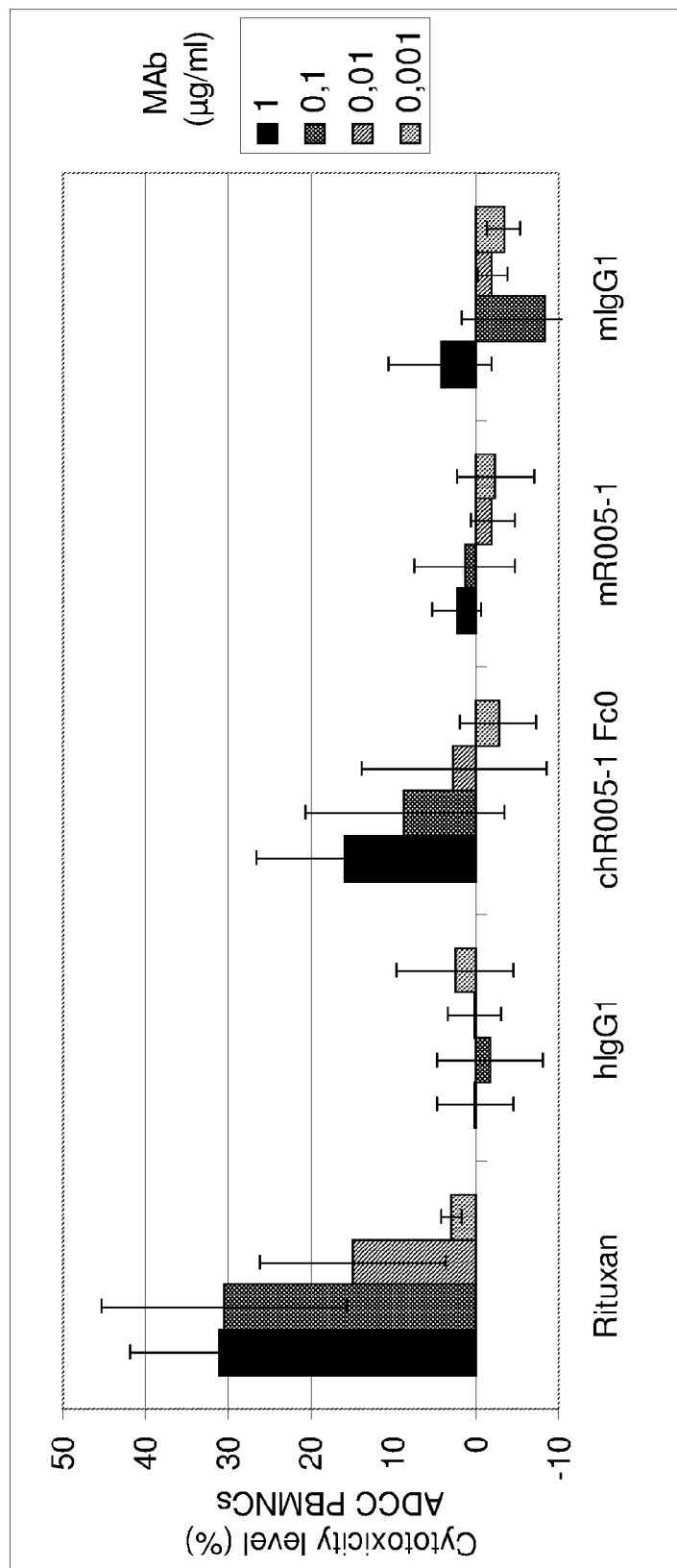

FIG. 8: The chR005-1 Fc0 MAb display a modest ADCC activity on Burkitt's lymphoma cells. Calcein-AM loaded Raji cells ($1 \times 10^5$ cells/nil) were incubated with interest MAbs for 20 min at 4° C. Effector cells (PBMNC) were added at the ratio E/T 50:1 for 4 hours at 37° C. under shaking condition. After centrifugation, supernatants were harvested and calcein-AM fluorescence was measured on fluorometer. ADCC lysis level was calculated following the formula: [experimental release−(target+effector spontaneous release)]/(maximal release−target spontaneous release)*100. Maximal release value was obtained by treating target cells with Triton X-100. Data represent mean+/−SD of three independent experiments.

Figure 9:
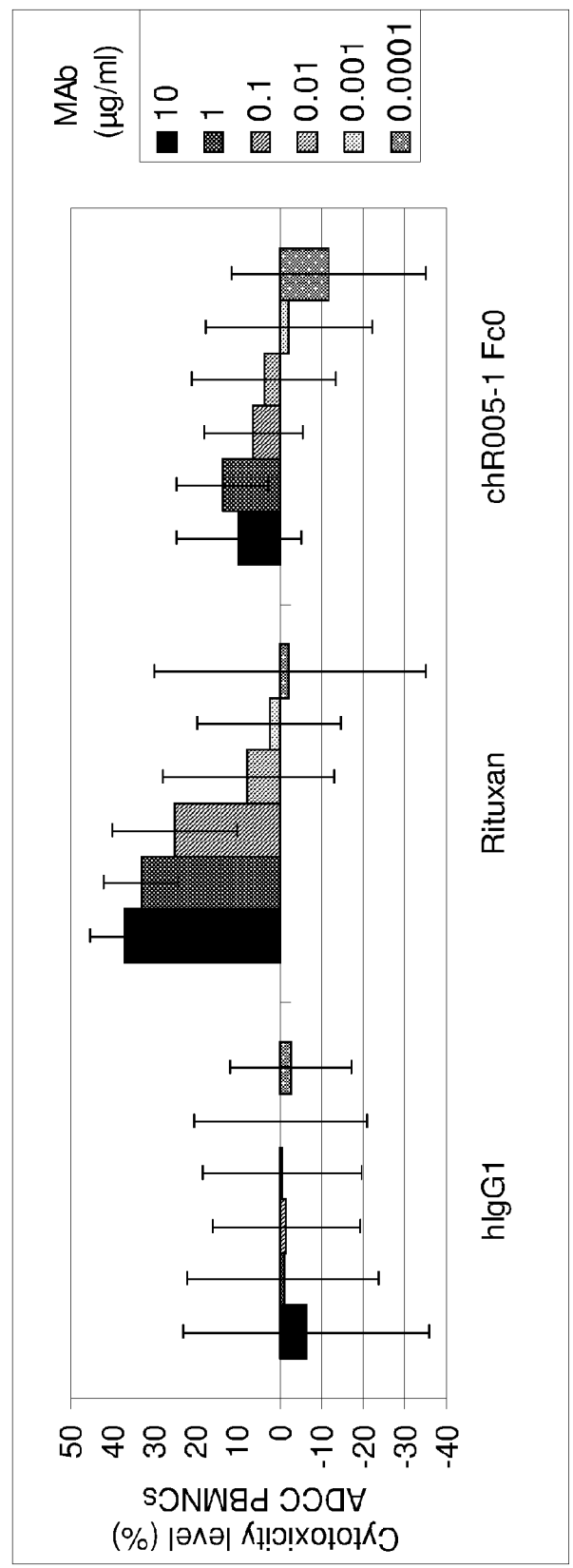

FIG. 9: chR005-1 Fc0 displayed a modest ADCC activity on primary B-CLL cells. Primary B-CLL cells were isolated after ficoll centrifugation. $1 \times 10^5$ cells/ml calcein-AM loaded cells were incubated with interest MAbs for 20 min at 4° C. Effector cells (PBMNC) were added at the ratio E/T 50:1 for 4 hours at 37° C. under shaking condition. After centrifugation, supernatants were harvested and calcein-AM fluorescence was measured on fluorometer. ADCC lysis level was calculated following the formula: [experimental release−(target+effector spontaneous release)]/(maximal release−target spontaneous release)*100. Maximal release value was obtained by treating target cells with Triton X-100. Data represent mean+/−SD of five independent experiments.

Figure 10:
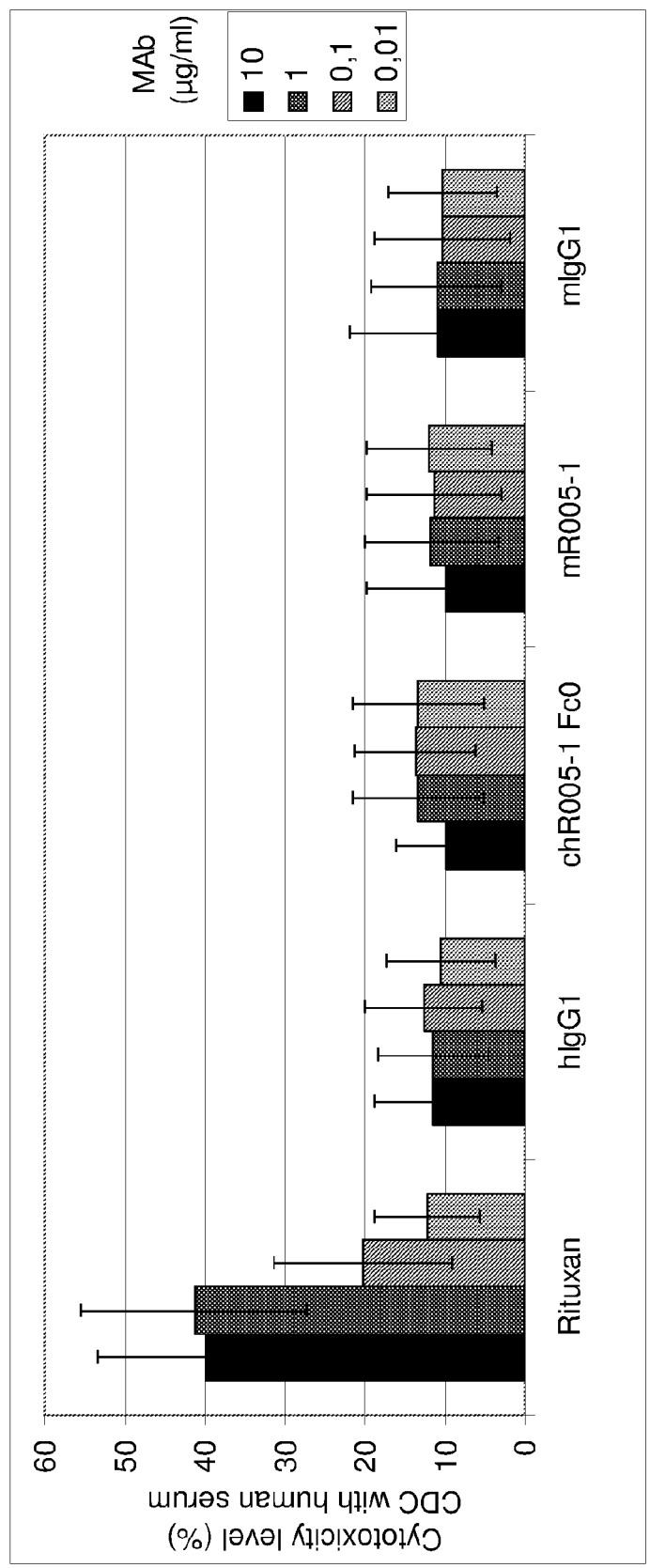

FIG. 10: The chR005-1 Fc0 did not trigger CDC activity on Burkitt's lymphoma cells. Raji cells ($2.10^6$ cells/ml) were incubated with interest MAbs for 20 min at 4° C. Then 5 μl of natural human complement was added for 4 hours at 37° C. under shaking condition. After incubation, supernatants were harvested and lactate deshydrogenase (LDH) was measured on fluorometer. CDC lysis level was calculated following the formula: (experimental release−target spontaneous release)/(maximal release−target spontaneous release)*100, where target without natural complement represented spontaneous release. Maximal release value was obtained by treating target cells with Triton X-100. Data represent mean+/−SD of three independent experiments.

FIG. 11: The amino acid and nucleic acid sequences of chimeric Fc20 variant MAb. Amino acids are shown as one-letter codes. According to the literature, the amino acid numbering of Fc region is based to the Kabat data base, (CH1: aa n°118 to 215; Hinge: aa n°216 to 230; CH2: aa n°231 to 340; CH3: aa n°341 to 447). SEQ ID NO: 1 for the amino acid sequence and SEQ ID NO: 2 for the nucleic acid sequence. Variations between the various Fc used in the invention with respect to native (wild type) Fc (Fc0):

| Name of the mutant | Mutations with respect to Fc0 |
|--------------------|-------------------------------|
| Fc20               | F243L/R292P/Y300L/V305L/P396L |
| Fc18               | F243L                         |
| Fc28               | Y300L/V305L                   |
| Fc19               | F243L/R292P/P396L             |
| Fc29               | F243L/R292P/V305L/P396L       |
| Fc30               | F243L/R292P/Y300L/P396L       |
| Fc14               | S239D/I332E                   |
| Fc24               | F243L/R292P/Y300L/V305L/K326A/E333A/P396L |
| Fc38               | F243L/R292P/Y300L/V305I/K326A/E333A/P396L |

Figure 12:
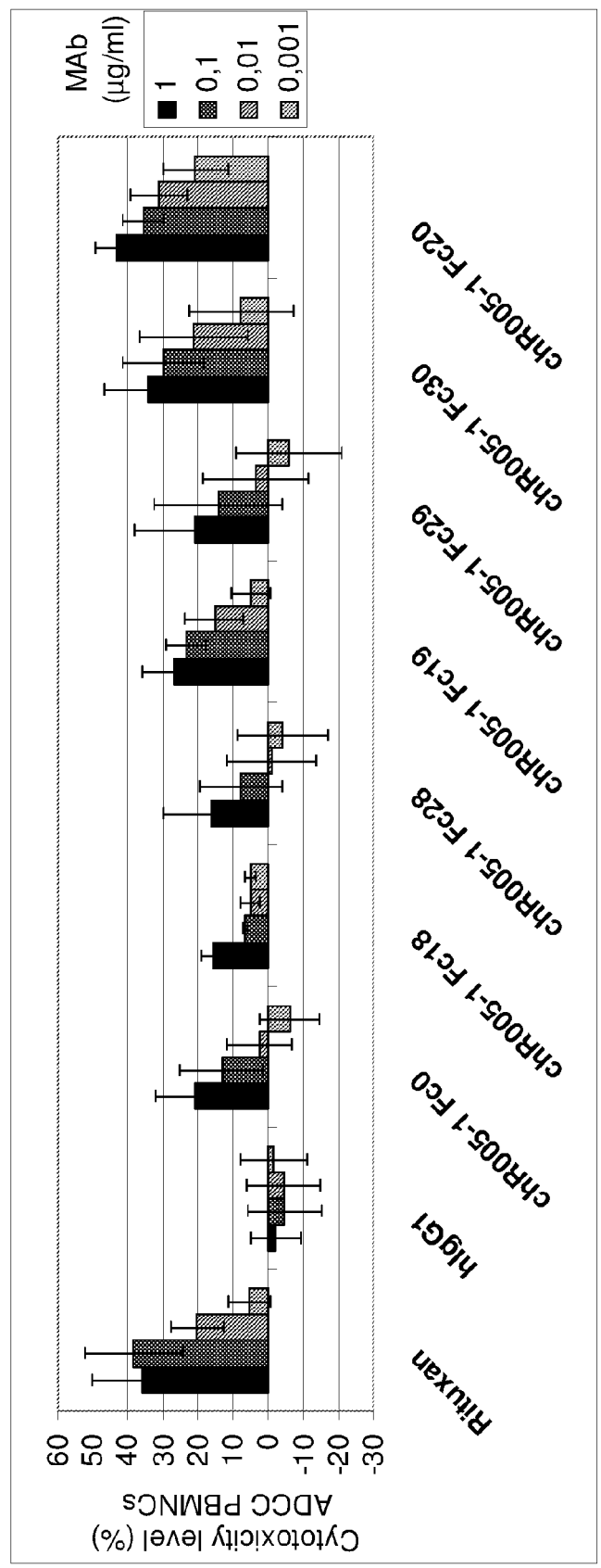

FIG. 12: Enhanced ADCC activity on Burkitt's lymphoma cells in the presence of PBMNC as effector cells. Calcein-AM loaded Raji cells ($1 \times 10^5$ cells/nil) were incubated with interest MAbs for 20 min at 4° C. Effector cells (PBMNC) were added at the ratio E/T 50:1 for 4 hours at 37° C. under shaking condition. After centrifugation, supernatants were harvested and calcein-AM fluorescence was measured on fluorometer. ADCC lysis level was calculated following the formula: [experimental release−(target+effector spontaneous release)]/(maximal release−target spontaneous release)*100. Maximal release value was obtained by treating target cells with Triton X-100. Data represent mean+/−SD of four independent experiments.

Figure 13:
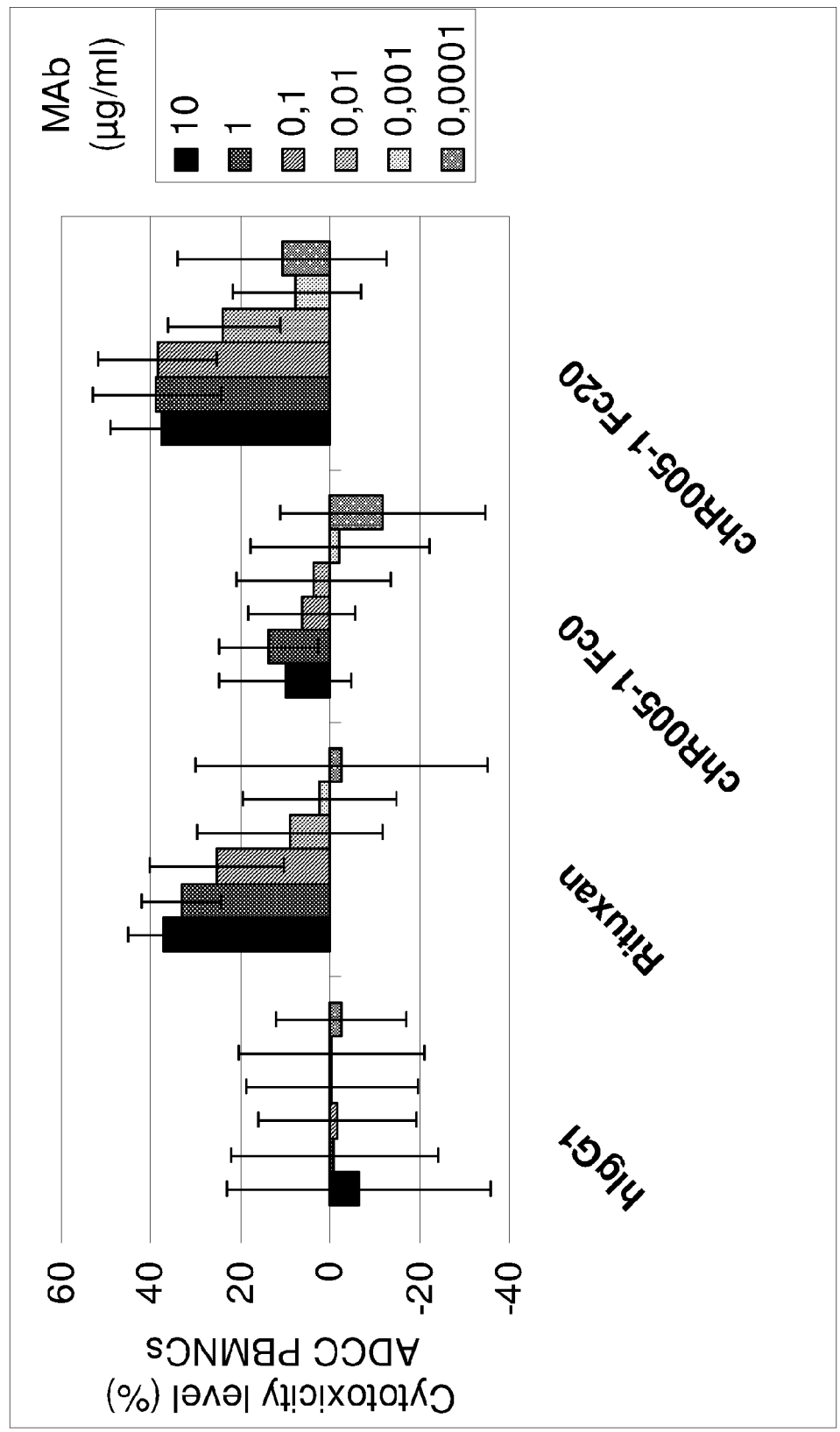

FIG. 13: chR005-1 Fc20 MAb mediated strong ADCC activity on primary B-CLL cells. Primary B-CLL cells were isolated after ficoll centrifugation. ($1 \times 10^5$ cells/nil) calcein-AM loaded cells were incubated with interest MAbs for 20 min at 4° C. Effector cells (PBMNC) were added at the ratio E/T 50:1 for 4 hours at 37° C. under shaking condition. After centrifugation, supernatants were harvested and calcein-AM fluorescence was measured on fluorometer. ADCC lysis level was calculated following the formula: [experimental release−(target+effector spontaneous release)]/(maximal release−target spontaneous release)*100. Maximal release value was obtained by treating target cells with Triton X-100. Data represent mean+/−SD of five independent experiments.

Figure 14:
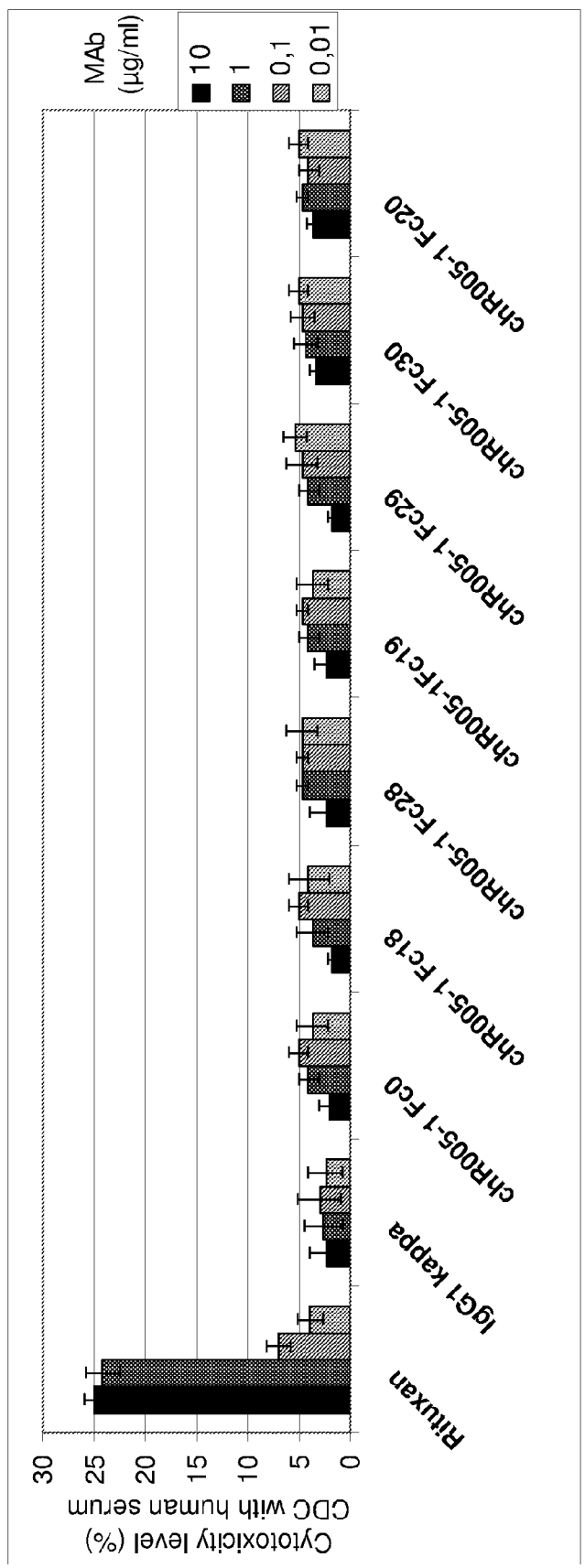

FIG. 14: The chR005-1 Fc20 MAb did not induce CDC activity on Burkitt's lymphoma cell. Raji cells ($2.10^6$ cells/ml) were incubated with interest MAbs for 20 min at 4° C. Then 5 µl/well of natural human complement was added for 4 hours at 37° C. under shaking condition. After incubation, supernatants were harvested and lactate deshydrogenase (LDH) was measured on fluorometer. CDC lysis level was calculated following the formula: [experimental release−spontaneous release)]/(maximal release−spontaneous release)*100, where target without natural complement represented spontaneous release. Maximal release value was obtained by treating target cells with Triton X-100. Data represent mean+/−SD of three independent experiments.

Figure 15:
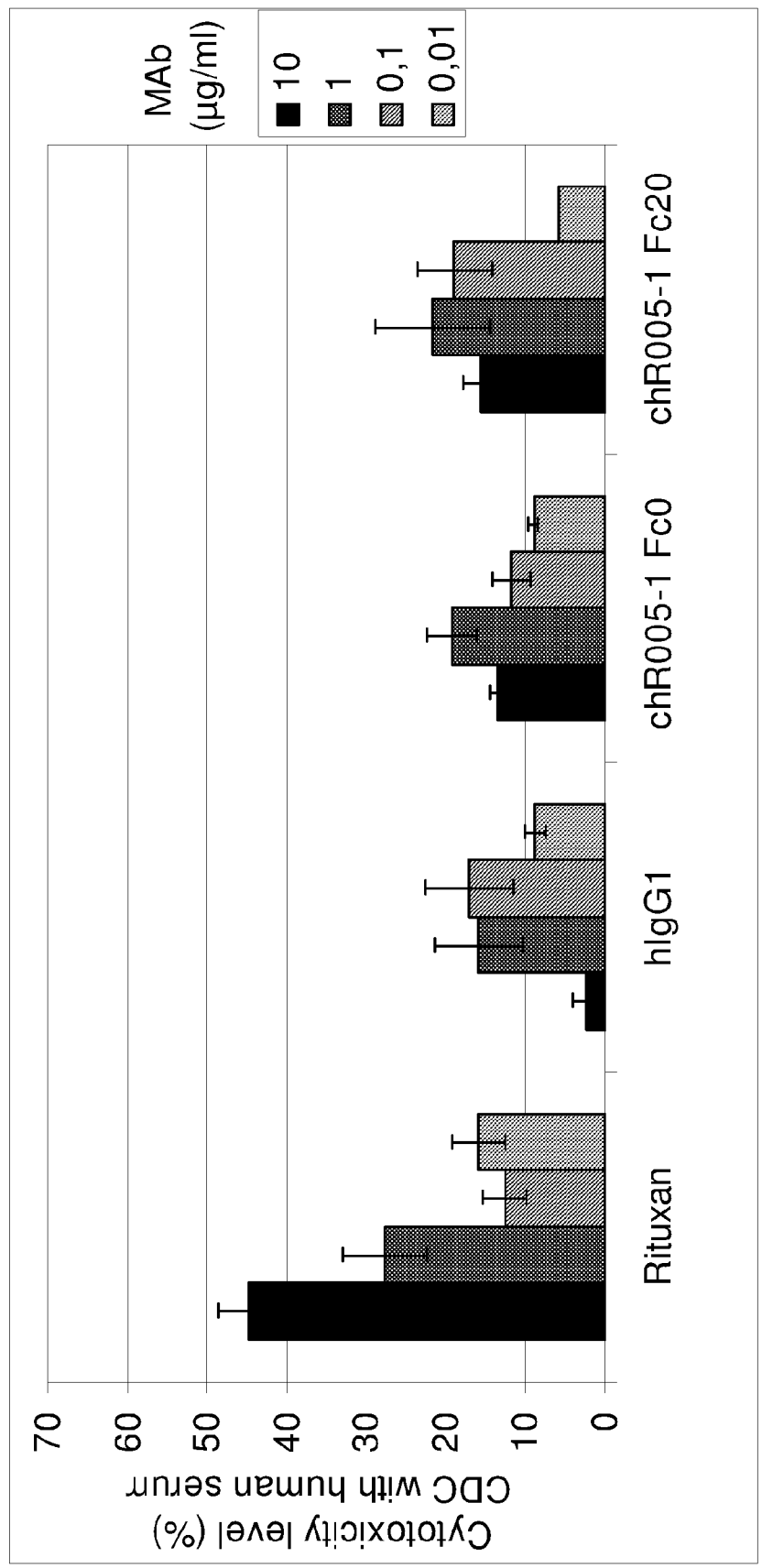

FIG. 15: The chR005-1 Fc20 MAb did not mediate strong CDC activity on primary B-CLL cells. B-CLL cells ($5 \times 10^4$ cells/ml) were incubated with interest MAbs for 20 min at 4° C. Then 5 µl/well of natural human complement was added for 4 hours at 37° C. under shaking condition. After incubation, supernatants were harvested and lactate deshydrogenase (LDH) was measured on fluorometer. CDC lysis level was calculated following the formula: (experimental release−spontaneous release)/(maximal release−spontaneous release) *100, where target without natural complement represented spontaneous release. Maximal release value was obtained by treating target cells with Triton X-100. Data represent one independent experiment.

Figure 16:
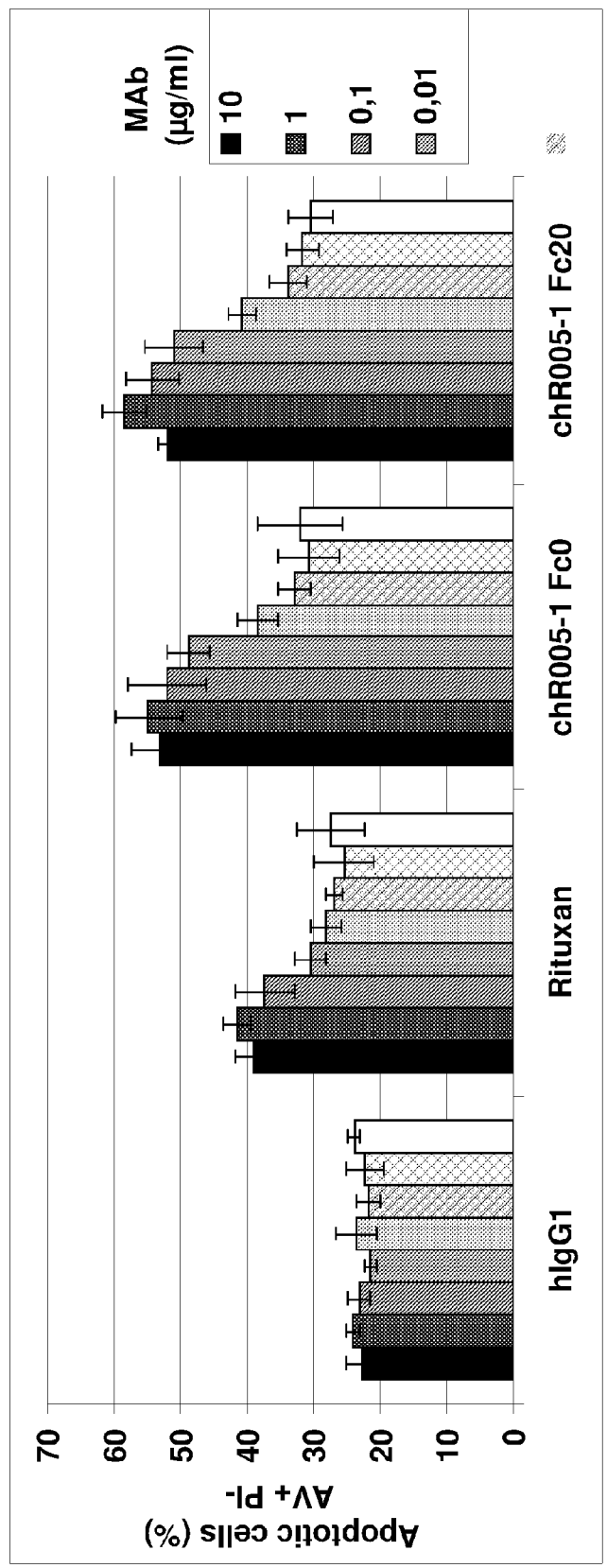

FIG. 16: The Fc engineering of anti-CD19 chR005-1 Fc 0 did not influence PCD in Burkitt's lymphoma cell line. The Burkitt's lymphoma cell line Raji was incubated with different MAb concentration for 5 hours. B-cells were double-stained with annexin V-FITC and propidium iodide (PI), and analyzed by flow cytometry. Data represent mean+/−SD of three independent experiments.

Figure 17:
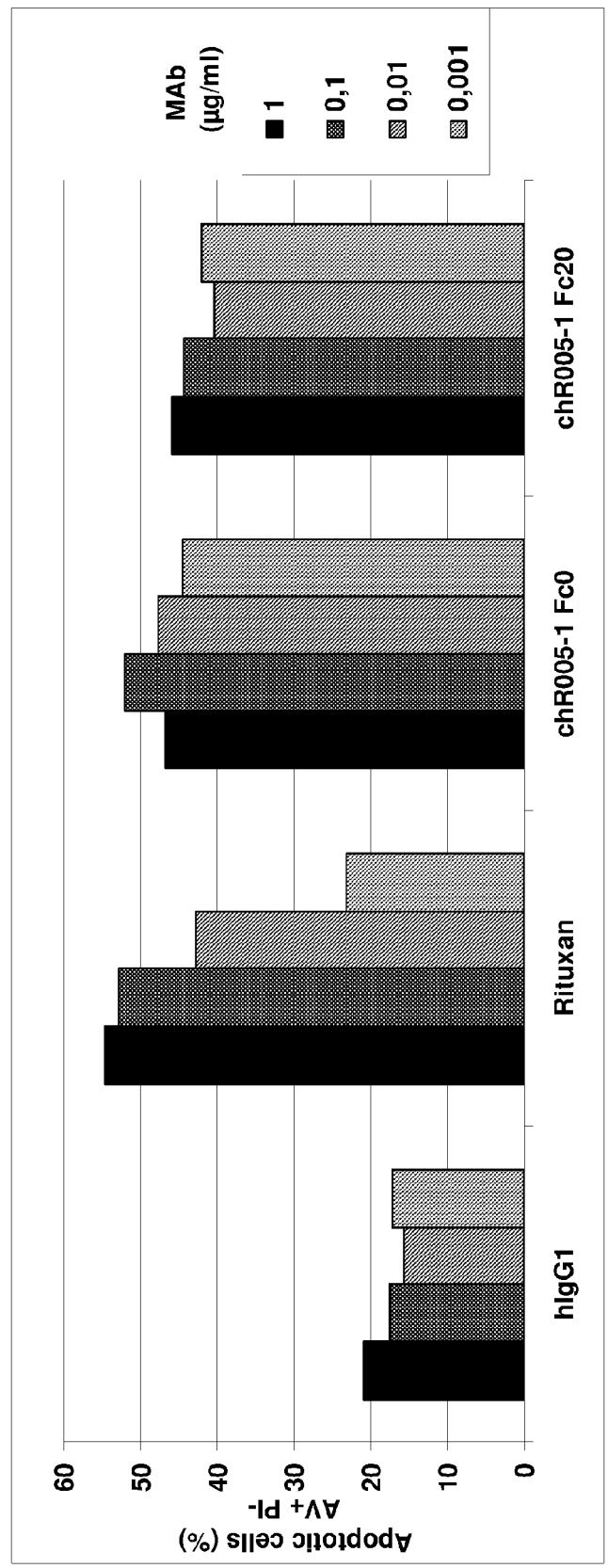

FIG. 17: The Fc engineering of anti-CD19 chR005-1 Fc 0 did not influence PCD in B-CLL. Primary B-CLL ($4 \times 10^4$ cells) were incubated with interest MAbs and controls for 24 hours at 37° C. in complete media. B-cells were double-stained with annexin V-FITC and propidium iodide (PI), and analyzed by flow cytometry. One representative experiment of four independent experiments.

Figure 18:
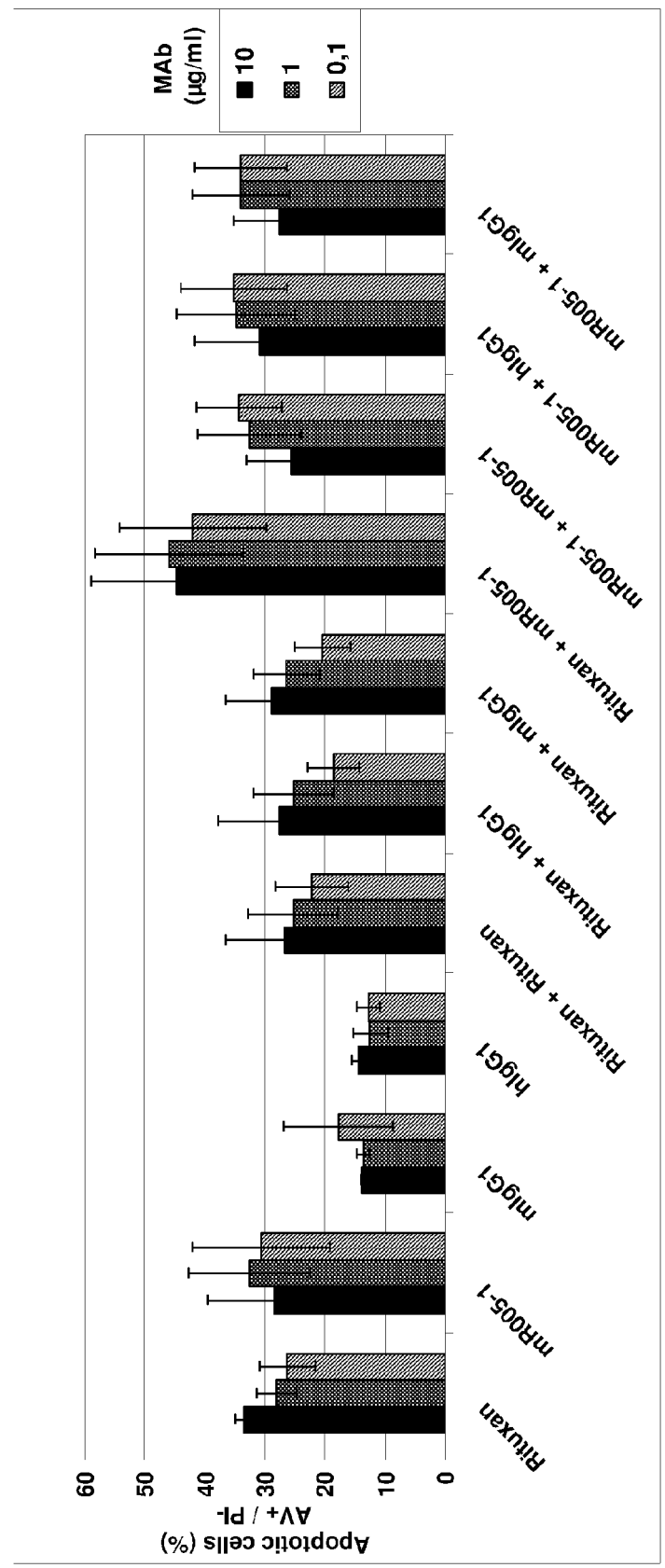

FIG. 18: The mR005-1 MAb combined with chimeric anti-CD20 (Rituximab®) synergized their apoptotic effect in Burkitt's lymphoma cells. Daudi cells ($4 \times 10^4$ cells) were incubated with interest MAbs in combination or not, and controls for 5 hours at 37° C. in complete media. B-cells were double-stained with annexin V-FITC and propidium iodide (PI), and analyzed by flow cytometry. Data represent mean+/−SD of three independent experiments.

Figure 19:
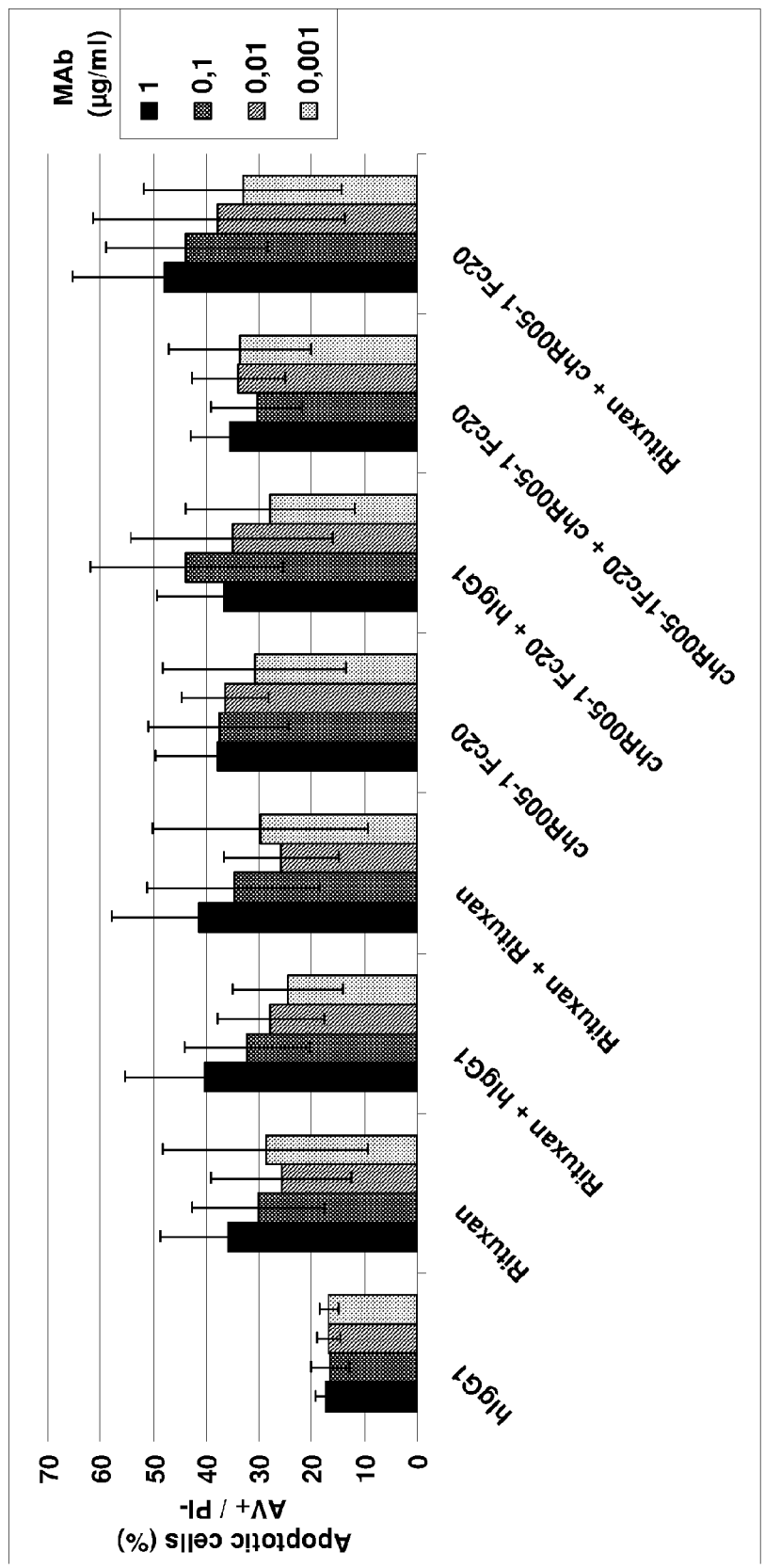

FIG. 19: The chR005-1 Fc20 MAb combined with chimeric anti-CD20 (Rituximab®) synergized their apoptotic effect in Burkitt's lymphoma cells. Daudi cells ($4 \times 10^4$ cells) were incubated with interest MAbs in combination or not, and controls for 5 hours at 37° C. in complete media. B-cells were double-stained with annexin V-FITC and propidium iodide (PI), and analyzed by flow cytometry. Data represent Mean+/−SD of two independent experiments.

Figure 20:
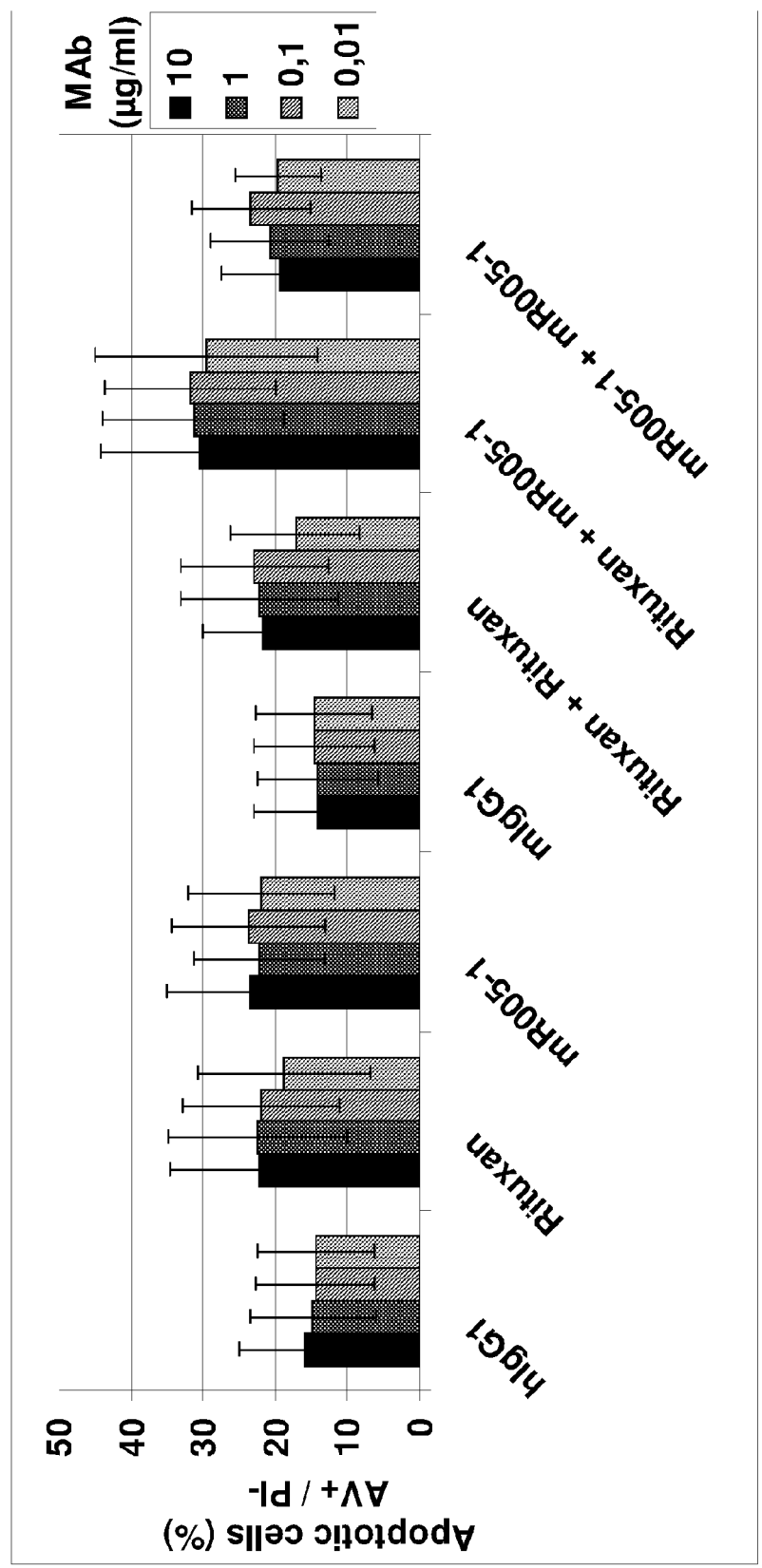

FIG. 20: Parental mR005-1 combined with chimeric anti-CD20 (Rituximab®) synergized their apoptotic effect in primary B-CLL cells. Primary B-CLL were isolated after ficoll centrifugation. $4 \times 10^6$ cells were incubated with interest MAbs in combination or not, and controls for 24 hours at 37° C. in complete media. Then cells were harvested and stained with Annexin V-FITC/Propidium Iodide and analyzed by flow cytometry. Apoptotic cells were defined as Annexin $V^+/PI^-$ cells. Data represent mean+/−SD of seven independent experiments.

Figure 21:
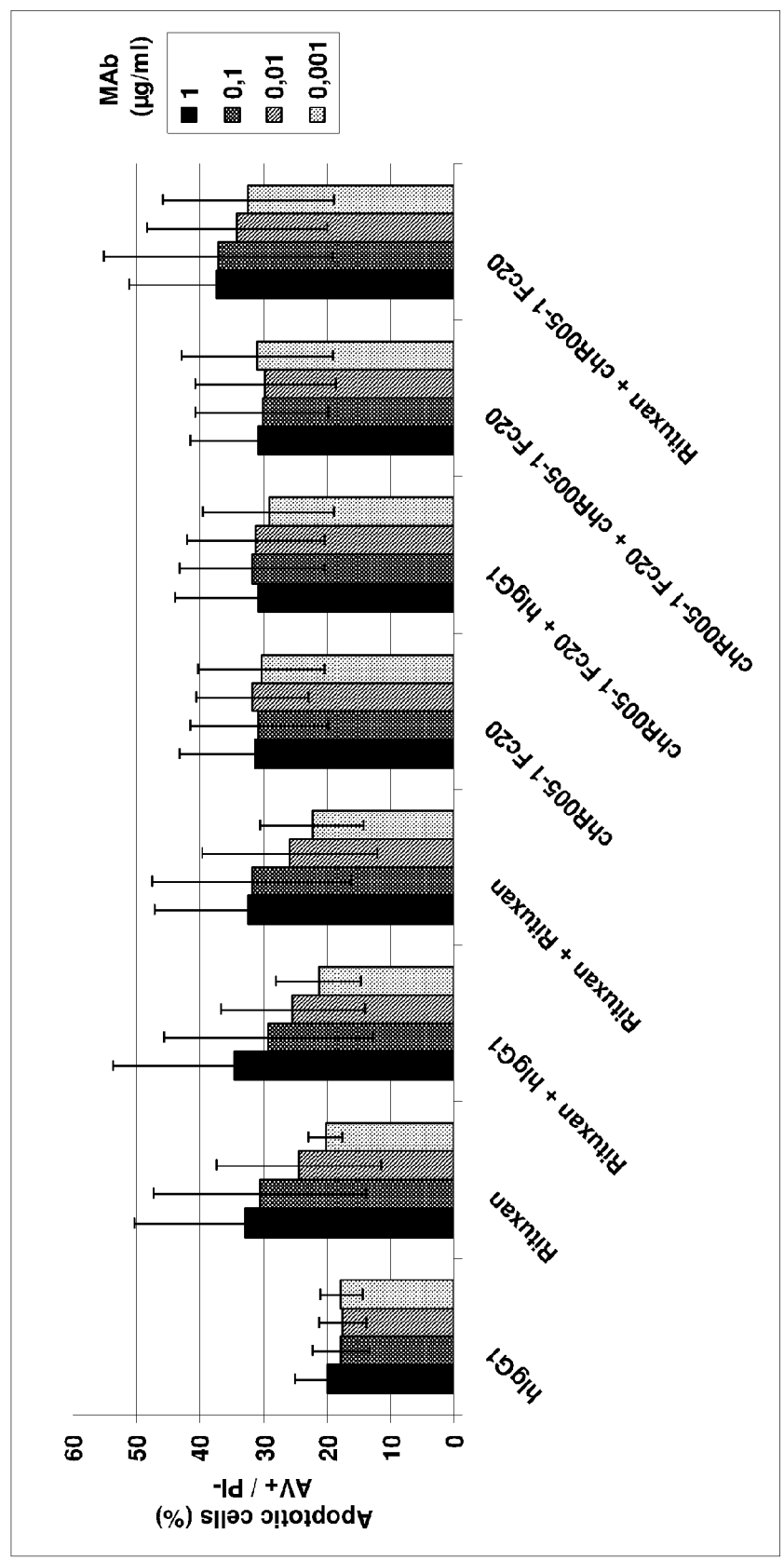

FIG. 21: The chR005-1 Fc20 MAb combined with chimeric anti-CD20 (Rituximab®) synergized their apoptotic effect in primary B-CLL cells. Primary B-CLL were isolated after ficoll centrifugation. B-CLL ($4 \times 10^4$ cells) were incubated with interest MAbs in combination or not, and controls for 24 hours at 37° C. in complete media. B-cells were double-stained with annexin V-FITC and propidium iodide (PI) and analyzed by flow cytometry. Data represent mean+/−SD of four independent experiments.

Figure 22:
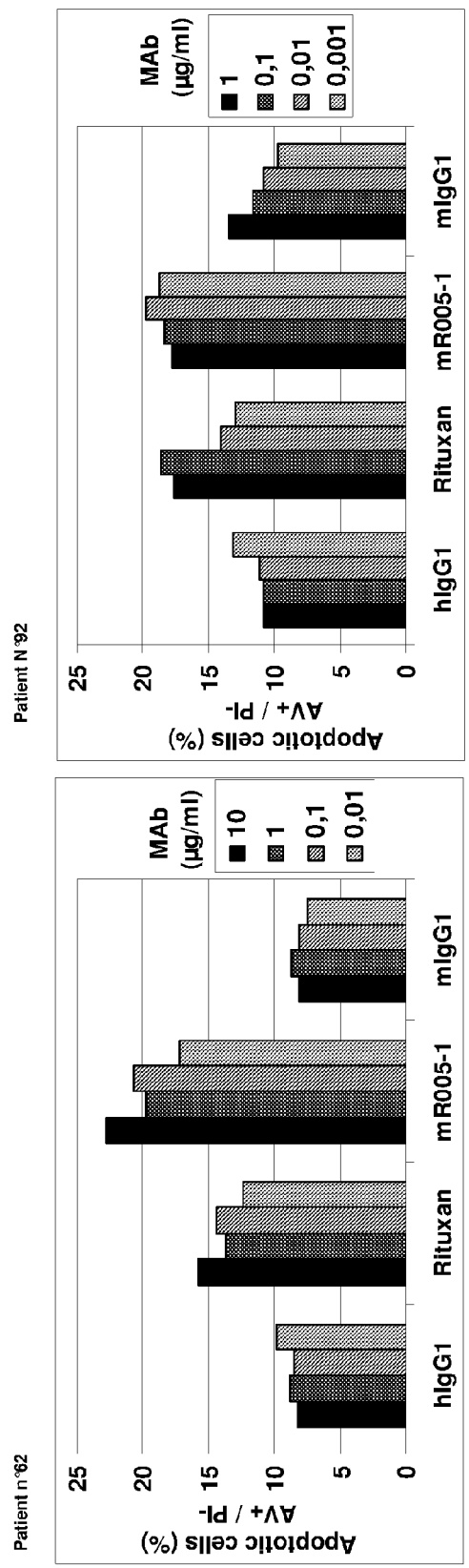

FIG. 22: The murine MAb R005-1 triggered apoptosis in primary B-CLL cells Rituximab® refractory. Primary B-CLL cells were isolated after ficoll centrifugation. $4 > 10^6$ cells were incubated with interest MAbs and controls for 24 hours at 37° C. in complete media. Then cells were harvested and stained with Annexin-V FITC/Propidium Iodide and analyzed by flow cytometry. Apoptotic cells were defined as annexin $V^+/PI^-$ cells. Data represent mean+/−SD of two independent experiments.

Figure 23:
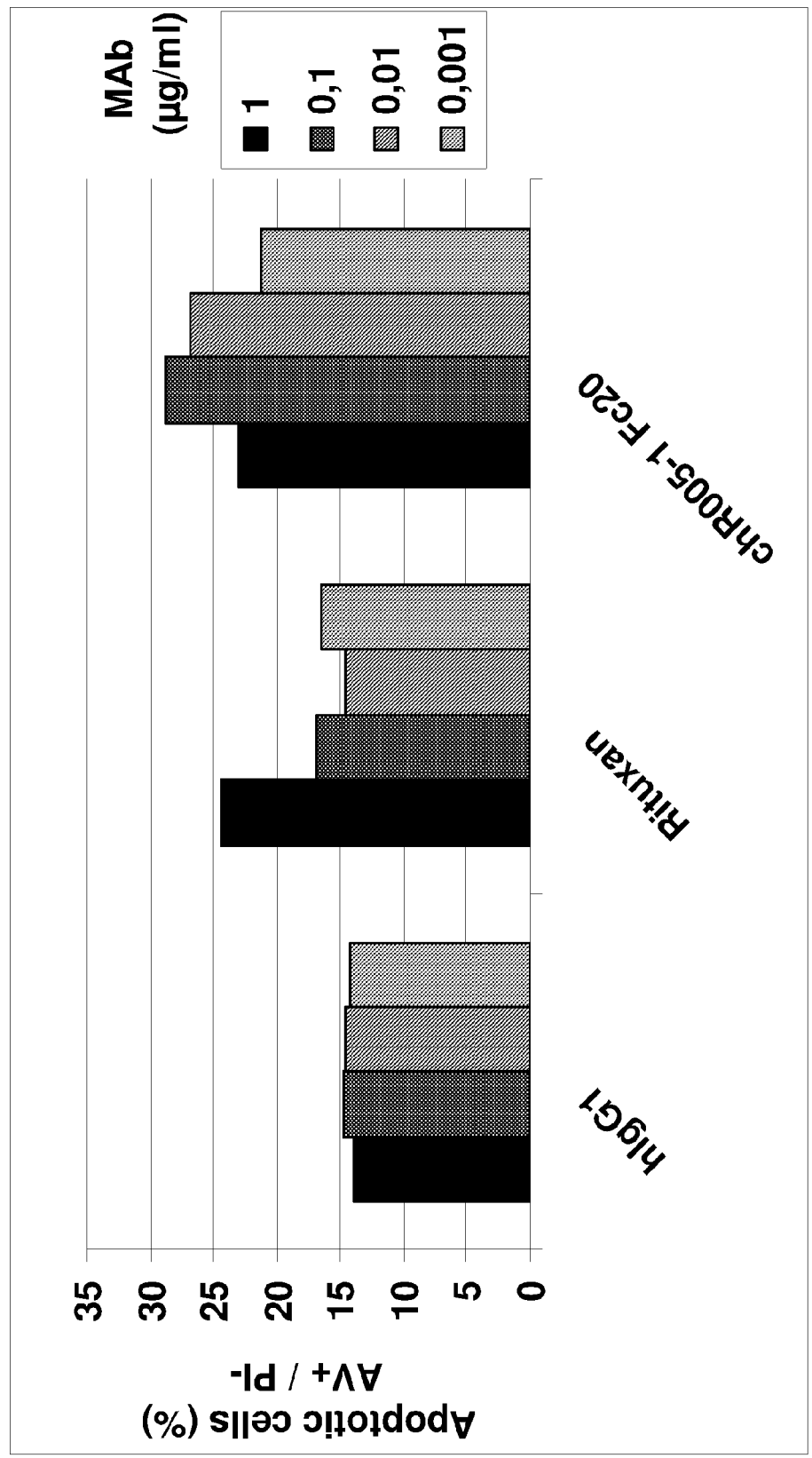

FIG. 23: The MAb chR005-1 Fc20 triggered apoptosis in primary B-CLL cells Rituximab® refractory. Primary B-CLL were isolated after ficoll centrifugation. B-CLL ($4 \times 10^4$ cells) were incubated with interest MAbs in combination or not, and controls for 24 hours at 37° C. in complete media. B-cells were double-stained with annexin V-FITC and propidium iodide (PI), and analyzed by flow cytometry on FacsCan cytometer (BD bioscience, USA). Representative data from one experiment.

Figure 24:
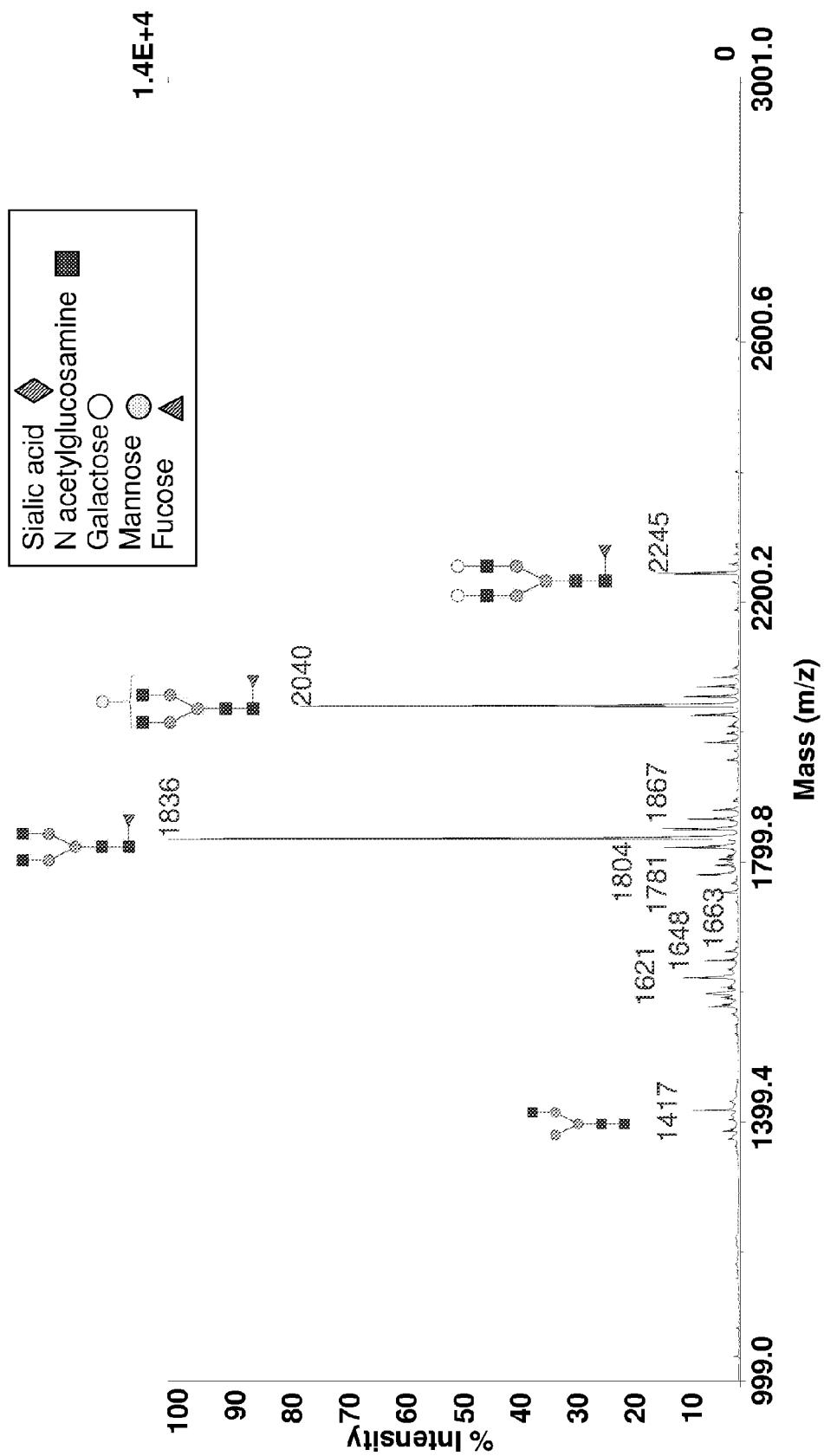

FIG. 24: Glycosylation profile of the MAb chR005-1 Fc0. Antibody oligosaccharides released by PNGase F digestion were analyzed using a MALDI-TOF Voyager DE PRO spectrometer. The m/z value corresponds to the sodium-associated oligosaccharide ion. The sugar composition of each peak shown is detailed in the table of FIG. 26. The schematic oligosaccharide structure of each major peak is illustrated on the right side of the charts: GlcNAc (closed circles), mannose (open squares), galactose (open diamonds) and fucose (open triangles).

Figure 25:
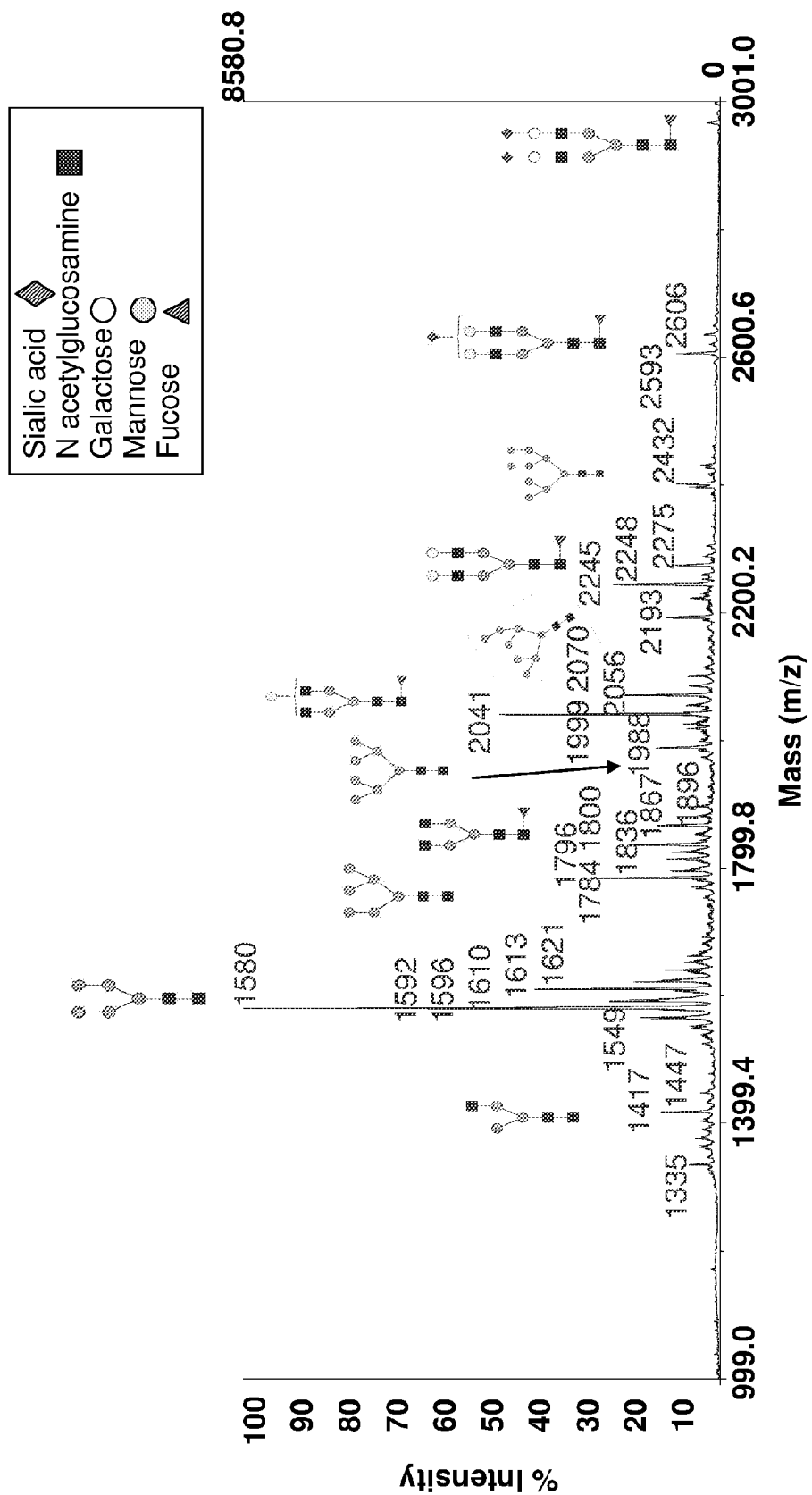

FIG. 25: Glycosylation profile of the MAb chR005-1 Fc20. Antibody oligosaccharides released by PNGase F digestion were analyzed using a MALDI-TOF MS spectrometer Reflex III. The m/z value corresponds to the sodium-associated oligosaccharide ion. The sugar composition of each peak shown is detailed in the table of FIG. 26. The schematic oligosaccharide structure of each major peak is illustrated on the right side of the charts: GlcNAc (closed circles), mannose (open squares), galactose (open diamonds) and fucose (open triangles).

FIG. 26: Assignment of carbohydrate structures by comparison with glycan standards following capillary electrophoresis with laser-induced fluorescence detection relative intensities of N-glycan types between the parental chR005-1 Fc0 and the optimized chR005-1 Fc20 MAbs expressed in wild type CHO cells.

Figure 27:
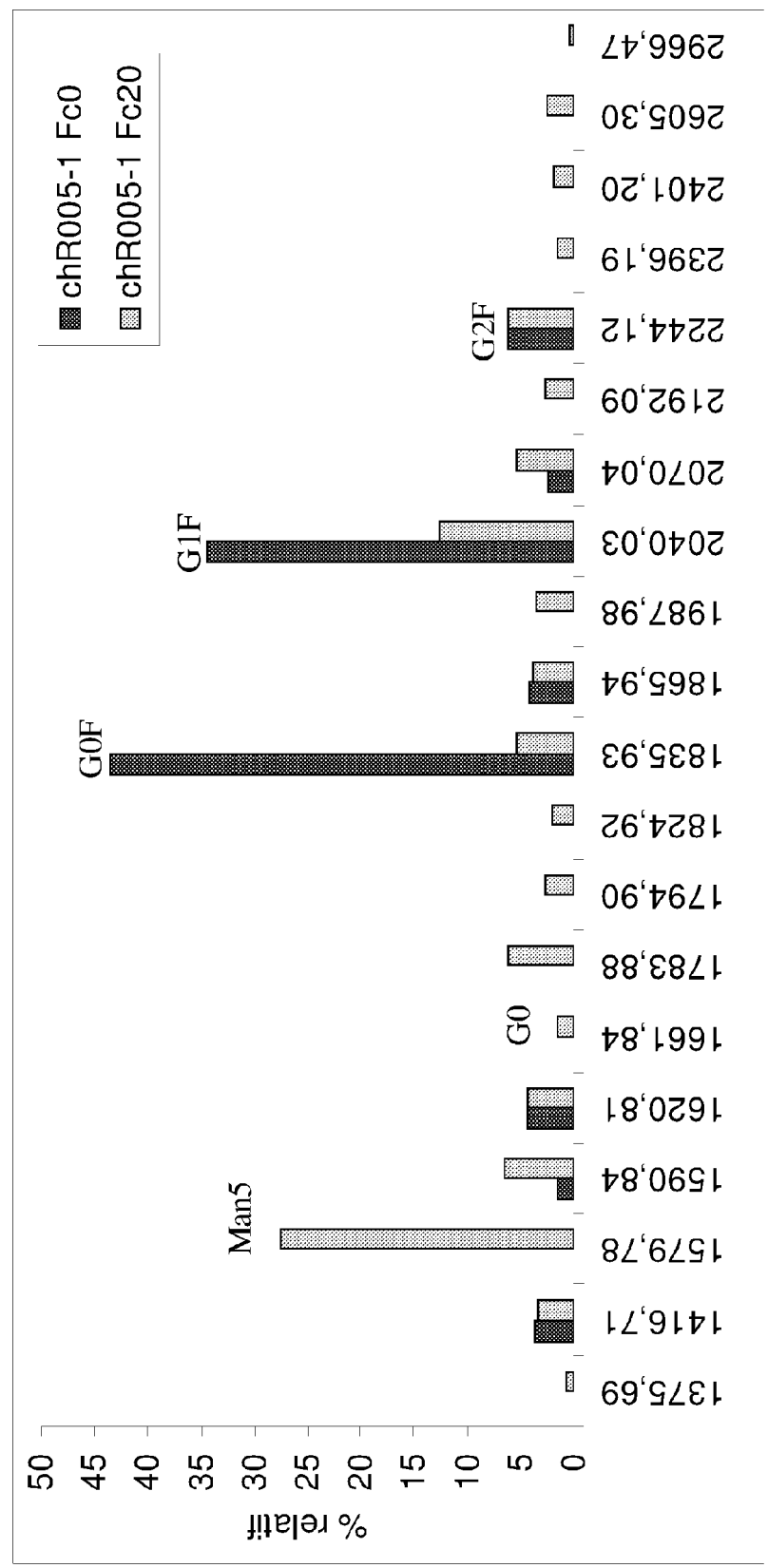

FIG. 27: Oligosaccharide analysis of variants MAbs anti-CD19. Comparison of relative intensities of N-glycan types between the parental chR005-1 Fc0 and the optimized chR005-1 Fc20 MAbs expressed in wild type CHO cells.

Figure 28:
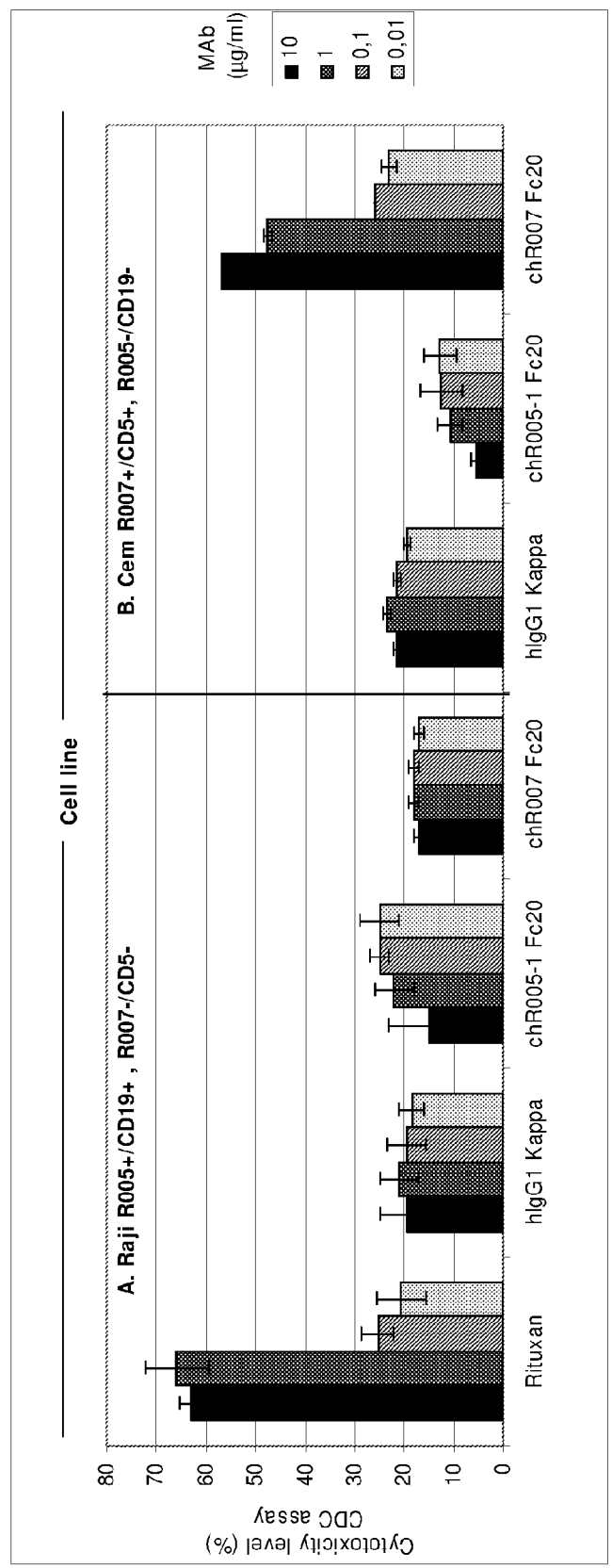

FIG. 28: Differential MAb activity according Fc variant Raji (CD19+, CD5−) and Cem (CD5+ CD19−) cells ($2.10^6$ cells/mL) were incubated with interest MAbs for 20 min at 4° C. Then 5 µl/well of natural human complement was added for 4 hours at 37° C. under shaking condition. After incubation, supernatants were harvested and lactate deshydrogenase (LDH) was measured on fluorometer. CDC lysis level was calculated following the formula: (experimental release−target spontaneous release)/(maximal release−target spontaneous release)*100, where target without natural complement represented spontaneous release. Maximal release value was obtained by treating target cells with Triton X-100. Data represent two independent experiments for Raji and for Cem.

Figure 29:
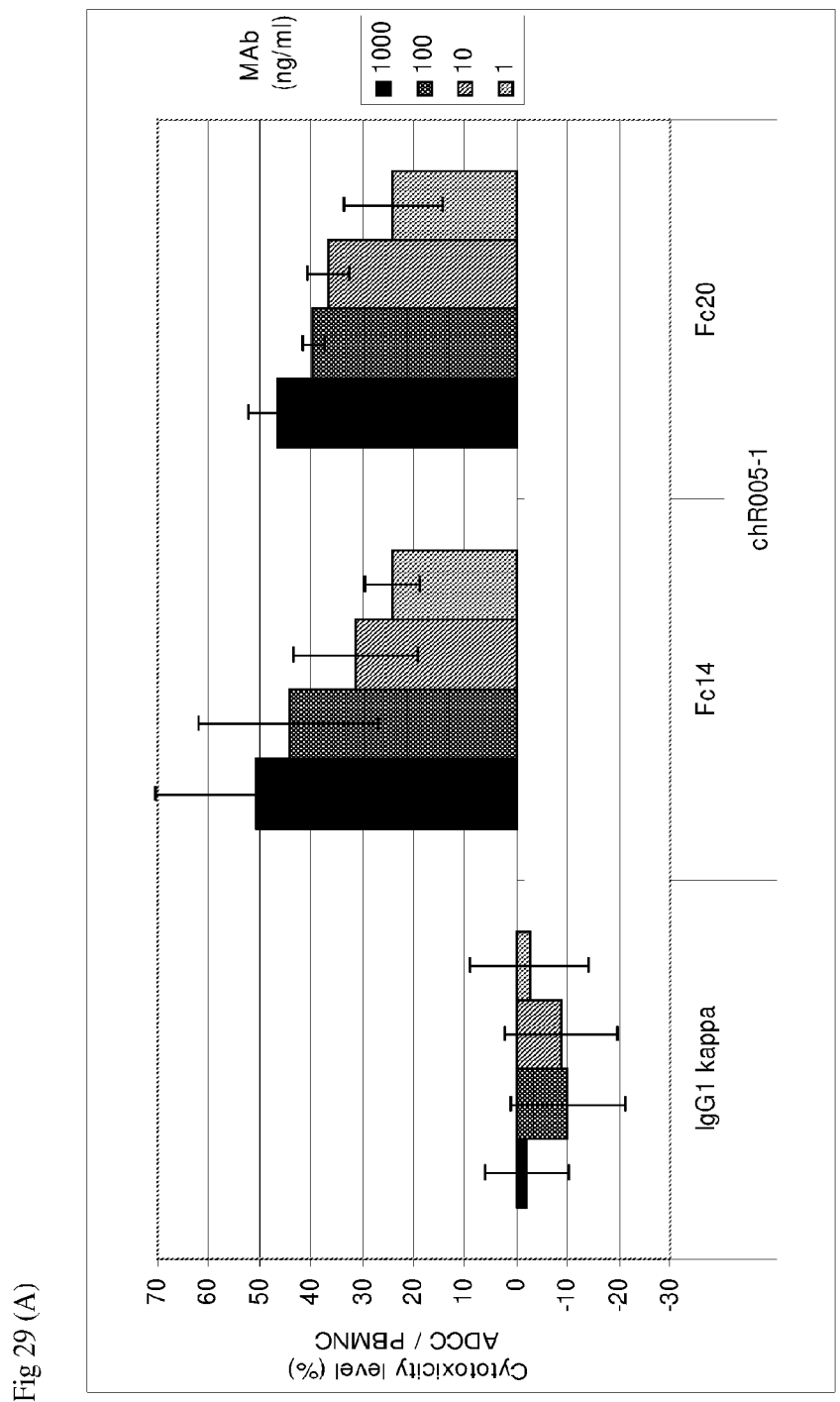
Figure 29:
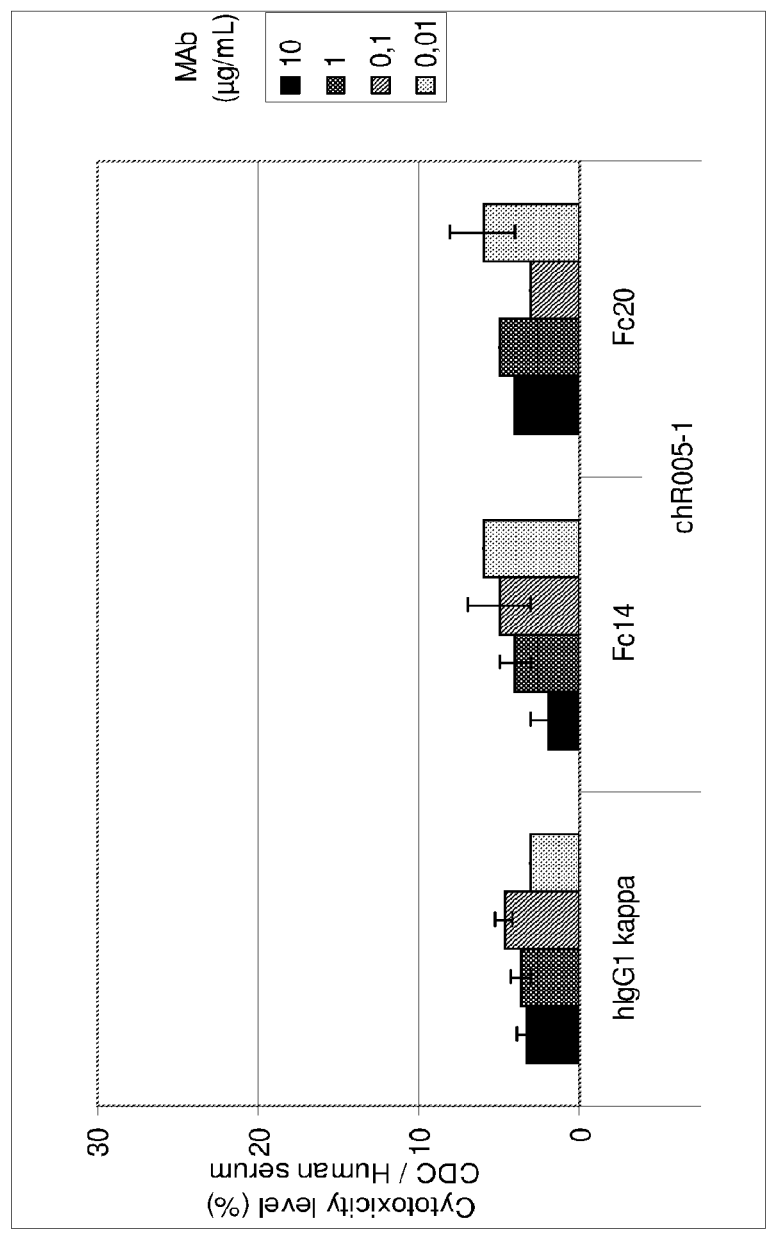
Figure 29:
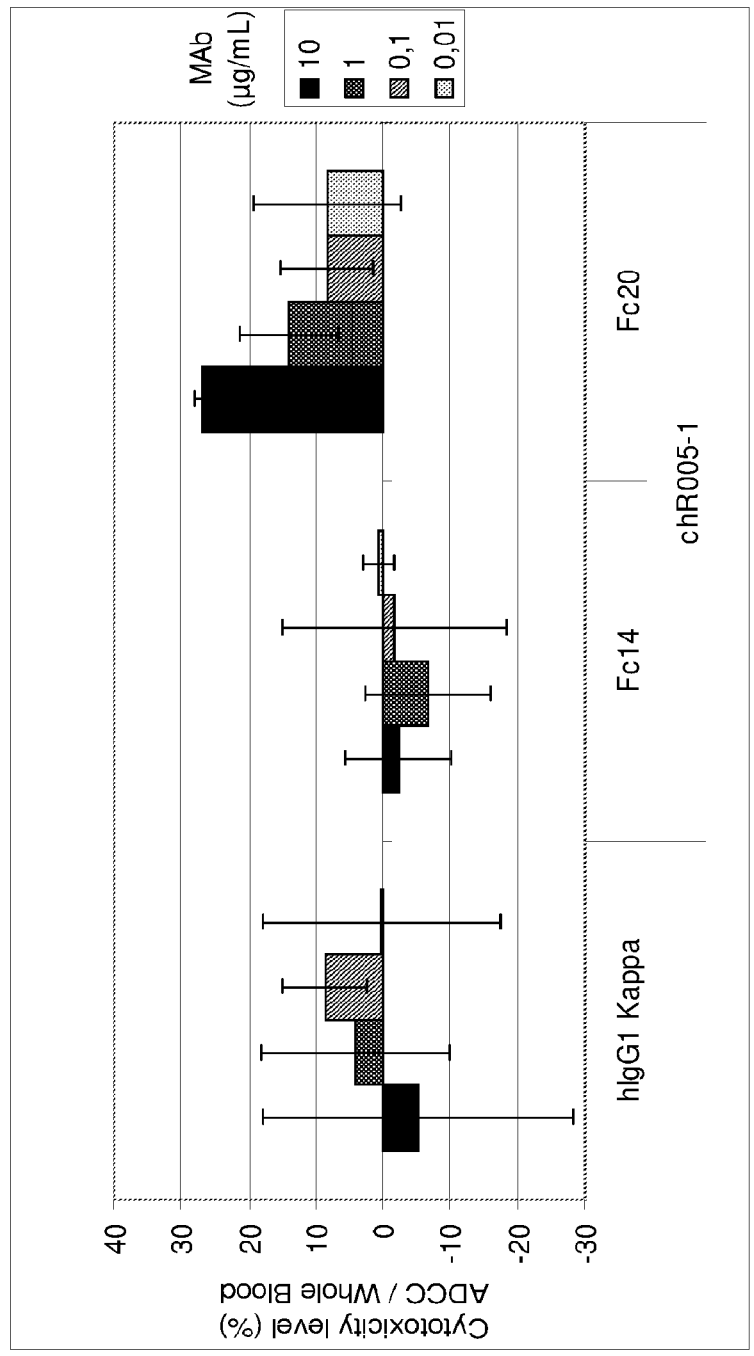

FIG. 29: Differential MAb activity according Fc variant. A—For ADCC MAb activity calcein-AM loaded Raji cells ($1 \times 10^5$ cells/mL) were incubated with interest MAbs for 20 min at 4° C. Effector cells (PBMNC) were added at the ratio E/T 50:1 for 4 hours at 37° C. under shaking condition. After centrifugation, supernatants were harvested and calcein-AM fluorescence was measured on fluorometer. ADCC lysis level was calculated following the formula: [(experimental release−(target+effector spontaneous release))/(maximal release−target spontaneous release)*100]. Maximal release value was obtained by treating target cells with Triton X-100. Data represent mean+/−SD of three independent experiments.
B—For CDC MAb activity Raji cells ($2.10^6$ cells/mL) were incubated with interest MAbs for 20 min at 4° C. Then 5 µl/well of natural human complement was added for 4 hours at 37° C. under shaking condition. After incubation, supernatants were harvested and lactate deshydrogenase (LDH) was measured on fluorometer. CDC lysis level was calculated following the formula: (experimental release−target spontaneous release)/(maximal release−target spontaneous release)*100, where target without natural complement represented spontaneous release. Maximal release value was obtained by treating target cells with Triton X-100. One representative experiment.
C—For ADCC activity on Burkitt's lymphoma cells in the presence of whole blood as effector cells, calcein-AM loaded Raji cells ($1 \times 10^5$ cells/mL) were incubated with interest MAbs for 20 min at 4° C. 50 µl per well of effector cells from whole blood were added for 4 hours at 37° C. under shaking condition. After centrifugation, supernatants were harvested and calcein-AM fluorescence was measured on fluorometer. ADCC lysis level was calculated following the formula: [(experimental release−(target+effector spontaneous release))/(maximal release−target spontaneous release)*100]. Maximal release value was obtained by treating target cells with Triton X-100. Data represent mean+/−SD of three independent experiments.

Figure 30:
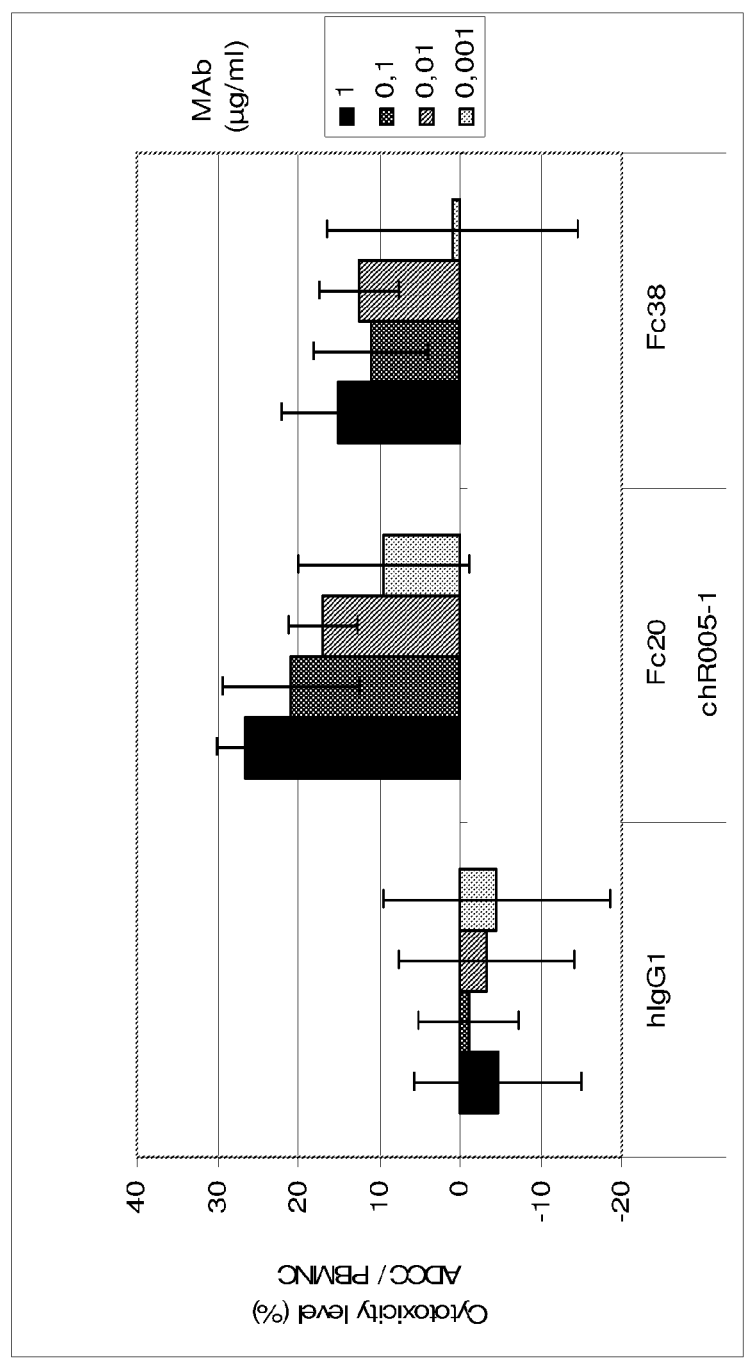

FIG. 30: Differential MAb activity according Fc variant. For ADCC MAb activity, calcein-AM loaded Raji cells ($1 \times 10^5$ cells/mL) were incubated with interest MAbs for 20 min at 4° C. Effector cells (PBMNC) were added at the ratio E/T 50:1 for 4 hours at 37° C. under shaking condition. After centrifugation, supernatants were harvested and calcein-AM fluorescence was measured on fluorometer. ADCC lysis level was calculated following the formula: [(experimental release−(target+effector spontaneous release))/(maximal release−target spontaneous release)*100]. Maximal release value was obtained by treating target cells with Triton X-100. Data represent mean+/−SD of two independent experiments.

Figure 31:
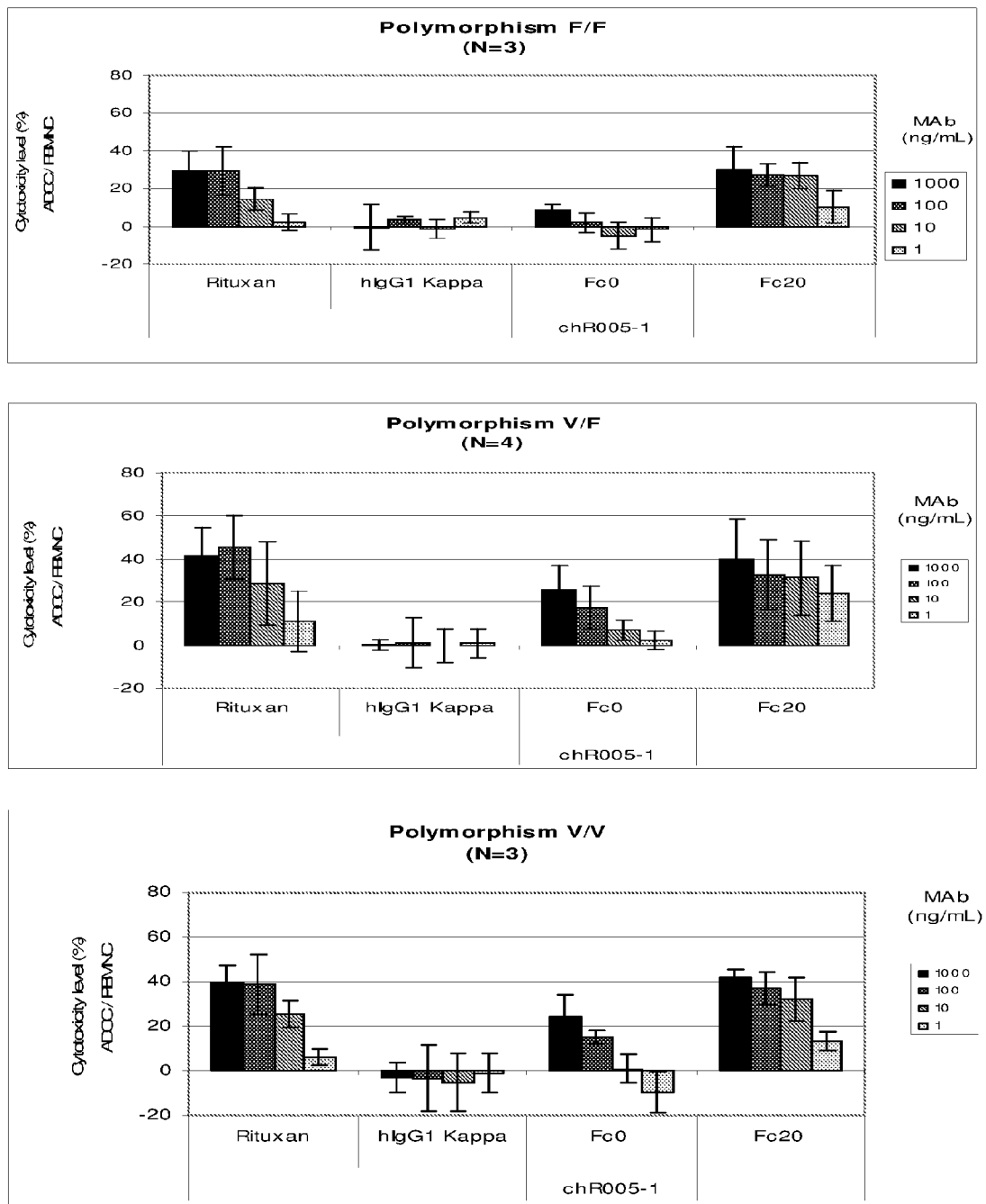

FIG. 31: The Fc engineering abolishes the V/F polymorphism impact on ADCC. Calcein-AM loaded Raji cells ($1 \times 10^5$ cells/mL) were incubated with interest MAbs for 20 min at 4° C. Effector cells (PBMNC) were added at the ratio E/T 50:1 for 4 hours at 37° C. under shaking condition. After centrifugation, supernatants were harvested and calcein-AM fluorescence was measured on fluorometer. ADCC lysis level was calculated following the formula: [(experimental release−(target+effector spontaneous release))/(maximal release−target spontaneous release)*100]. Maximal release value was obtained by treating target cells with Triton X-100. Data represent mean+/−SD of three or four independent experiments.

Figure 32:
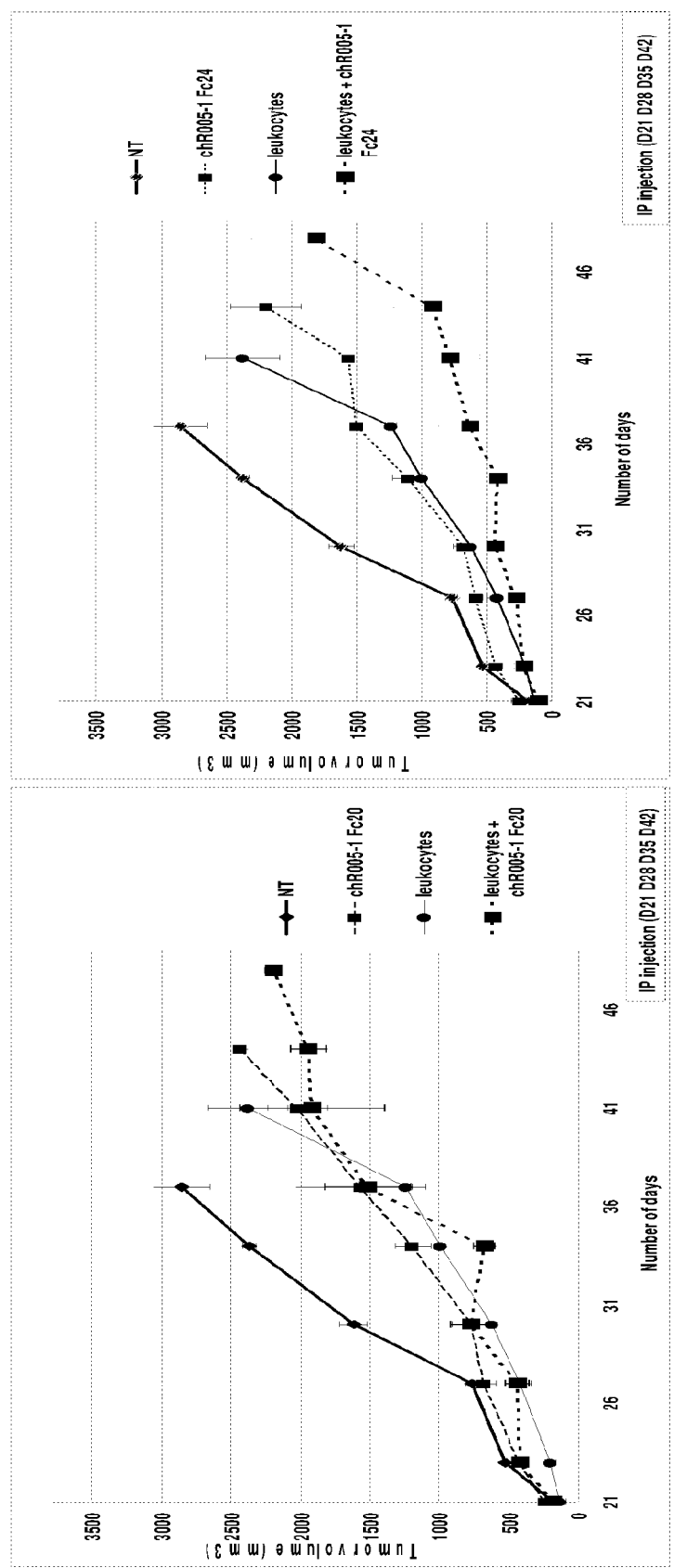

FIG. 32: Inhibition of tumor growth in vivo by the chR005-1 MAb. Mice injected with Raji cells subcutaneously were treated by intravenous MAb infusion once a week starting on day 21 at 100 mg/kg with or without leukocytes. The tumors were measured twice a week.

Figure 33:
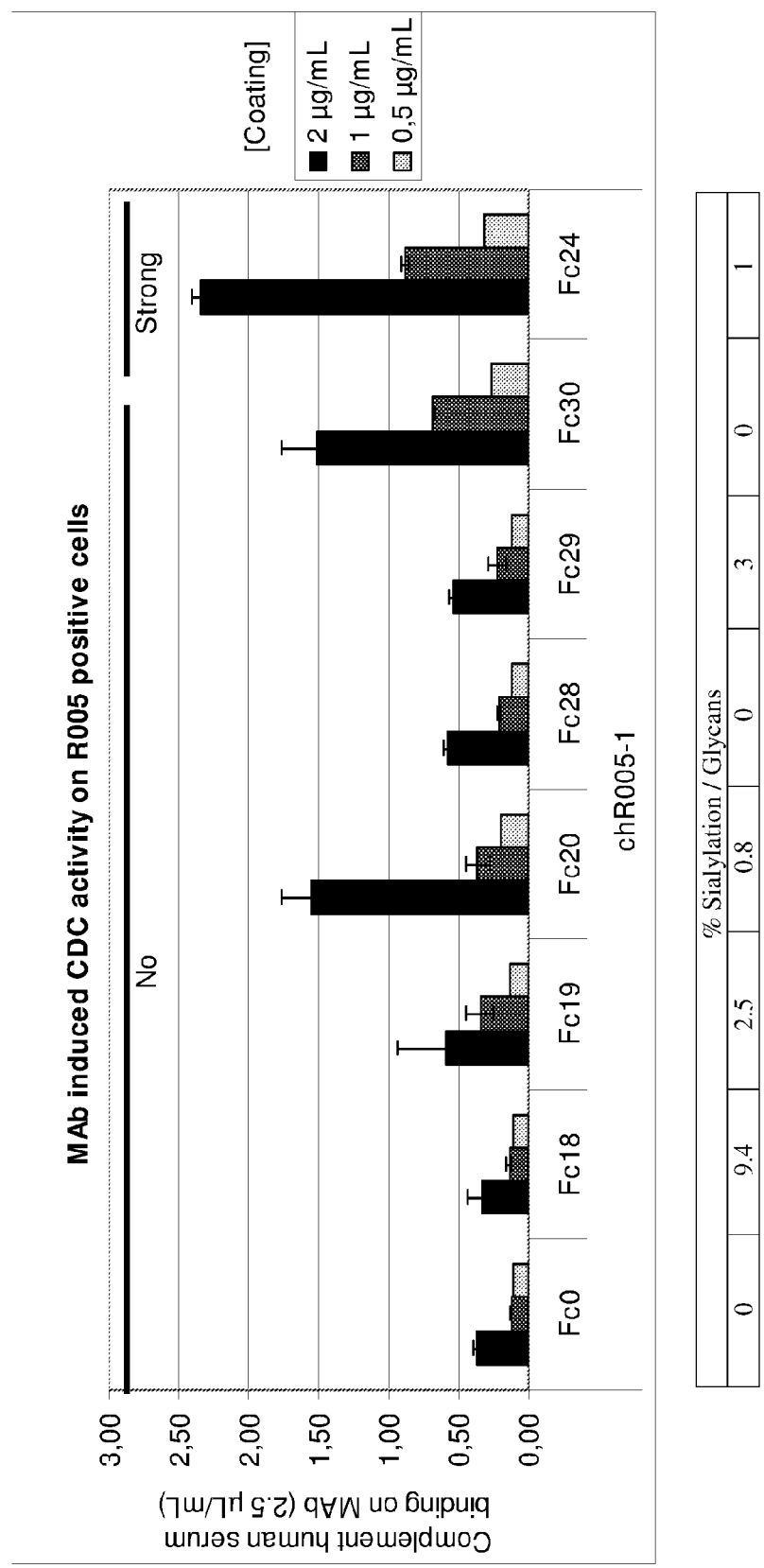

FIG. 33: Complement human serum binding on chR005-1 wild type or mutant MAb. The binding of human complement serum to MAbs was assessed by an ELISA binding assay. The 96-well plates (Nunc) were coated overnight at 4° C. with varying MAb concentrations. After washing, the plates were blocked with PBS-5% BSA for 1 h, and incubated for 1 h with 2.5 µl/well of natural human complement (Sigma). Then, 100 µl/well of a 1/500 dilution of sheep anti-human C1q peroxidase-conjugated Ab (Abd Serotec) added and incubated for 1h. The plates were developed with 100 µl per well of TMB substrate (Uptima Interchim). After $H_2SO_4$ addition, the OD was measured at 450 nm/630 nm using a MRX II microplate reader. Data represent mean+/−SD of two independent experiments.

Figure 34:
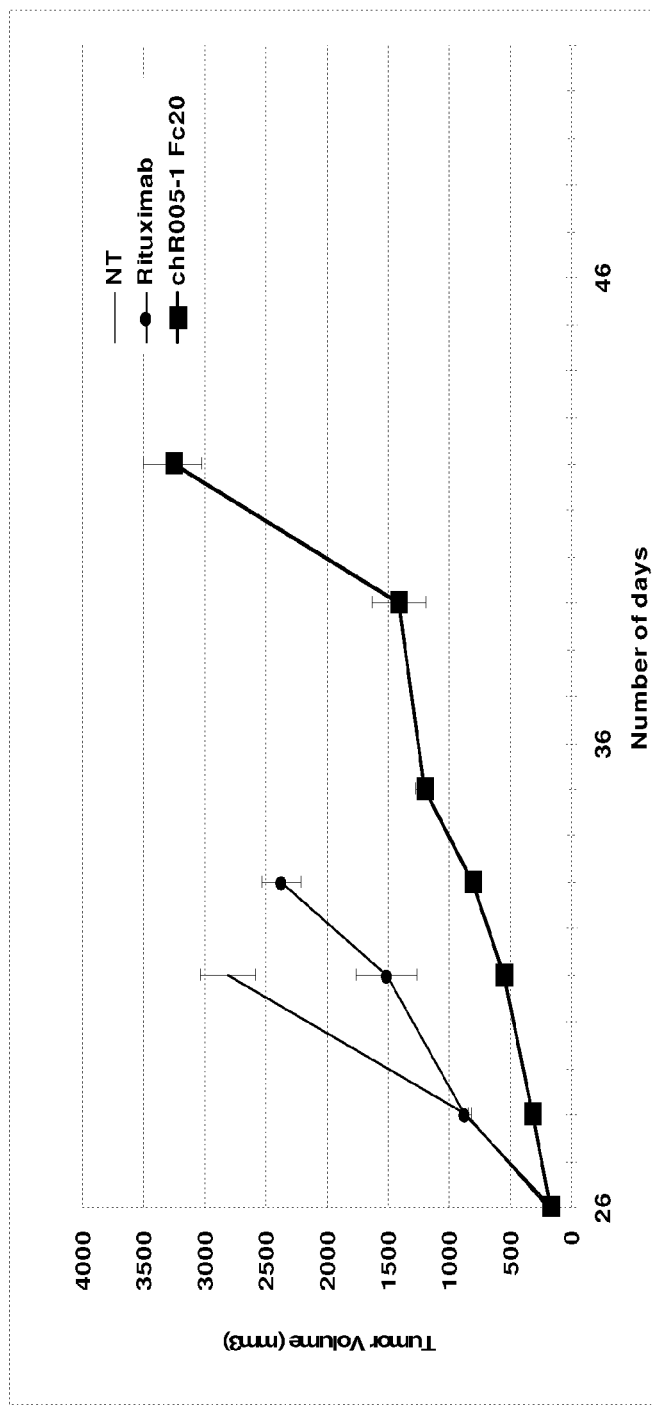

FIG. 34: The growth of Rituxan refractory RL established tumor was inhibited with the Fc20 optimized chR005-1 MAb. Mice injected with refractory Rituxan RL cells subcutaneously were treated by intravenous MAb infusion once a week starting on day 26 at 100 mg/kg.

Figure 35:
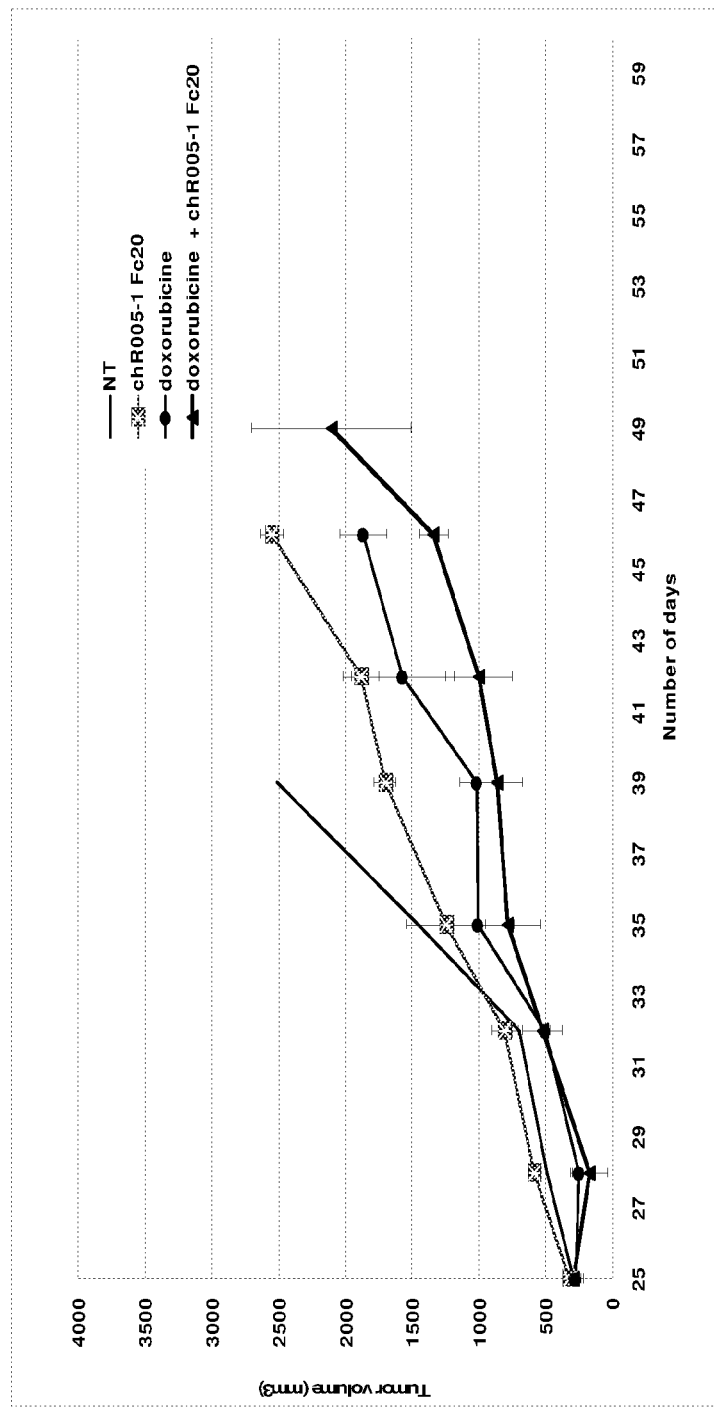

FIG. 35: The combination of the Fc20 optimized chR005-1 MAb and the drug Doxorubicine increased the level of growth inhibition Raji established tumor. Mice bearing established SC Burkitt's lymphoma tumors were treated weekly. The control group received vehicle (NaCl 0.9%) while the treated groups received one of the following: chR005-1 Fc20 MAb 100 mg/kg, doxorubicine 2 mg/kg, chR005-1 Mab (100 mg/kg)+doxorubicine (2 mg/kg).

FIG. 36: IgG N-linked glycans of chR005-1 Fc variant antibodies produced from the wild type CHO Easy C cells. Molecular mass are permethylated glycans, detected as [M+Na]+ by Maldi mass spectrometry (A & B). The MAb panel was produced from CHO Easy C cells. Different glycosylation profiles among the Fc variant antibody panel were observed. One representative experiment.

MATERIALS AND METHODS

Cells: The CHO DG44 cell line was obtained for research purpose from ATCC (American Type Culture Collection, USA). The Burkitt's lymphoma Raji or Daudi cell lines as the T lymphoma Cem cells were obtained from ECACC (European Collection of Cell Culture, UK). Human PBMNCs were purified from leukapheresis of anonymous healthy volunteer donors (Blood Center) using Ficoll-Histopaque density gradient (Sigma). All B-CLL patients enrolled in this study had been defined immunophenotypically as outlined by criteria from the National Cancer Institute Working Group in 1996 (Hallek et al., 2008). Blood was obtained from patients after written informed consent in accordance with the Declaration of Helsinki.

Reagents and antibodies: The IgG1 chimeric negative control was produced at iDD biotech (Dardilly, France). The murine parental MAb mR005-1 or mR005-2 was isolated from iDD biotech hybridoma library. The wild type chR005-1 Fc0 (also called native IgG1) and all the modified antibodies were generated and produced by iDD biotech (Dardilly, France). FITC labelled annexin-V and propidium iodide (PI)

were respectively purchased from BD Biosciences (Pont de Claix, France) and Sigma (Saint Quentin Fallavier, France). Goat Fab' 2 anti-human RPE IgG antibody and Goat anti-mouse FITC Ig antibody were respectively purchased by Sigma (Saint Quentin Fallavier, France) and MP Biomedical (Illkirch, France). Rituxan™/MabThera™ were produced by Genentech and purchased commercially. Others MAbs anti-CD19 4G7 (IgG1), Bu12 (IgG1), HD37 (IgG1), B4 (IgG1) were purchased by Santa Cruz Biotechnology (California, USA), Abd Serotec (Düsseldorf, Germany), Santa Cruz Biotechnology (California, USA), Biogenex (San Ramon, USA).

Murine antibody generation: The Balb/c mice were immunised with CD19 expressing cells such as human chronic lymphoid leukaemia cells. Murine MAbs were generated using standard hybridoma techniques (Zola et al., 1987) and screened initially for their ability to bind by flow cytometry only CD19 positive cell line. Purified MAbs were produced following ascitis purification then purified by using protein-A Sepharose (Pharmacia, Uppsala, Sweden).

Conversion of murine MAb to native chimeric MAb: cDNA corresponding to the variable region of the hybridoma was obtained using two approaches, the first approach consist to the utilisation in PCR of the degenerate N-term amino acid related primer set generate since the N-Terminal sequencing and the second approach consist to the utilisation in PCR of degenerate primer set generate by IMGT® primer database and specific primers previously described (Essono et al., 2003; Wang et al., 2000). The sequence of N-terminal variable region was determined by Edman degradation. Total RNA extraction was carried out using the Tri Reagent kit according to the protocol described by the supplier Sigma. The amplified VL and VH fragments were cloned into the TOPO-TA cloning vector (Invitrogen) for sequence analyses by the dideoxytermination method (Sanger et al., 1977). Then antibody variants constructs were amplified by PCR and cloned into the vector pcDNA3.3 or pMCMVHE.

Construction of antibody variants: Substitutions in the Fc domain were introduced using "megaprimer" method of site-directed mutagenesis (Sarkar et al., 1990). Positions are numbered according to the Kabat® index (Identical V region amino acid sequences and segments of sequences in antibodies of different specificities). Relative contributions of VH and VL genes, minigenes, and complementarity-determining regions to binding of antibody-combining sites were analyzed (Kabat et al., 1991). Heavy and light chain constructs were co-transfected into CHO DG44 (ATCC) suitable for MAb screening. Antibodies were purified using protein A affinity chromatography (GE Healthcare).

CD19 MAb ELISA competition: For competition binding ELISA experiments, cell lysate was used as CD19 antigen source by testing different combination MAbs used as tracer (biotinylated MAb) or as catcher MAb (purified MAb) respectively.

FACS analysis of MAb binding to human CD19: The binding to human CD19 of all MAb generated in the present study were measured with a FACScan (BD Biosciences, Pont de Claix, France) by using the goat anti-mouse FITC Ig from Sigma (Saint Quentin Fallavier, France) for the detection of murine MAbs and with the goat anti-human FITC Ig from Sigma (Saint Quentin Fallavier, France) for the detection of chimeric MAbs. For competition binding experiments, cells were pre-incubated with an excess of either the chR005-1 MAb or the human IgG1 isotype control antibody.

Laser scanning confocal microscopy by using biotinylated antibodies: Cell fluorescence has been visualized using an Inverted Zeiss Axiovert 100M LSM 510 Meta confocal microscope following cell labelling with biotinylated MAbs.

Glycosylation analysis: Release of N-glycans & permethylation were carried out following standard procedures (Ciucanu et al., 1984). Analysis of protein glycosylation was determined by mass spectrometry (Morelle et al., 2007).

Antibody affinity: Determination of antibody KD values was performed as previously described (Benedict et al., 1997) by using binding assay analyzed by flow cytometry (FACS Can, Becton Dickinson, USA) to detect cell-bound antibody.

Assessment of apoptosis by flow cytometry: The apoptosis of cells after incubation with antibodies was measured using annexin V/PI staining followed by FACS analysis. The apoptotic cells were determined in the gate showing a positive staining for annexin V and a negative propidium iodide staining.

Antibody dependent cell cytoxicity Assay (ADCC): Primary B-CLL cells or B-cell lines (Raji) (Target cells) were loaded with 12.5 µM Calcein-AM dye (Sigma, France). $1.10^5$ cells/ml target cells were the pre-incubated with different concentration of interest MAbs and controls for 20 min at 4° C. Effector cells were then added to the target cells at the ratio E/T equal to 50:1. Specific ADCC lysis was calculated using the formula above: (experimental release−(spontaneous release Target+Effector))/(maximal release−spontaneous release target)*100, where target and effector cells without antibody represented spontaneous release. Maximal release value was obtained by treating target cells with Triton X-100.

Complement dependent cytoxicity Assay (CDC): Target cells ($2\text{-}10^6$ cells/ml) either primary B-CLL cells or B-cell lines (Raji, and Daudi cell lines) were incubated with various MAbs concentration. Then, human normal serum were added the culture and then cells were incubated 4 hours at 37° C. under shaking condition. At the end of incubation, lactate deshydrogenase present in supernatant was measured with LDH assay kit (Promega, France). Fluorescence was recorded at the 590 nm excitation wavelength. Specific CDC lysis was calculated using the formula above: (experimental release−target spontaneous release)/(maximal release−target spontaneous release)*100, where target and effector cells without antibody represented spontaneous release. Maximal release value was obtained by treating target cells with Triton X-100.

Results

1. CD19 epitope mapping.

Figure 1:
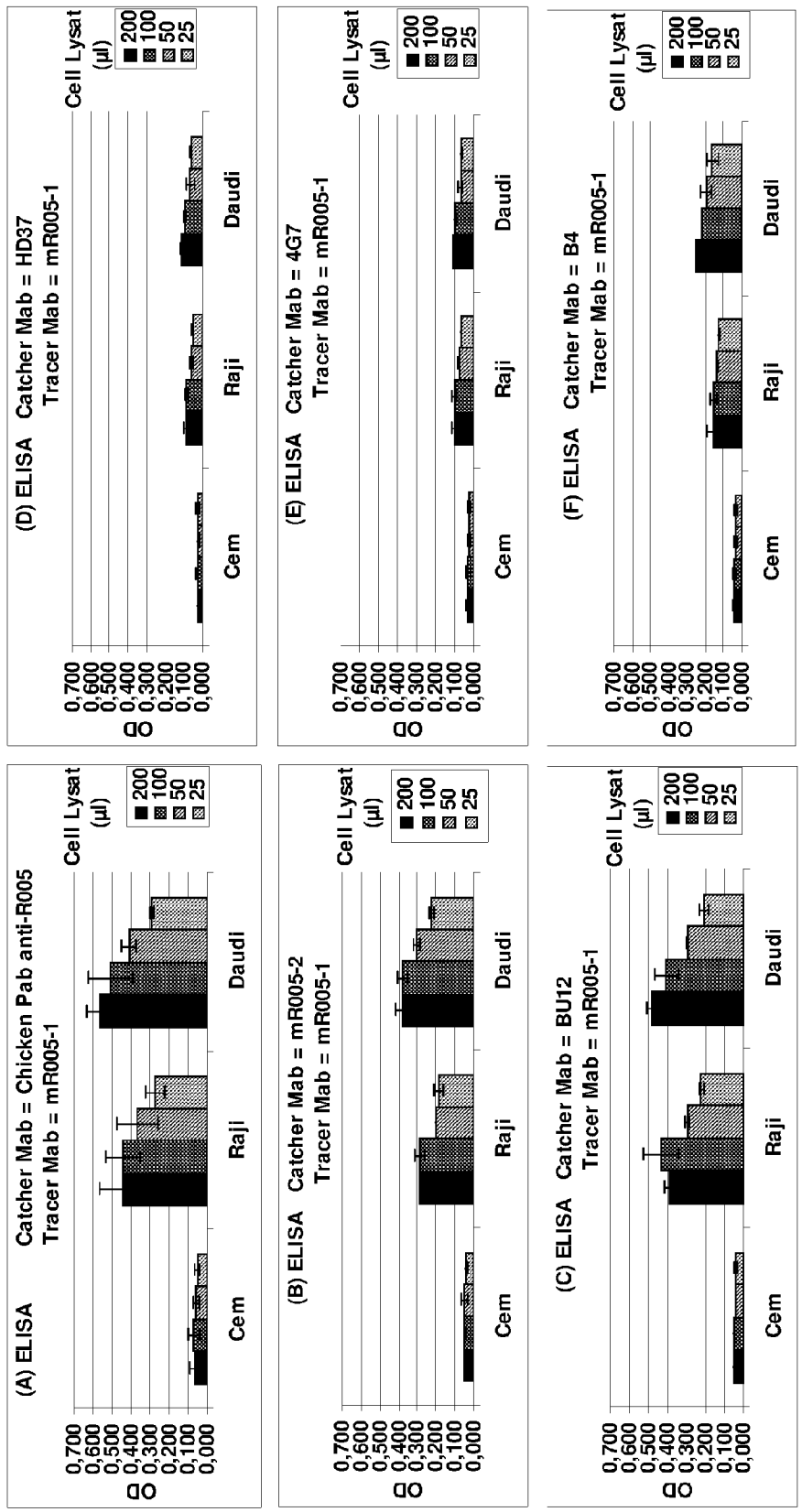
FIG. 1: CD19 epitope mapping. Cell lysate was used as CD19 antigen source by testing different combination MAbs used as tracer (biotinylated MAb) or as catcher MAb (purified MAb) respectively.

By ELISA competition, we determined the CD19 epitope mapping by using a MAb panel anti-CD19 including the MAb mR005-1, mR005-2, 4G7, B4, Bu12, HD37. As shown in FIG. 1, a strong competition was observed by using as tracer/catcher MAbs the combination 4G7/mR005-1 and HD37/mR005-1 revealing that these antibodies recognized the same epitope or an adjacent epitope. By contrast, no significant competition was observed with the mR005-2 or BU12 MAbs.

2. The parental murine MAb mR005-1 triggers apoptosis in Burkitt's lymphoma cell line or in primary CLL cells.

Figure 2:
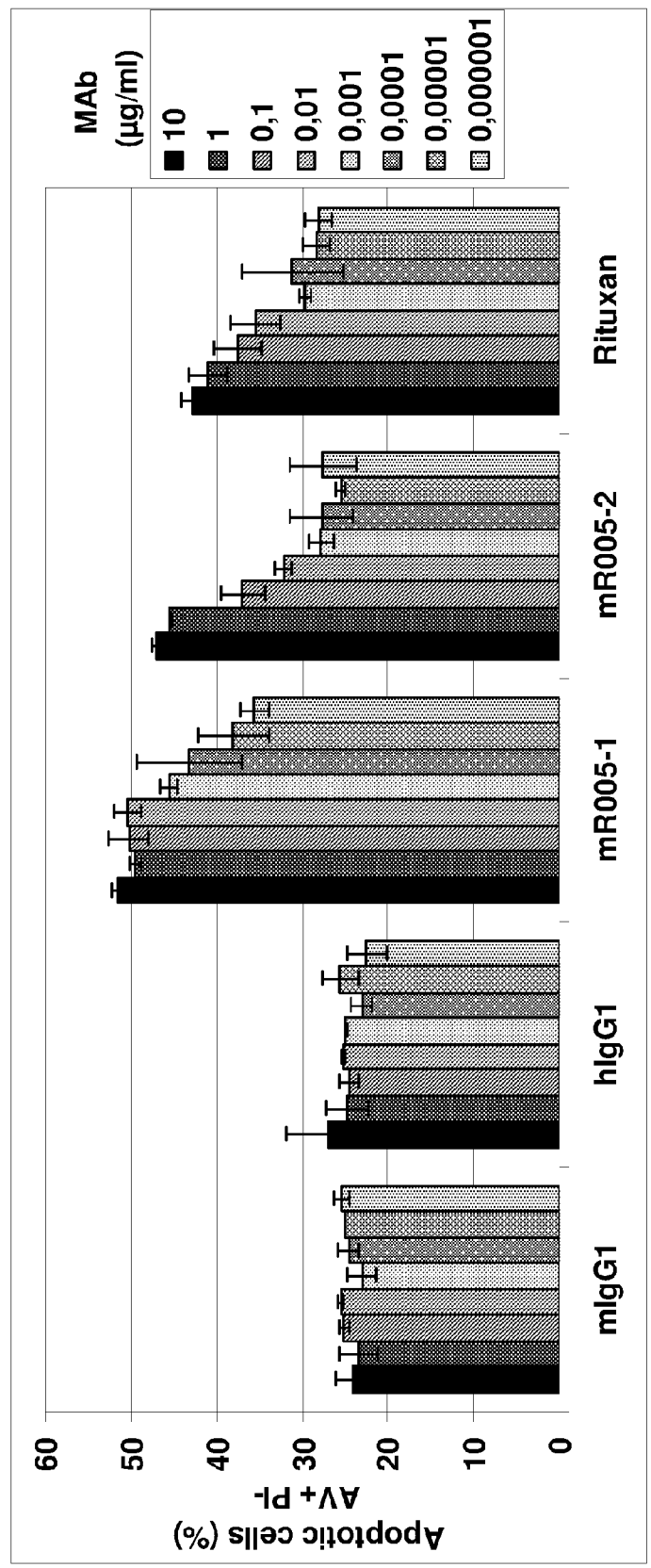
FIG. 2: Higher level of apoptosis with the murine MAb anti-CD19 R005-1 in Burkitt's lymphoma cell line. The Burkitt's lymphoma cell line Raji was incubated with different MAb concentration for 5 hours. B-cells were double-stained with annexin V-FITC and propidium iodide (PI), and analyzed by flow cytometry. Data represent the mean+/−SD of two independent experiments.

The murine MAb mR005-1 was highly effective at inducing PCD than the murine MAb mR005-2 in Burkitt's lymphoma Raji cell line (FIG. 2). It is tempting to suggest that the superior apoptotic effect of the mR005-1 MAb could be related to the fine specificity of these molecules. Our results also demonstrated that the mR005-1 MAb was more efficient to trigger PCD than rituximab.

3. The murine MAb biological activity to trigger apoptosis is linked to epitope on CD19.

Figure 3:
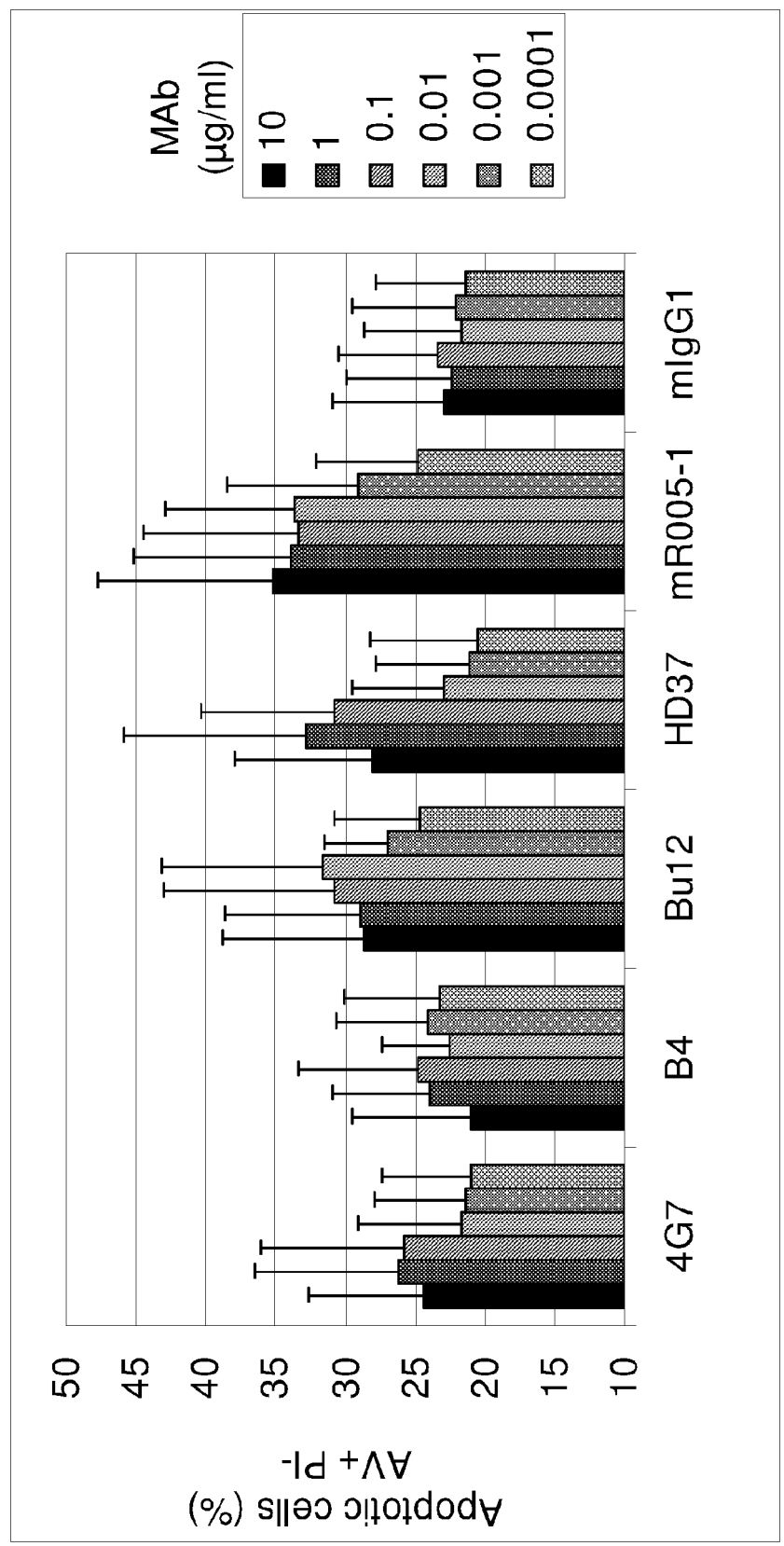
FIG. 3: The murine MAb R005-1 is one of the best inducer of apoptosis in primary B-CLL cells. Primary B-CLL cells were isolated after ficoll centrifugation. $4 \times 10^6$ cells were incubated with interest MAbs and controls for 24 hours at 37° C. in complete media. Then cells were harvested and stained with Annexin-V FITC/Propidium Iodide. Apoptotic cells were defined as annexin $V^+/PI^-$ cells. Data represents the mean+/−SD of five independent experiments.

A panel of murine MAb against human CD19 was tested to evaluate the apoptotic potential of various clones. We used the annexin-V/PI approach to determine the level of apoptosis induced by these antibodies at 24 hours post incubation. We have found that mR005-1 is one of the best MAbs as inducer of apoptotic process in B-CLL cells isolated from patients (FIG. 3). Similar data was observed by using the Burkitt's lymphoma cell line (data not shown). Our observations presented here suggest that treatment of B-CLL tumor cells with derivated chimeric MAb related to the mR005-1 MAb, which are capable of inducing an apoptotic signal, may contribute to their direct killing and elimination.

4. Chimerisation of the murine MAb R005-1 and of the murine MAb R005-2.

Figure 4:
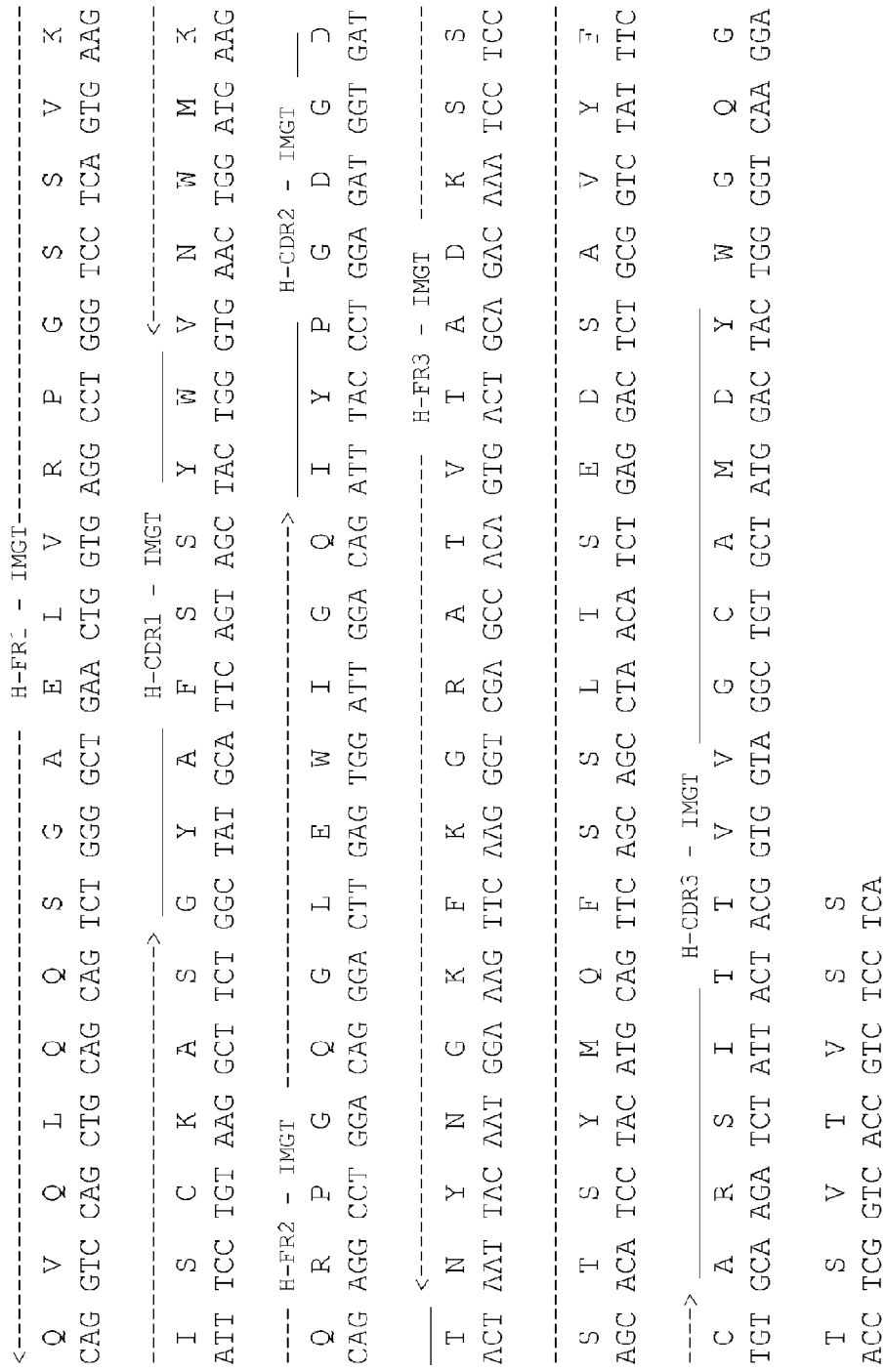
FIG. 4: The nucleotide and amino acids sequences of the mR005-1 or mR005-2 MAbs, (A): $V_H$ (B): VL Amino acids are shown as one-letter codes.
Figure 4:
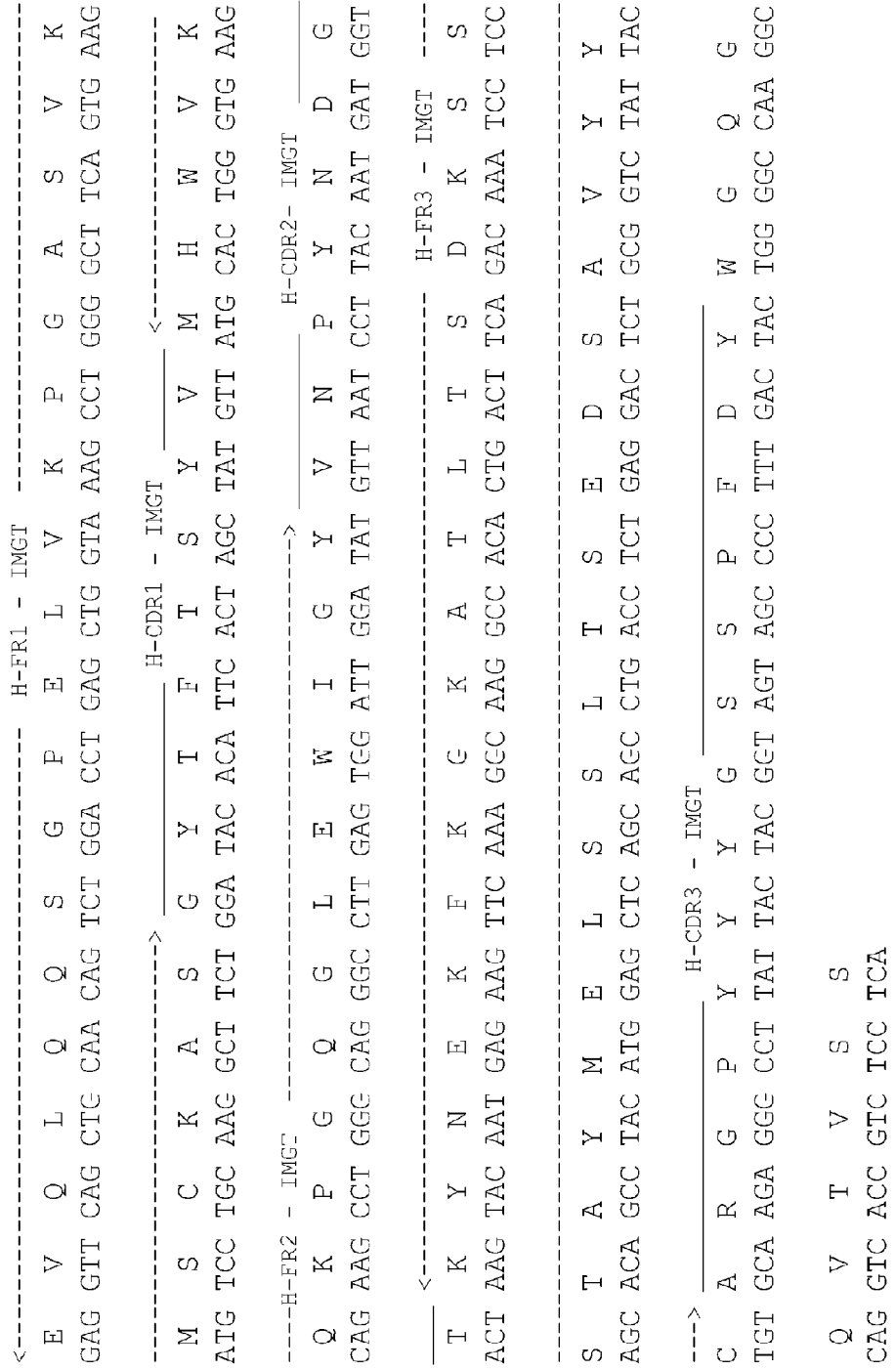

In comparison with the IMGT® database, the sequence of VL mR005-1 and the sequence of VH mR005-1 were validated recognizing at least 96% and at least 98% respectively (FIG. 4). The sequences of VL mR005-2 and VH mR005-2 were also validated (99% and 98%, respectively). The authenticity of the VH and VL sequences obtained by cDNA cloning were also confirmed by N-terminal amino acid sequencing of the target mouse monoclonal antibody. Heavy and light chains were separated before amino acid sequencing by polyacrylamide gel electrophoresis under reducing conditions and the 20 first amino were sequencing by Edman degradation. Then sequences were then cloned in the Light chain expression vector (L chR005-1 or L chR005-2) and in the Heavy MAb expression vectors (H chR005-1 or H mR005-2) encoding also for a native Fc region named Fc0. Transient transfection on CHO dhfr$^{-/-}$ cells by lipofection was performed.

5. Authenticity and selection of VH and VL chains confirmed by flow cytometry analysis.

The native chimeric MAb chR005-1 Fc0 constructed from the VH and VL sequences was compared directly with the parental murine MAb mR005-1 for staining and specificity. As shown in FIG. 5, comparable staining was observed on peripheral blood lymphocytes. Cell binding competition between the murine parental mR005-1 and the native chR005-1 Fc0 was also showed in FIG. 6. The chR005-1 Fc0 MAb completely blocked the murine parental mR005-1 MAb binding.

6. The induction of CD19 internalization following MAb binding is not a general effect and could be related to the different MAb anti-CD19 used.

By an indirect staining in flow cytometry, the presence or not of the naked antibody at B-CLL cell surface following incubation at 4° C. or at 37° C. was determined (FIG. 7). A significant shift of geometric mean fluorescence intensity was observed with rituximab at 37° C. for an extended time period beyond 3 or 24 hours. Similar effect was noticed with the parental murine MAb mR005-1, although a lower modulation of geometric mean fluorescence intensity was observed with the wild type chimeric MAb chR005-1 Fc0.

7. Characterization of the native chR005-1 Fc0 cytotoxicity activity.

In many applications, chimeric antibodies have demonstrated improved effector function in complement-mediated tumor cells lysis and in antibody-dependent cellular cytotoxicity assays as compared to the parental murine monoclonal antibody (Liu et al., 1987; Nishimura et al., 1987; Hamada et al., 1990). The native chimeric MAb chR005-1 Fc0 induced modest ADCC against Burkitt's lymphoma cell line (FIG. 8) or against ex vivo B-CLL cells from patients (FIG. 9). In a standard cytotoxicity assay complement dependent, only rituximab used as positive control killed the Raji cells, whereas the chR005-1 Fc0 failed to trigger cell cytotoxicity (FIG. 10).

8. Generation of variants for human IgG1 $C_H2$ domain.

As used herein, the term "heavy chain" is used to define the heavy chain of an IgG antibody. In an intact, native IgG, the heavy chain comprises the immunoglobulin domains VH, CH1, Hinge, CH2 and CH3. Throughout the present specification, the numbering of the residues in an IgG heavy chain is that of the EU index as in Kabat et al, (1991), expressly incorporated herein by references. The "EU index as in Kabat" refers to the numbering of the human IgG1 EU antibody.

We constructed several variants including single, double, three, four or five substitution variants to enhance ability to mediate effector function, (FIG. 11).

9. Only some mutations on Fc engineering enhance ADCC.

The MAb activity to mediate ADCC from the MAb variant panel was measured using Raji or Daudi target cells firstly in PBMNC based assays (FIG. 12). The variant F243L/R292P/Y300L/V305L/P396L named chR005-1 Fc20 was chosen as the variant with the greatest ADCC activity.

The activity of chR005-1 Fc20 was also assessed by using ex vivo B-CLL cells from patients (FIG. 13). Similar to observations with ADCC on Raji cell line, the potency and efficacy of the chR005-1 Fc20 MAb was notably higher when compared to parental chR005-1 Fc0.

10. Investigation on the MAb variant panel to CDC using B-cell lymphoma.

As shown in FIG. 14, the five mutants F243L/R292P/Y300L/V305L/P396L did not induced CDC using the Raji cell line. Similar results were observed when targeting ex vivo B-CLL (FIG. 15).

11. The MAb variants triggered similar level of cell apoptosis.

The biological activity on programmed cell death of the parental chR005-1 Fc0 and the chR005-1 Fc20 MAb were compared on Raji CD19 positive cell line (FIG. 16) or on ex vivo B-CLL (FIG. 17). No difference of MAb triggered PCD was observed between the MAb lead chR005-1 Fc20 and its parental chR005-1 Fc0.

12. The optimized chimeric chR005-1 Fc20 antibody did redistribute into patches on the cell surface and did not internalize.

Following binding of biotinylated conjugated CD19 antibodies revealed with Alexa Fluor 488, the analysis by confocal microscopy confirmed that cells expressed still on the cell surface the CD19 target detected with the murine parental MAb mR005-1 or with the chimeric wild type chR005-1 Fc0 or chR005-1 Fc20 (Data not shown). Similar effect was observed following rituximab binding. The chR005-1 Fc0 or chR005-1 Fc20 MAbs also induced a dynamic modulation on cell surface just after binding their antigen but were still available for cell killing mechanism. This specific property for MAb(s) related to the parental mR005-1 MAb will be useful to initiate cell cytotoxicity induced either by complement or by effector cells e.g. NK cells.

13. Monoclonal antibodies may be used in combination.

The MAb activity to mediate PCD alone or in combination was compared using Daudi target cells or on ex vivo B-CLL (FIG. 18, FIG. 19). A higher level of apoptotic cells was observed in the presence of the murine parental mR005-1 combined with rituximab demonstrated the feasibility and the benefit of the MAb combination.

The combination of the MAb chR005-1 Fc20 with rituximab enhanced also the apoptosis level using Daudi target cells or on ex vivo B-CLL (FIG. 20, FIG. 21).

14. The MAb directed against CD19 can be used in patient with rituximab recurrent and refractory disease.

Ex vivo B-CLL samples from patients with recurrent and refractory disease following rituximab treatment were treated in vitro with the murine parental mR005-1 (FIG. 22) or with the MAb chR005-1 Fc20 (FIG. 23). The higher level of apoptosis observed with MAbs against CD19 compared with rituximab demonstrated the feasibility and the efficacy to use MAbs directed another antigen than CD20.

15. Generation of low fucosylated anti-CD19 MAb chR005-1 F20.

The sugar core found in the Fc region of IgG is a bi-antennary complex [Asn297-GN-GN-M-(M-GN)2] where GN is N-acetylglucosamine, and M is mannose. Oligosaccharides can contain zero (G0), one (G1) or two (G2) galactose (G). Variations of IgG glycosylation patterns can include core fucosylation (F). As shown in FIG. 24, the three major peaks in the chR005-1 Fc0 sample correspond to masses of fucosylated oligosaccharides with (GlcNAc)2 (Fuc)1+(Man)3 (GlcNAc)2 (m/z 1836), (Gal)1 (GlcNAc)2 (Fuc)1+(Man)3 (GlcNAc)2 (m/z 2040) and (Gal)2 (GlcNAc)2 (Fuc)1+(Man) 3(GlcNAc)2 (m/z 2245). By contrast, as shown in FIG. 25, the two peaks G0F and G1F were present at much lower levels in the chR005-1 Fc20 antibody (5.4% and 12.6% respectively) compared to the native chR005-1 Fc0 (43.6% and 34.5% respectively). No impact was observed on the peak G2F. A higher level of oligomannoses between $(Man)_5(GlcNAc)_2$ (m/z 1579), $(Man)_6(GlcNAc)_2$ (m/z 1784) $(Man)_7(GlcNAc)_2$ (m/z 1988), (Man)8(GlcNAc)2 (m/z 2192) and (Man)9 (GlcNAc)2 (m/z 2396) was observed (41.6% versus 0%) as also a higher level of sialylated glycoforms (4.6% versus 0%) including (Gal)1 $(GlcNAc)_2$ $(Fuc)_1$ $(NeuAc)_1$+$(Man)_3$ $(GlcNAc)_2$. (m/z 2401), (Gal)2 $(GlcNAc)_2$ $(Fuc)_1$ $(NeuAc)_1$+ $(Man)_3(GlcNAc)_2$. (m/z 2605) and (Gal)3 $(GlcNAc)_2$ $(Fuc)_1$ $(NeuAc)_1$+$(Man)_3(GlcNAc)_2$. (m/z 2966) in the chR005-1 Fc20 antibody compared to the native chR005-1 Fc0.

As shown in FIG. 27, data demonstrated accumulation of non-fucosylated in the optimized antibody from the chR005-1 Fc20 instead of fucosylated structures in the native chimeric chR005-1 Fc0 antibody.

16. Determination of the binding MAb affinity.

The binding properties of the MAbs mR005-1, chR005-1 Fc0 or chR005-1 Fc20 were examined by flow cytometry analysis and binding equilibrium studies on CD19 positive Raji cell line. Therefore neither the chimerization nor MAb optimization resulted in significant changes in MAb affinity:

| MAb | KD nM |
| --- | --- |
| mR005-1 | 2.82 |
| chR005-1 Fc0 | 0.79 |
| chR005-1 Fc20 | 0.67 |

17. FIG. 28 shows the CDC ability of two unrelated antibodies comprising the Fc20 optimized variant (chR005-1 Fc20 anti-CD19 MAb or chR007 Fc20 MAb which is an antibody directed against CD16A). It appears that the Fc mutations according to the invention are suitable and specific for the anti-CD19.

18. Differential MAb activity according to the Fc variant

FIG. 29 shows different Fc variant anti-CD19 antibodies (Fc14, Fc20) and their ability to trigger CDC and/or ADCC with isolated PBMNC or in the presence of whole blood.

The comparison with the Fc24 shows the specificity of the Fc20 mutations to yield ADCC function and no CDC function. The Fc14 comprises the mutations proposed by Xencor.in an anti-CD19 antibody. These mutations are not suited to an anti-CD19.

19. Differential MAb activity according to the Fc variant.

FIG. 30 shows different Fc variant anti-CD19 antibodies (Fc20, Fc38) and their ability to trigger ADCC with isolated PBMNC. The V305L mutation versus V305I impacts the ADCC level. The V305L mutation is preferred.

20. The Fc engineering abolishes the V/F polymorphism impact on ADCC.

FIG. 31 shows the ADCC triggered with the chR005-1 Fc20 MAb in the presence of effectors cells with different V/F polymorphism. The invention includes, in one aspect, a method of enhancing the ADCC or an anti-CD19 specific antibody with an increased affinity for both Fc gamma RIIIa-Phe158 and Fc gamma RIIIa-Val158 receptors as well as enhanced effector cell function.

21. The invention includes, that the improved ADCC with the chR005-1 Fc20 was not limited in CD16A off rates.

FIG. 32 shows in vivo comparative effect of the chR005-1 MAb Fc20 or Fc24 optimized variant on tumour clearance in established mouse Raji lymphoma xenograft model with or without human leukocytes inoculation. The invention includes, that the improved ADCC with the chR005-1 Fc20 was not limited in CD16A off rates.

22. Impact of sialylation on CDC ability.

FIG. 33 shows that the modification at position 243 leading additional sialylation was not enough sufficient to restore recognition target cell lysis by complement. The present invention reveals that only the chR005-1 Fc24 which exhibits a similar chR005-1 Fc20 sialylated glycoform pattern but with a different protein sequence and a higher level of bound complement induced a target cell lysis by complement.

23. Impact of the MAb anti-CD19 on Rituxan refractory follicular lymphoma.

FIG. 34 shows that the growth of Rituxan refractory RL established tumour was inhibited with the Fc20 optimized chR005-1 MAb.

24. Influence of MAb and drug combination.

FIG. 35 shows that the combination of the Fc20 optimized chR005-1 MAb and the drug Doxorubicine increased the level of growth inhibition Raji established tumor.

25. Specific patterns of glycans related to Fc optimized domain.

FIG. 36 shows the glycan profils of each Fc variant.

REFERENCES

Awan F T et al., 2010. Blood. 115(6):1204-13.
Bannerji R et al., 2003. Clin Oncol. 15; 21(8):1466-71.
Bargou R, et al., 2008. Science. 321:974-7.
Benedict C A et al., 1997. Immunol Methods. 28; 201(2):223-31.
Bienvenu J et al., 2001. Hematol J. 2(6):378-84.
Boyd P N, Lines A C, Patel A K., 1995. Mol Immunol. 32(17-18):1311-8.
Bruenke J et al., 2005. Br J Haematol. 130(2):218-28.
Cartron G et al., Blood. 2002 February 1; 99(3):754-8.
Ciucanu I. & Kerek, F., 1984. Carbohydr. Res. 131, 209-217.
Essono S et al., 2003. J Immunol Methods. 279(1-2):251-66.
Genet., 1986., Somatic Cell Mol. 12, 51.
Hamada H et al., 1990. Cancer Res. 50(11):3167-71.
Hallek M et al., 2008 December Blood. 15; 112(13):5259. PMID: 18216293
Hekman A et al., 1991. Cancer Immunol Immunother 32:364-72
Horton H, et al., Cancer Research, vol. 68, no. 19, October 2008 (2008-10), pages 8049-8057.
Jassal R, et al., Biochemical and Biophysicam research communication, Academic Press Inc, Orlando. Fla., US, vol. 286, no. 2, 17 Aug. 2001 (2001-08-17), pages 243-249
Jenkins et al., 1996 August. Nat Biotechnol. 14(8):975-81
Kabat E A, Wu T T., 1991. J Immunol. 147(5):1709-19
Kabat E A et al. 1991. Maryland: US Department of health and human services, NIH.

Katsutaka Nagai et al., 1993. Glycobiology series 2—Destiny of Sugar Chain in Cell.
Kyte J, Doolittle R F., 1982 May. J Mol Biol. 5; 157(1):105-32.
Kirschfink M., 2001 April. Immunol Rev. 180:177-89. Review. PMID: 11414360.
Kumpel B M et al., 1994. Hum Antibodies Hybridomas. 5(3-4):143-51. PMID: 7756579.
Leatherbarrow R J, Dwek R A., 1990 November. Mol Immunol. 27(11):1145-53.
Li Y et al., 2007 September. J Immunol. 15; 179(6):4263-71.
Lifely M R et al., 1995 December. Glycobiology. 5(8):813-22. PMID: 8720080.
Liu A Y et al., 1987. Proc Natl Acad Sci USA. 84(10):3439-43.
Liu A Y et al., 1987. J Immunol. 139(10):3521-6.
Lund J et al., 1995 December. Mol Immunol. 32(17-18):1311-8.
Lund J, et al., Journal of Immunology vol. 157, no. 11, 1996, pages 4963-4969.
Mlhj M et al., 2007. Mol Immunol. 44(8):1935-43.
Morelle, W & Michalski J-C. 2007., Nature protocols, vol 2, N°7, 1585-1602.
Nishimura Y et al. 1987., Cancer Res. 47(4):999-1005.
Olejniczak S H et al. FEBS Lett., 1983 December. 12; 164 (2):227-30.
Press O W et al. 1989., Cancer Res 49:4906-12.
Pina M Cardarelli et al., Cancer Immunology Immunotherapy vol. 59, no. 2, 2009, p 257-265.
Rowland A J, Pietersz G A, McKenzie I F., 1993. Cancer Immunol Immunother. 37(3):195-202.
Sanger F, Nicklen S, Coulson A R., 1977. Proc Natl Acad Sci USA. 74(12):5463-7.
Sapra P, Allen T M. 2002., Cancer Res 62: 7190-4.
Sarkar G, Sommer S S., 1990. Biotechniques. 8(4):404-7.
Sato S, Jansen P J, Tedder T F., 1997. Proc Natl Acad Sci USA. 94(24):13158-62.
Sato S et al., 1997. J Immunol. 159(7):3278-87.
Shields R. L et al., 2002. *J Biol Chem.* 277, pp. 26733-26740.
Stavenhagen J, et al., Cancer Research, vol. 67, no. 18, 2007, 8882-8890.
Treon S P et al., 2001 May-June. J Immunother. 24(3):263-71.PMID: 11394505.
Van der Kolk L E et al., 2001 December. Br J Haematol. 115(4):807-11.
Vlasveld L T et al., 1995. Cancer Immunol Immunother. 40:37-47.
Wang Z, Raifu M et al., 2000. J Immunol Methods. 233(1-2):167-77.
Wang S Y et al., 2008 February. Blood. 1; 111(3):1456-63.
Weng W K, Levy R., 2001 September. Blood. 1; 98(5):1352-7.PMID: 11520782.
Winkler U, et al., 1999 October. Blood. 1; 94(7):2217-24.
Zola H., Monoclonal antibodies: a manual of techniques. 1987. (ed) CRC press, Boca Raton Fla.

The invention claimed is:

1. An anti-CD19 antibody modified to comprise a variant human IgG Fc region, wherein this variant region comprises an amino acid substitution at each of the amino acid positions 243, 292, 300, 305 and 396 of the human IgG Fc region, with the proviso that position 326 or 333 or both positions 326 and 333 are not substituted, wherein the numbering of the amino acid residues in the Fc region is the one of Kabat, and wherein the antibody has been produced in wild-type rodent cells, wherein the antibody recognizes a non-internalizing epitope on the CD19 antigen, and wherein the antibody comprises the CDRs of the antibodies mR005-1 or mR005-2 whose amino acid sequences are depicted on the following table:

|  | Amino acid sequence VH | Amino acid sequence VL |
| --- | --- | --- |
| mR005-1 | SEQ ID NO: 27 | SEQ ID NO: 29 |
| mR005-2 | SEQ ID NO: 31 | SEQ ID NO: 33. |

2. The antibody of claim 1, which comprises an Fc region comprising substitution at position 243 with Leucine (L), at position 292 with Proline (P), at position 300 with Leucine (L), at position 305 with Leucine (L) and at position 396 with Leucine.

3. The antibody of claim 1, which comprises an Fc region comprising substitution at position 243 with Leucine (L), at position 292 with Proline (P), at position 300 with Leucine (L), at position 305 with Isoleucine (I) and at position 396 with Leucine.

4. The antibody of claim 1, which has one or two Fc with no $(GlcNAc)_2(Fuc)_1+(Man)_3(GlcNAc)_2$ glycan.

5. The antibody of claim 1, which has one or two Fc with no $(Gal)_1(GlcNAc)_2(Fuc)_1+(Man)_3(GlcNAc)_2$ glycan.

6. The antibody of claim 1, comprising one or two Fc with a $(Man)_5(GlcNAc)_2$ glycan.

7. The antibody of claim 1, comprising one or two Fc with one or two of the following glycans:
$(Gal)_1(GlcNAc)_2(Fuc)_1(NeuAc)_1+(Man)_3(GlcNAc)_2$
$(Gal)_2(GlcNAc)_2(Fuc)_1(NeuAc)_1+(Man)_3(GlcNAc)_2$.

8. The antibody of claim 1, wherein said antibody has the Fc amino acid sequence SEQ ID NO: 1.

9. The antibody of claim 1, wherein said antibody is a chimeric antibody, a humanized antibody, a full human antibody, a bispecific antibody, an antibody drug conjugate or an antibody fragment.

10. The antibody of claim 1, having ADCC function and no CDC function.

11. The antibody of claim 1, that triggers programmed cell death.

12. A method of treating a cancer comprising administering to a patient an efficient amount of an antibody according to claim 1.

13. The antibody of claim 12, wherein the patient is a refractory or relapse anti-CD20 antibody treated patient.

14. A pool of antibodies according to claim 1, wherein it comprises less or equal than 20% of such antibodies comprising one or two Fc with a $(GlcNAc)_2(Fuc)_1+(Man)_3(GlcNAc)_2$ glycan and/or less or equal than 20% of such antibodies comprising one or two Fc with a $(Gal)_1(GlcNAc)_2(Fuc)_1+(Man)_3(GlcNAc)_2$ glycan.

15. The pool of antibodies of claim 14, wherein it comprises at least 50% of antibodies comprising one or two Fc with $(Man)_5(GlcNAc)_2$ glycans.

16. The pool of antibodies of claim 14, wherein it comprises
less than 2% of antibodies comprising one or two Fc with
$(Gal)_1(GlcNAc)_2(Fuc)_1(NeuAc)_1+(Man)_3(GlcNAc)_2$
and/or less than 3% of antibodies comprising one or two Fc with $(Gal)_2(GlcNAc)_2(Fuc)_1(NeuAc)_1+(Man)_3(GlcNAc)_2$.

17. A pharmaceutical composition comprising an antibody or pool of antibodies of claim 1, and a physiologically acceptable vehicle or excipient.

18. The antibody of claim 1, wherein the wild-type rodent cells are wild-type CHO cells.

19. The antibody of claim 1, wherein the IgG Fc region is an IgG1 Fc region.

20. The antibody of claim 1, wherein the antibody recognizes a non-internalizing epitope on the CD19 antigen.

21. The composition of claim 17, comprising further an antibody directed against CD20, CD52, CD22, EGF receptor, VEGF receptor, mimics ganglioside GD3, CEA or HER-2.

22. The composition of claim 17, comprising further an antibody directed against CD20.

* * * * *